United States Patent [19]

Thompson et al.

[11] Patent Number: 5,527,883
[45] Date of Patent: Jun. 18, 1996

[54] DELTA-ENDOTOXIN EXPRESSION IN PSEUDOMONAS FLUORESCENS

[75] Inventors: Mark Thompson, Del Mar; George E. Schwab, La Jolla, both of Calif.

[73] Assignee: Mycogen Corporation, San Diego, Calif.

[21] Appl. No.: 239,476

[22] Filed: May 6, 1994

[51] Int. Cl.$^6$ .......................... C07K 14/325; C12N 15/32; C12N 15/62; C12N 15/78
[52] U.S. Cl. ...................... 530/350; 536/23.4; 536/23.71; 435/320.1; 435/252.34; 935/10; 935/29
[58] Field of Search .......................... 935/69.1; 530/350; 424/93.431; 519/2; 536/23.4, 23.71; 435/320.1, 252.34

[56] References Cited

U.S. PATENT DOCUMENTS

| | | | |
|---|---|---|---|
| 4,448,885 | 5/1984 | Schnepf et al. | 435/252.33 |
| 4,467,036 | 8/1984 | Schnepf et al. | 435/320.1 |
| 4,797,276 | 1/1989 | Hermstadt et al. | 424/84 |
| 4,849,217 | 7/1989 | Soares et al. | 424/93.461 |
| 4,853,331 | 8/1989 | Hermstadt et al. | 435/252.3 |
| 4,918,006 | 4/1990 | Ellar et al | 435/69.1 |
| 4,948,734 | 8/1990 | Edwards et al. | 514/2 |
| 5,055,294 | 10/1991 | Gilroy | 424/93.2 |
| 5,128,130 | 7/1992 | Gilroy et al. | 424/93.2 |
| 5,151,363 | 9/1992 | Payne | 435/252.5 |
| 5,208,077 | 5/1993 | Proctor et al. | 427/461 |

OTHER PUBLICATIONS

Gaertner, F. H., L. Kim (1988) "Current Applied Recombinant DNA Projects" TIBTECH 6:S4–S7.

Gaertner, F. H. (1989) "Cellular delivery systems for insecticidal proteins: living and non–living microorganisms" in Controlled Deliver of Crop–Protection Agents, pp. 245–255.

Couch, T. L. (1980) "Mosquito Pathogencity of *Bacillus thuringiensis var. israelensis*" Developments in Industrial Microbiology 22:61–76.

Beegle C. C. (1978) "Use of Entomogenous Bacteria in AGroecosystems" in Developments in Industrial Microbiology 20:97–104.

Krieg, A. et al. (1983) "*Bacillus thruringiensis var. tenebrionis*:ein neuer, gegenuber Larven von Coleopteren Wirksamer Pathotyp" Z. ang. 96: Ent. 500–508.

Hofte, H., H. R. Whiteley (1989) "Insecticidal Crystal Proteins of *Bacillus thuringiensis*" Microbiological Reviews 52(2);242–255.

Feitelson, J. S. et al. (1992) "*Bacillus thuringiesis*: Insects and Beyond" Bio/Technology 10:271–275.

Schnepf, H. E., H. R. Whiteley (1981) "Cloning and expression of the *Bacillus thuringiensis*crystal protein gene in *Escherichia coli*" Proc. Natl. Acad. Sci. USA 78(5):2893–2897.

Li, J., J. Carroll, D. J. Ellar (1991) "Crystal structure of insecticidal δ–endotoxin from *Bacillus thruringiensis*at 2.5 A resolution" Nature 353:815–821.

Arvidson, H. et al. (1989) "Specificity of *Bacillus thuringiensis*for lepidopteran larvae: factors involved *in vivo* and in the structure of a purified protoxin" Molecular Microbiology 3(11):1533–1543.

(List continued on next page.)

*Primary Examiner*—Robert A. Wax
*Assistant Examiner*—William W. Moore
*Attorney, Agent, or Firm*—Saliwanchik & Saliwanchik

[57] ABSTRACT

*Bacillus thuringiensis* endotoxin expression in Pseudomonads can be improved by modifying the gene encoding the *Bacillus thuringiensis* endotoxin. Chimeric genes are created by replacing the segment of the *Bacillus thuringiensis* gene encoding a native protoxin with a segment encoding a different protoxin. Exemplified herein is the cryIF/cryI(b) chimera wherein the native cryIF protoxin segment has been substituted by the cryIA(b) protoxin segment, to yield improved expression of the cryIF toxin in Pseudomonads. The invention also concerns novel genes and plasmids.

21 Claims, 10 Drawing Sheets

```
                1                                                                              90
Cons  MENNIQNQCV PYNCLNNPEV EILNEERSTG RLPLDISLSL TRFLLSEFVP GVGVAFGLFD LIWGFITPSD WSLFLLQIEQ LIEQRIETLE
                91                                                                             180
Cons  RNRAITTLRG LADSYEIYIE ALREWEANPN NAQLREDVRI RFANTDDALI TAIHNFTLTS FEIPLLSVYV QAANLHLSLL RDAVSFGQGW
                181                                                                            270
Cons  GLDIATVNNH YNRLINLIHR YTKHCLDTYN QGLENLRGTN TRQWARFNQF RRDLTLTVLD IVALFPNYDV RTYPIQTSSQ LTREIYTSSV
                271                                                                            360
Cons  IEDSPVSANI PNGFNRAEFG VRPPHLMDFM NSLFVTAETV RSQTVWGGHL VSSRNTAGNR INFPSYGVFN PGGAIWIADE DPRPFYRTLS
                361                                                                            450
Cons  DPVFVRGGFG NPHYVLGLRG VAFQQTGTNH TRTFRNSGTI DSLDEIPPQD NSGAPWNDYS HVLNHVTFVR WPGEISGSDS WRAPMFSWTH
                451                                                                            540
Cons  RSATPTHTID PERITQIPLV KAHTLQSGTT VVRGPGFTGG DILRRTSGGP FAYTIVNING QLPQRYRARI RYASTTNLRI YVTVAGERIF
                541                                                                            630
Alt                                                                                    t
Alt                                                                                    i
Alt                                                                1  n     e    a      p l l
Cons  AGQFNKTMDT GDPLTFQSFS YATINTAFTF PMSQSSFTVG ADTFSSGNEV YIDRFELIPV TATfEAEYdL ERAQKAVNEL FTSSNQIGLK
                631                                                                            720
Alt                          e                                                          s
Alt     n   Q  t          r                ng         s  kd   p  q g    r               p
Cons  TDVTDYHIDr VSNLVECLSD EFCLDEKKEL SEKVKHAKRL SDERNLLQDP NFRGINRQLD RGWRGSTDIT IQGGDDVFKE NYVTLLGTFD
                721                                                                            810
Alt                                                               vq
Alt      l         p    e                          l    r        fe s rKCGE PNRCAPHLEW NPDLDCSCRD
Cons  ECYPTYLYQK IDESKLKAYT RYQLRGYIED SQDLEIYLIR YNAKHETVNV PGTGSLWPLS APSPIG----  ----------  ----------
```

OTHER PUBLICATIONS

Choma, C. T. et al. (1990) "Unusual proteolysis of the protoxin and toxin from *Bacillus thuringiensis*" Eur. J. Biochem. 189:523–527.

Haider, M. Z. et al. (1986) "Specificity of *Bacillus thuringiensis* var. *colmeri*insecticidal δ–endotoxin is determined by differential proteolytic processing of the protoxin" Eur. J. Biochem. 156:531–540.

Aronson, A. I. et al. (1991) "The Solubility of Inclusion Proteins from*Bacillus thuringiensis Is Dependant upon Protoxin Composition and Is a Factor in Toxicity to Insects*" Appl. Environ. Microbiol. 57(4):981–1986.

Honee, G. et al. (1991) "The C–terminal domain of the toxic fragment of a *Bacillus thuringiensis*crystal protein determines receptor binding" Molecular Microbiology 5(11):2799–2806.

Honee, G. et al. (1990) "A Translation Fusion Product of Two Different Insecticidal Crystal Protein Genes of*Bacillus thuringiensis* Exhibits an Enlarged Insecticidal Spectrum" Appl. Environ. Microbiol. 56(3):823–825.

Honee et al. App. Envir Micrb. vol. 56(3) pp. 823–825(1990).

Chambers J. Bacter vol. 173 p. 3966 (1991).

Fig. 9A

```
        1
Cons    MENNIQNQCV PYNCLNNPEV EILNEERSTG RLPLDISLSL TRFLLSEFVP GVGVAFGLFD LIWGFITPSD WSLFLLQIEQ LIEQRIETLE
                                                                                                      90
        91
Cons    RNRAITTLRG LADSYEIYIE ALREWEANPN NAQLREDVRI RFANTDDALI TAINNFTLTS FEIPLLSVYV QAANLHLSLL RDAVSFGQGW
                                                                                                     180
        181
Cons    GLDIATVNNH YNRLINLIHR YTKHCLDTYN QGLENLRGTN TRQWARFNQF RRDLTLTVLD IVALFPNYDV RTYPIQTSSV LTREIYTSSV
                                                                                                     270
        271
Cons    IEDSPVSANI PNGFNRAEFG VRPPHLMDFM NSLFVTAETV RSQTVWGGHL VSSRNTAGNR INFPSYGVFN PGGAIWIADE DPRPFYRTLS
                                                                                                     360
        361
Cons    DPVFVRGGFG NPHYVLGLRG VAFQQTGTNH TRTFRNSGTI DSLDEIPPQD NSGAPWNDYS HVLNHVTFVR WPGEISGSDS WRAPMFSWTH
                                                                                                     450
        451
Cons    RSATPTNTID PERITQIPLV KAHTLQSGTT VVRGPGFTGG DILRRTSGGP FAYTIVNING QLPQRYRARI RYASTTNLRI YVTVAGERIF
                                                                                                     540
        541                                                          t
                                                                     i           p     l i
                                                                     l   e       a        p
Alt                                                                  n   a       r
Alt                                                                          e
Cons    AGQFNKTMDT GDPLTFQSFS YATINTAFTF PMSQSSFFTVG ADTFSSGNEV YIDRFELIPV TATFEAEYdL ERAQKAVNEL FTSSNQIGLK
                                                                                                     630
        631                            s
                                   ng             s       kd    p       g   g          r
Alt                                e              r                                    p
Alt                                                                                 s
Cons    TDVTDYHIDI VSNLVECLSD EFCLDEKKEL SEKVKHAKRL SDERNLLQDP NFRGINRQLD RGWRGSTDIT IQGGDDVFKE NYVTLLGTFD
                                                                                                     720
        721                            vq
        l      Q         p                          fe   s  rKCGE
Alt     n                    t                  r
Alt                                  e
Cons    ECYPTYLYQK IDESKLKAYT RYQLRGYIED SQDLEIYLIR YNAKHETVNV PGTGSLWPLS APSPIG---                 PNRCAPHLEW NPDLDCSCRD
                                                                                                     810
```

Fig. 9B

```
            811                                                          900
Alt         GE                           i         d          e  i      gra  ql
Cons        --KCAHHSHH FSLDIDVGCT DLNEDLGVWV IFKIKTQDGH ARLGNLEFLE EK-PLVGEAL ARVKRAEKKW RDKREKLEWE TNIVYKEAKE 901                                                          990
Alt                       q                  t     r  q             d            vg   k      f
Cons        SVDALFVNSQ YDRLQADTNI AMIHAADKRV HSIREAYLPE LSVIPGVNAA IFEELEGRIF TAFSLYDARN VIKNGDFNNG LSCWNVKGHV 991                                                          1080
Alt                q                                            t                    f                n    g
Cons        DVEEQNNHRS VLVVPEWEAE VSQEVRVCPG RGYILRVTAY KEGYGEGCVT IHEIENNTDE LKFSNCVEEE VYPNNTVTCN DYTATQEEYE 1081                                                         1170
Alt         a      c     et  g   y       v                                         q     KELEYFPETD KVWIEIGETE GTFIVDSVEL
Cons        GTYTSRNRGY DGAYESNSSV PADYASAYEE KAYTDGRRDN PCESNRGYGD YTPLPAGYVT 1171
Cons        LLMEE
```

5,527,883

DELTA-ENDOTOXIN EXPRESSION IN PSEUDOMONAS FLUORESCENS

BACKGROUND OF THE INVENTION

The soil microbe *Bacillus thuringiensis* (*B.t.*) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain *B.t.* toxin genes have been isolated and sequenced, and recombinant DNA-based *B.t.* products have been produced and approved for use. In addition, with the use of genetic engineering techniques, new approaches for delivering these *B.t.* endotoxins to agricultural environments are under development, including the use of plants genetically engineered with endotoxin genes for insect resistance and the use of stabilized intact microbial cells as *B.t.* endotoxin delivery vehicles (Gaertner, F. H., L. Kim [1988] *TIBTECH* 6:S4–S7). Thus, isolated *B.t.* endotoxin genes are becoming commercially valuable.

Until the last ten years, commercial use of *B.t.* pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystalline δ-endotoxin which is toxic to the larvae of a number of lepidopteran insects.

In recent years, however, investigators have discovered *B.t.* pesticides with specificities for a much broader range of pests. For example, other species of *B.t.*, namely *israelensis* and *tenebrionis* (a.k.a. *B.t.* M-7, a.k.a. *B.t.* san diego), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255). See also Couch, T. L. (1980) "Mosquito Pathogenicity of *Bacillus thuringiensis* var. *israelensis*," Developments in Industrial Microbiology 22:61–76; Beegle, C. C., (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508, describe *Bacillus thuringiensis* var. *tenebrionis*, which is reportedly active against two beetles in the order Coleoptera. These are the Colorado potato beetle, *Leptinotarsa decemlineata*, and *Agelastica alni*.

Recently, new subspecies of *B.t.* have been identified, and genes responsible for encoding active δ-endotoxin proteins have been isolated (Höfte, H., H. R. Whiteley [1989] *Microbiological Reviews* 52(2):242–255). Höfte and Whiteley classified *B.t.* crystal protein genes into 4 major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported. (Feitelson, J. S., J. Payne, L. Kim [1992] *Bio/Technology* 10:271–275).

The cloning and expression of a *B.t.* crystal protein gene in *Escherichia coli* has been described in the published literature (Schnepf, H. E., H. R. Whiteley [1981] *Proc. Natl. Acad. Sci. U.S.A.* 78:2893–2897). U.S. Pat. No. 4,448,885 and U.S. Pat. No. 4,467,036 both disclose the expression of *B.t.* crystal protein in *E. coli.* Hybrid *B.t.* crystal proteins have been constructed that exhibit increased toxicity and display an expanded host range to a target pest. See U.S. Pat. Nos. 5,128,130 and 5,055,294. U.S. Pat. Nos. 4,797,276 and 4,853,331 disclose *B. thuringiensis* strain *tenebrionis* (a.k.a. M-7, a.k.a. *B.t.* san diego) which can be used to control coleopteran pests in various environments. U.S. Pat. No. 4,918,006 discloses *B.t.* toxins having activity against dipterans. U.S. Pat. No. 4,849,217 discloses *B.t.* isolates which have activity against the alfalfa weevil. U.S. Pat. No. 5,208,077 discloses coleopteran-active *Bacillus thuringiensis* isolates. U.S. Pat. No. 5,151,363 and U.S. Pat. No. 4,948,734 disclose certain isolates of *B.t.* which have activity against nematodes. As a result of extensive research and investment of resources, other patents have issued for new *B.t.* isolates and new uses of *B.t.* isolates. However, the discovery of new *B.t.* isolates and new uses of known *B.t.* isolates remains an empirical, unpredictable art.

A majority of *Bacillus thuringiensis* δ-endotoxin crystal protein molecules are composed of two functional segments. The protease-resistant core toxin is the first segment and corresponds to about the first half of the protein molecule. The three-dimensional structure of a core segment of a cryIIIA *B.t.* δ-endotoxin is known and it is proposed that all related toxins have that same overall structure (Li, J., J. Carroll, D. J. Ellar [1991] *Nature* 353:815–821). The second half of the molecule is the second segment. For purposes of this application, this second segment will be referred to herein as the "protoxin segment." The protoxin segment is believed to participate in toxin crystal formation (Arvidson, H., P. E. Dunn, S. Strand, A. I. Aronson [1989] *Molecular Microbiology* 3:1533–1534; Choma, C. T., W. K. Surewicz, P. R. Carey., M. Pozsgay, T. Raynor, H. Kaplan [1990] *Eur. J. Biochem.* 189:523–527). The full 130 kDa toxin molecule is rapidly processed to the resistant core segment by protease in the insect gut. The protoxin segment may thus convey a partial insect specificity for the toxin by limiting the accessibility of the core to the insect by reducing the protease processing of the toxin molecule (Haider, M. Z., B. H. Knowles, D. J. Ellar [1986] *Eur. J. Biochem.* 156:531–540) or by reducing toxin solubility (Aronson, A. I., E. S. Han, W. McGaughey, D. Johnson [1991] *Appl. Environ. Microbiol.* 57:981–986).

Chimeric proteins joined within the toxin domains have been reported between CryIC and CryIA(b) (Honee, G., D. Convents, J. Van Rie, S. Jansens, M. Perferoen, B. Visser [1991] *Mol. Microbiol.* 5:2799–2806); however, the activity of these chimeric proteins was either much less, or undetectable, when compared to CryIC on a relevant insect.

Honee et al. (Honee, G., W. Vriezen, B. Visser [1990] *Appl. Environ. Microbiol.* 56:823–825) also reported making a chimeric fusion protein by linking tandem toxin domains of CryIC and CryIA(b). The resulting protein had an increased spectrum of activity equivalent to the combined activities of the individual toxins; however, the activity of the chimeric was not increased toward any one of the target insects.

BRIEF SUMMARY OF THE INVENTION

The subject invention concerns the discovery that expression of *Bacillus thuringiensis* (*B.t.*) δ-endotoxin in Pseudomonas can be substantially improved by modifying the gene which encodes the *B.t.* toxin. Specifically, *B.t.* endotoxin expression in *P. fluorescens* can be improved by reconstructing the gene so as to replace the native protoxin-encoding segment with an alternate protoxin segment, yielding a chimeric gene.

In specific embodiments of the subject invention, chimeric genes can be assembled that substitute a heterologous protoxin segment for a native cryIF protoxin segment. In particular, all or part of the protoxin-encoding region of a cryIA(b) gene can be used in place of all or part of the region which encodes the protoxin for a native cryIF toxin. Similarly, a chimeric gene can be constructed wherein the region encoding all or part of the protoxin of a cryIF toxin is replaced by DNA encoding all or part of the protoxin of a cryIA(c)/cryIA(b) chimeric gene. In a specific embodiment, the cryIA(c)/cryIA(b) chimeric gene is that which has been denoted 436 and which is described in U.S. Pat. No. 5,128,130. This gene can be obtained from the plasmid in *P. fluorescens* MR436.

The subject invention also includes use of the chimeric gene encoding the claimed toxin. The chimeric gene can be introduced into a wide variety of microbial or plant hosts. A transformed host expressing the chimeric gene can be used to produce the lepidopteran-active toxin of the subject invention. Transformed hosts can be used to produce the insecticidal toxin or, in the case of a plant cell transformed to produce the toxin, the plant will become resistant to insect attack. The subject invention further pertains to the use of the chimeric toxin, or hosts containing the gene encoding the chimeric toxin, in methods for controlling lepidopteran pests.

Still further, the invention includes the treatment of substantially intact recombinant cells producing the chimeric toxin of the invention. The cells are treated to prolong the lepidopteran activity when the substantially intact cells are applied to the environment of a target pest. Such treatment can be by chemical or physical means, or a combination of chemical and physical means, so long as the chosen means do not deleteriously affect the properties of the pesticide, nor diminish the cell's capability of protecting the pesticide. The treated cell acts as a protective coating for the pesticidal toxin. The toxin becomes active upon ingestion by a target insect.

BRIEF DESCRIPTION OF THE DRAWINGS

FIG. 9—A CryIF/CryIA(b) chimeric protein sequence and residue-by-residue substitutions. The 'Cons' line shows a CryIF/CryIA(b) chimeric sequence. The 'Alt' lines show residue-by-residue substitutions found in the 436 protein, CryIA(b) variant proteins and CryIF protoxins.

BRIEF DESCRIPTION OF THE SEQUENCES

Figure 1:
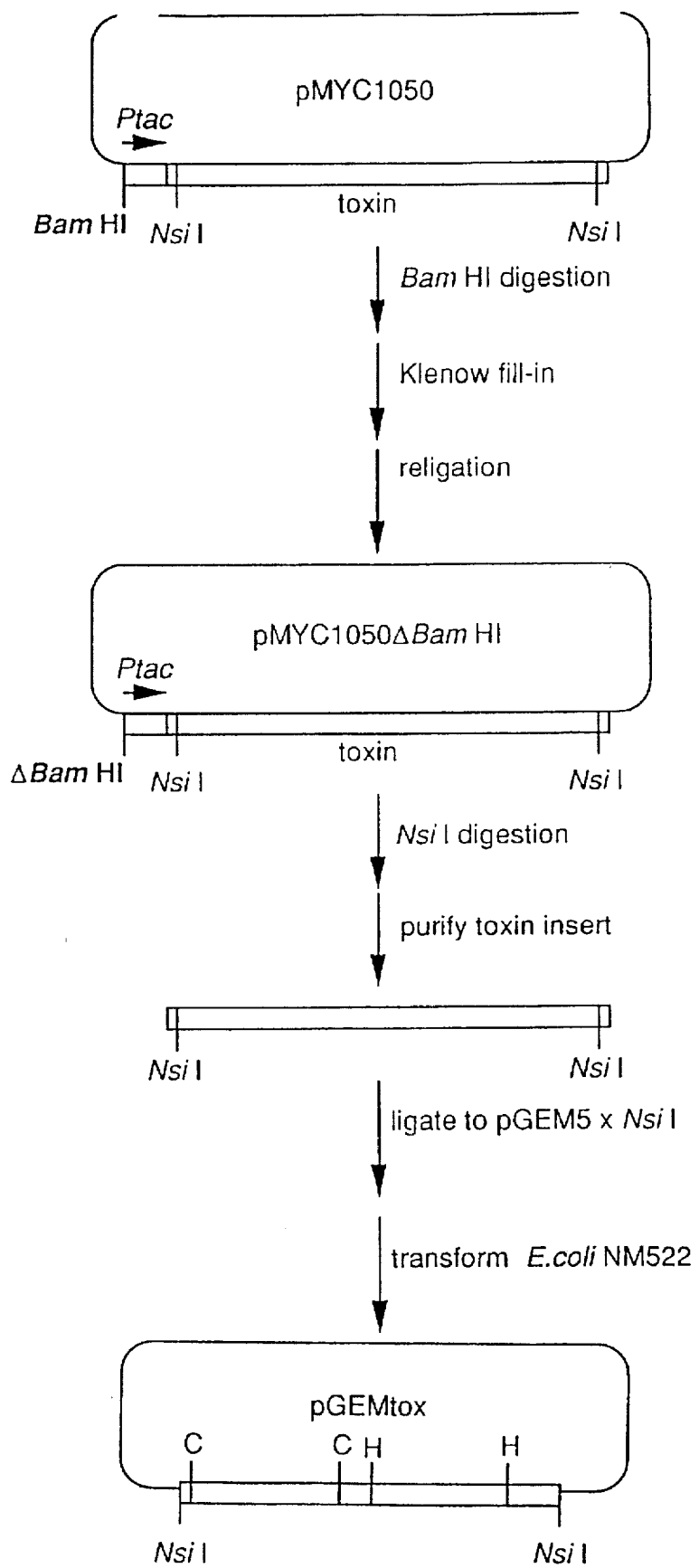
FIG. 1—The BamHI site is removed from pMYC1050 by a fill-in reaction with Klenow polymerase to give plasmid pMYC1050ΔBamHI. To facilitate cloning, an NsiI DNA fragment that contains most of the toxin open reading frame is cloned into pGEM5. The resulting plasmid is called pGEMtox. C=ClaI, H=HindIII.

SEQ ID NO. 1 is oligonucleotide primer "A"

SEQ ID NO. 2 is oligonucleotide primer "B"

SEQ ID NO. 3 is oligonucleotide primer "C"

SEQ ID NO. 4 is oligonucleotide primer "D"

SEQ ID NO. 5 is oligonucleotide primer "E"

SEQ ID NO. 6 is oligonucleotide primer "F"

SEQ ID NO. 7 is oligonucleotide primer "G"

SEQ ID NO. 8 is oligonucleotide primer "L"

SEQ ID NO. 9 is oligonucleotide primer "N"

SEQ ID NO. 10 is oligonucleotide primer "O"

SEQ ID NO. 11 is oligonucleotide primer "H"

SEQ ID NO. 12 is oligonucleotide primer "I"

SEQ ID NO. 13 is oligonucleotide primer "J"

SEQ ID NO. 14 is oligonucleotide primer "K"

SEQ ID NO. 15 is oligonucleotide primer "P"

SEQ ID NO. 16 is oligonucleotide primer "Q"

SEQ ID NO. 17 is oligonucleotide primer "M"

SEQ ID NO. 18 shows the toxin-encoding DNA sequence of pMYC2224.

SEQ ID NO. 19 shows the predicted amino acid sequence of the toxin encoded by pMYC2224.

SEQ ID NO. 20 shows the toxin-encoding DNA sequence of pMYC2239.

SEQ ID NO. 21 shows the predicted amino acid sequence of the toxin encoded by pMYC2239.

SEQ ID NO. 22 shows the toxin-encoding DNA sequence of pMYC2244, which encodes a cryIF/cryIA(b) chimeric toxin.

SEQ ID NO. 23 shows the predicted amino acid sequence of the cryIF/cryIA(b) chimeric toxin encoded by pMYC2244.

SEQ ID NO. 24 shows the toxin-encoding DNA sequence of pMYC2243.

SEQ ID NO. 25 shows the predicted amino acid sequence of the toxin encoded by pMYC2243.

SEQ ID NO. 26 shows the toxin-encoding DNA sequence of pMYC2523, which encodes a cryIF/cryIA(b) chimeric toxin with codon rework.

SEQ ID NO. 27 shows the predicted amino acid sequence of the toxin encoded by pMYC2523.

SEQ ID NO. 28 shows the toxin-encoding DNA sequence of pMYC2254, which encodes a cryIF/436 chimeric toxin.

SEQ ID NO. 29 shows the predicted amino acid sequence of the toxin encoded by pMYC2254.

SEQ ID NO. 30 is a characteristic sequence of cryI toxins. This sequence ends at residue 601 of SEQ ID NO. 30.

SEQ ID NO. 31 is the eight amino acids preceding amino acid 1043 in SEQ ID NO. 23.

SEQ ID NO. 32 shows the amino acid sequence of a native cryIF toxin.

SEQ ID NO. 33 shows the amino acid sequence of a native cryIA(b) toxin.

SEQ ID NO. 34 shows the amino acid sequence of a cryIA(c)/cryIA(b) toxin.

DETAILED DISCLOSURE OF THE INVENTION

The subject invention concerns the discovery that certain chimeric genes encoding *B.t.* toxins have improved expression in recombinant *Pseudomonas fluorescens*. The chimeric genes encode toxins wherein all or part of the native protoxin portion has been replaced with all or part of the protoxin from another *B.t.* toxin. Specifically exemplified herein are genes which encode a *B.t.* toxin which consists essentially of a cryIF core N-terminal toxin portion attached to a protoxin segment which is derived from either a cryIA(b) toxin or a cryIA(c)/cryIA(b) toxin as described herein. As used herein, reference to a "core" toxin portion refers to the portion of the full length *B.t.* toxin, other than the protoxin, which is responsible for the pesticidal activity of the toxin.

Bacteria harboring plasmids useful according to the subject invention are the following:

| Culture | Repository No. | U.S. Pat. No. |
| --- | --- | --- |
| *P. fluorescens* (pM3,130-7) | NRRL B-18332 | 5,055,294 |
| *P. fluorescens* MR436 (pM2,16-11, aka pMYC436) | NRRL B-18292 | 5,128,130 |
| *E. coli* NM522 (pMYC1603) | NRRL B-18517 | 5,188,960 |

It should be understood that the availability of a deposit does not constitute a license to practice the subject invention in derogation of patent rights granted by governmental action.

The flow charts of FIGS. 1-8 provide a general overview of vector construction that can be carried out according to the subject invention. BamHI and PvuI cloning sites can be introduced into acryIA(c)/cryIA(b) chimeric toxin gene by mutagenesis using the PCR technique of Splice Overlap Extension (SOE) (Horton, R. M., H. D. Hunt, S. N. Ho, J. K. Pullen, L. R. Pease [1989] Gene 77:61–68) to give plasmid pMYC2224. A region of the cryIF gene from a cryIF-containing plasmid such as pMYC1260 can be generated by PCR and substituted for the BamHI-PvuI cryIA(c)/cryIA(b) gene fragment of pMYC2224. The new plasmid, which we designated pMYC2239, consisted of a short segment of cryIA(c) followed by cryIF to the toxin/protoxin segment junction. Thus, the protoxin segment was now derived from cryIA(b) (pMYC1050). An ApaI fragment derived from the cryIF clone (pMYC2047) was substituted for the ApaI fragment in pMYC2239. The resulting clone (pMYC2244) consisted of cryIF from the initiator methionine to the toxin/protoxin segment junction and cryIA(b) to the end of the coding region. Clone pMYC2243 was constructed by SOE to introduce silent codon changes in a limited region. The ApaI fragment from pMYC2243 that contained the silent changes was substituted for the ApaI fragment in pMYC2244 to give clone pMYC2523. The chimeric pMYC2523 showed an expression improvement over pMYC2243, which contains unchanged cryIF protein sequence.

A cryIF/436 chimera can be assembled by substituting the PvuI-BstEII protein segment-containing fragment of pMYC2523 with an equivalent fragment generated by PCR from a plasmid containing a cryIA(c)/cryIA(b) gene. One such gene is the 436 gene (e.g., pMYC467, as disclosed in U.S. Pat. Nos. 5,128,130 and 5,169,760). This construction also results in improved expression compared to the native cryIF protein sequence.

The chimeric toxins of the subject invention comprise a full core N-terminal toxin portion of a *B.t.* toxin and, at some point past the end of the toxin portion, the protein has a transition to a heterologous protoxin sequence. The transition to the heterologous protoxin segment can occur at approximately the toxin/protoxin junction or, in the alternative, a portion of the native protoxin (extending past the toxin portion) can be retained with the transition to the heterologous protoxin occurring downstream. As an example, one chimeric toxin of the subject invention has the full toxin portion of cryIF (amino acids 1–601) and a heterologous protoxin (amino acids 602 to the C-terminus). In a preferred embodiment, the heterologous portion o:15 the protoxin is derived from a cryIA(b) or 436 toxin.

A person skilled in this art will appreciate that *B.t.* toxins, even within a certain class such as cryIF, will vary to some extent in length and the precise location of the transition from toxin portion to protoxin portion. Typically, the cryIA(b) and cryIF toxins are about 1150 to about 1200 amino acids in length. The transition from toxin portion to protoxin portion will typically occur at between about 50% to about 60% of the full length toxin. The chimeric toxin of the subject invention will include the full expanse of this core N-terminal toxin portion. Thus, the chimeric toxin will comprise at least about 50% of the full length cryIF *B.t.* toxin. This will typically be at least about 590 amino acids. With regard to the protoxin portion, the full expanse of the cryIA(b) protoxin portion extends from the end of the toxin portion to the C-terminus of the molecule. It is the last about 100 to 150 amino acids of this portion which are most critical to include in the chimeric toxin of the subject invention. In a chimeric toxin specifically exemplified herein, at least amino acids 1043 (of SEQ ID NO. 23) to the C-terminus of the cryIA(b) molecule are utilized. Amino acid 1043 in SEQ ID NO. 23 is preceded by the sequence Tyr Pro Ash Asn Thr Val Thr Cys (SEQ ID NO. 31). This amino acid sequence marks the location in the protoxin segment of the molecule beyond which heterologous amino acids will always occur in the chimeric toxin. In another example, the peptide shown as SEQ ID NO. 31 occurs at amino acids 1061 to 1068. In this case, amino acids 1069 to the C-terminus are preferably heterologous (SEQ ID NO. 29). The peptide shown in SEQ ID NO. 31 can be found at positions 1061 to 1068 in FIG. 9. Thus, it is at least the last approximately 5 to 10% of the overall B.t. protein which should comprise heterologous DNA (compared to the cryIF core N-terminal toxin portion) in the chimeric toxin of the subject invention. In the specific examples contained herein, heterologous protoxin sequences occur from amino acid 640 to the C-terminus.

Thus, a preferred embodiment of the subject invention is a chimeric B.t. toxin of about 1150 to about 1200 amino acids in length, wherein the chimeric toxin comprises a cryIF core N-terminal toxin portion of at least about 50 to 60% of a full cryIF molecule, but no more than about 90 to 95% of the full molecule. The chimeric toxin further comprises a cryIA(b) or a 436 protoxin C-terminal portion which comprises at least about 5 to 10% of the cryIA(b) or 436 molecule. The transition from cryIF to cryIA(b) or 436 sequence thus occurs within the protoxin segment (or at the junction of the toxin and protoxin segments) between about 50% and about 95% of the way through the molecule. In the specific examples provided herein, the transitions from the cryIF sequence to the heterologous protoxin sequences occur prior to the end of the peptide sequence shown in SEQ ID NO. 31.

A specific embodiment of the subject invention is the chimeric toxin shown in FIG. 9. Other constructs may be made and used by those skilled in this art having the benefit of the teachings provided herein. The core toxin segment of cryI proteins characteristically ends with the sequence: Val/Leu Tyr/Ile Ile Asp Arg/Lys Ile/Phe Glu Ile/Phe/Leu Ile/Leu/Val Pro/Leu Ala/Val Glu/Thr/Asp (SEQ ID NO. 30), which ends at residue 601 of SEQ ID NO. 23. Additionally, the protoxin segments of the cryI toxins (which follow residue 601) bear more sequence similarity than the toxin segments. Because of this sequence similarity, the transition point in the protoxin segment for making a chimeric protein between the cryIF sequence and the cryIA(b) or 436 sequence can be readily determined by one skilled in the art. From studies of data regarding the partial proteolysis of CryI genes, the heterogeneity and least-conserved amino acid regions are found after the conserved cryI protoxin sequence, positions 1061–1068 of FIG. 9.

Therefore a chimeric toxin of the subject invention can comprise the full cryIF toxin and a portion of the cryIF protoxin, transitioning to the corresponding cryIA(b) or 436 sequence at any position between the end of the toxin segment (as defined above) and the end of the peptide sequence shown in SEQ ID NO. 31. Preferably, the amino acid sequence of the C-terminus of the chimeric toxin comprises a cryIA(b) sequence or a sequence from the 436 gene or an equivalent of one of these sequences.

CryIF toxins, and genes which encode these toxins, are well known in the art. CryIF genes and toxins have been described in, for example, Chambers et al. (1991) *J. Bacteriol.* 173:3966. CryIA(b) genes and toxins have been described in, for example, Höfte et at (1986) *Eur. J. Biochem.* 161:273; Geiser et al. (1986) *Gene* 48:109; and Haider et at (1988) *Nucleic Acids Res.* 16:10927. The skilled artisan having the benefit of the teachings contained herein could readily identify and use DNA which encodes the toxin N-terminal portion of a cryIF molecule and the C-terminal protoxin portion of the cryIA(b) toxins.

FIG. 9 provides examples of amino acid substitutions which can be used in the toxins of the subject invention. It is also well known in the art that various mutations can be made in a toxin sequence without changing the activity of a toxin. Furthermore, due to the degeneracy of the genetic code, a variety of DNA sequences can be used to encode a particular toxin. These alternative DNA and amino acid sequences can be used according to the subject invention by a person skilled in this art.

The protoxin substitution techniques of the subject invention can be used with other classes of B.t. endotoxins to enhance expression of the toxin. The technique would be most applicable to other B.t. toxins which have the characteristic sequence shown in SEQ ID NO. 30.

The subject invention not only includes the novel chimeric toxins and the genes encoding these toxins but also includes uses of these novel toxins and genes. For example, a gene of the subject invention may be used to transform host cells. These host cells expressing the gene and producing the chimeric toxin may be used in insecticidal compositions or, in the case of a transformed plant cell, in conferring insect resistance to the transformed cell itself.

Genes and toxins. The genes and toxins useful according to the subject invention include not only the full length sequences disclosed but also fragments of these sequences, variants, and mutants which retain the characteristic pesticidal activity of the toxins specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins.

It should be apparent to a person skilled in this art that genes encoding active toxins can be identified and obtained through several means. The specific genes (or portions thereof which encode toxin or protoxin domains) useful according to the subject invention may be obtained from the recombinant isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 can be used to systematically cut off nucleotides from the ends of these genes. Alternatively, site-directed mutagenesis can be used. Also, genes which encode active fragments may be obtained using a variety of restriction enzymes. Proteases may be used to directly obtain active fragments of these toxins.

Fragments and equivalents which retain the pesticidal activity of the exemplified toxins would be within the scope of the subject invention. Also, because of the redundancy of the genetic code, a variety of different DNA sequences can encode the amino acid sequence disclosed herein. It is well within the skill of a person trained in the art to create these alternative DNA sequences encoding the same, or essentially the same, toxin. These variant DNA sequences are within the scope of the subject invention. As used herein, reference to "essentially the same" sequence refers to sequences which have amino acid substitutions, deletions, additions, or insertions which do not materially affect pesticidal activity or expression level. Fragments retaining pesticidal activity are also included in this definition.

A further method for identifying the toxins and genes of the subject invention is through the use of oligonucleotide probes. These probes are detectable nucleotide sequences. These sequences may be detectable by virtue of an appropriate label or may be made inherently fluorescent as described in International Application No. WO93/16094. As is well known in the art, if the probe molecule and nucleic acid sample hybridize by forming a strong bond between the two molecules, it can be reasonably assumed that the probe and sample have substantial homology. Preferably, hybridization is conducted under stringent conditions by techniques well-known in the art, as described, for example, in Keller, G. H., M. M. Manak (1987) *DNA Probes*, Stockton Press, New York, N.Y., pp. 169–170. Detection of the probe provides a means for determining in a known manner whether hybridization has occurred. Such a probe analysis provides a rapid method for identifying toxin-encoding genes of the subject invention. Preferably, such genes would be cryIF genes whose core toxin-encoding portions can then be used with a cryIA(b) or 436 protoxin-encoding portion to create a chimeric gene according to the subject invention. The nucleotide segments which are used as probes according to the invention can be synthesized using DNA synthesizer and standard procedures. These nucleotide sequences can also be used as PCR primers to amplify genes of the subject invention.

Certain chimeric toxins of the subject invention have been specifically exemplified herein. It should be readily apparent that the subject invention comprises variant or equivalent toxins (and nucleotide sequences encoding equivalent toxins) having the same or similar pesticidal activity of the exemplified toxin. Equivalent toxins will have amino acid homology with the exemplified toxin. This amino acid homology will typically be greater than 75%, preferably be greater than 90%, and most preferably be greater than 95%. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same class fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

Recombinant hosts. A gene encoding a chimeric toxin of the subject invention can be introduced into a wide variety of microbial or plant hosts. Expression of the toxin gene results, directly or indirectly, in the intracellular production and maintenance of the pesticidal chimeric toxin. With suitable microbial hosts, e.g., Pseudomonas, the microbes can be applied to the situs of the pest, where they will proliferate and be ingested. The result is control of the pest. Alternatively, the microbe hosting the toxin gene can be treated under conditions that prolong the activity of the toxin and stabilize the cell. The treated cell, which retains the toxic activity, then can be applied to the environment of the target pest.

Where the gene encoding the chimeric toxin is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, SerraHa, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans*. Of particular interest are the pigmented microorganisms.

A wide variety of ways are available for introducing a gene encoding a chimeric toxin into a microorganism host under conditions which allow for the stable maintenance and expression of the gene. These methods are well known to those skilled in the art and are described, for example, in U.S. Pat. No. 5,135,867, which is incorporated herein by reference.

Treatment of cells. As mentioned above, recombinant cells producing the chimeric toxin of the subject invention can be treated to prolong the toxic activity and stabilize the cell. The pesticide microcapsule that is formed comprises the B.t. toxin within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the gene encoding a chimeric toxin of the subject invention, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Hetty's fixative (See: Humason, Gretchen L., *Animal Tissue Techniques*, W.H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Since the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bioavailability or bioactivity of the toxin.

Characteristics of particular interest in selecting a host cell for purposes of production include ease of introducing the gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the gene encoding a chimeric toxin of the subject invention may be grown in any convenient nutrient medium, where the DNA construct provides a selective advantage, providing for a selective medium so that substantially all or all of the cells retain the recombinant gene. These cells may then be harvested in accordance with conventional methods. Alternatively, the cells can be treated prior to harvesting.

Formulations. Recombinant microbes comprising a gene encoding a chimeric toxin disclosed herein, can be formulated into bait granules and applied to the soil. Formulated product can also be applied as a seed-coating or root treatment or total plant treatment at later stages of the crop cycle. Plant and soil treatments may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

Materials and Methods

NACS (Bethesda Research Labs, Gaithersburg, Md.) column chromatography was used for purification of electroeluted DNA. It was performed according to the manufacturer's directions, except that the buffers were modified to 0.5X TBE/0.2M NaCl for binding, and 0.5X TBE/2.0M NaCl for elution.

Random priming labeling of DNA with $\alpha$-[$^{32}$P]dATP was done with a kit (Boehringer-Mannheim Biochemicals, Indianapolis, Ind.) according to the manufacturer's directions.

Gel purification refers to sequential application of agarose-TBE gel electrophoresis, electroelution, and NACS column chromatography for purification of selected DNA fragments, methods which are well known in the art.

Polymerase chain reaction (PCR) amplification of DNA was done for 25 cycles on a Perkin Elmer (Norwalk, Conn.) thermal cycler with the following cycle parameters: 94° C. for 1 minute, 37° C. for 2 minutes, 72° C. for 3 minutes (each 72° C. cycle has a 5 second extension time). PCR DNA products were proteinase K treated to improve cloning efficiency (Crowe, J. S., Cooper, H. J., Smith, M. A., Sims, M. J., Parker, D., Gewert, D. [1991] Nucl. Acids Res. 19:184).

Oligodeoxyribonucleotides (oligonucleotides) were synthesized on an Applied Biosystems (Foster City, Calif.) model 381A DNA synthesizer. Purification was done with Nensorb columns (New England Nuclear-Dupont, Wilmington, Del.), if necessary, according to the manufacturer's instructions.

Electroporation of *Pseudomonas fluorescens* was done with log-phase cells grown in L-broth (LB) at 30° C. on a rotary shaker. Cells were washed 2 to 3 times with ice-cold sterile distilled water and concentrated to 0.03× starting volume in distilled water. DNA in 1–20 μl was mixed with 50–300 μl of cells. Parameters selected for the Biorad Gene Pulser (Bio-Rad, Richmond, Calif.) were 200 ohms, 25 microfarads, and 2.25 kilovolts in a cuvette with a 0.2 cm electrode gap. Following electroporation, one milliliter of LB was added and cells were held on ice for at least 2 minutes. Cells were then incubated for 2 hours to overnight at 30° C. without shaking.

B.t. toxin expression in *P. fluorescens* was done in the recommended medium found in the *Manual of Methods for General Bacteriology* (P. Gerhardt et al., 1981, American Society for Microbiology, Washington, D.C.). Glycerol was substituted for glucose. The recipe was made with tap water and the pH adjusted to 7.2. Seed flasks were made from L-broth. The following recipes apply:

| Base Medium (for 1 liter) | |
|---|---|
| glycerol | 65 g |
| $(NH_4)_2SO_4$ | 1.0 g |
| $Na_2HPO_4$ | 5.24 g |
| $KH_2PO_4$ | 2.77 g |
| Yeast extract | 5.0 g |
| Casamino acids | 1.0 g |
| Metals 44 (for 100 ml) | |
| EDTA | 250 mg |
| $ZnSO_4 \cdot 7H_2O$ | 1095 mg |
| $FeSO_4 \cdot 7H_2O$ | 500 mg |
| $MnSO_4 \cdot H_2O$ | 154 mg |
| $CuSO_4 \cdot 5H_2O$ | 39.2 mg |
| $Co(NO_3)_2 \cdot 6H_2O$ | 24.8 mg |
| $Na_2B_4O_7 \cdot 10H_2O$ | 17.7 mg |
| Add a few drops of 6 N $H_2SO_4$ to retard precipitation. | |
| Huntner's Mineral Mix (for 1 liter) | |
| Nitriloacetic acid (dissolved and neutralized with KOH) | 10 g |
| $MgSO_4 \cdot 7H_2O$ | 14.45 g |
| $CaCl_2 \cdot 2H_2O$ | 3.33 g |
| $(NH_4)_6Mo_7O_{24} \cdot 4H_2O$ | 9.25 g |
| $FeSO_4 \cdot 7H_2O$ | 99 mg |
| Metals 44 | 50 ml |
| pH adjusted to 6.6–6.8 | |

At inoculation for analysis of *B.t.* toxin expression, 4 ml of Huntner's Mineral Mix was added per 200 ml of broth. Flasks were then given a 2% inoculum, by volume, of an overnight culture. Cultures were allowed to grow for 24 hours at 32° C. at ≧200 rpm. At this point, they were induced with 0.75 mM IPTG and supplemented with 2 g yeast extract. Protein gels were run on samples pulled at 48 and 72 hours. The approximately 130 kDa protein was quantified by laser densitometry.

Following are examples which illustrate procedures, including the best mode, for practicing the invention. These examples should not be construed as limiting. All percentages are by weight and all solvent mixture proportions are by volume unless otherwise noted.

EXAMPLE 1

Expression Vector Modification by Splice Overlap Extension (SOE)

A cloning vector can be constructed based on pTJS260, a broad host-range plasmid derived from RSF1010 (pTJS260 can be obtained from Dr. Donald Helinski, U.C. San Diego). An example of the system used in the vector construction can be found in EPO patent application 0 471 564. A cryIA(c)/cryIA(b) gene, referred to herein as the 436 gene and toxin, are described in U.S. Pat. No. 5,055,294. A plasmid designated pMYC1050 contains a cryIA(c)/cryIA(b) chimeric gene known as the 420 gene. pMYC1050 was constructed by re-cloning the toxin gene and promoter of pM3,130-7 (disclosed in U.S. Pat. No. 5,055,294) into a pTJS260-based vector such as pMYC467 (disclosed in U.S. Pat. No. 5,169,760) by methods well known in the art. In particular, the pM3,130-7 promoter and toxin gene can be obtained as a BamHI to NdeI fragment and placed into the pMYC467 plasmid replacing a fragment bounded by the same sites (BamHI near base 12100 and NdeI near base 8000).

The improved vector ideally contains a unique BamHI cloning site. The plasmid BamHI site, located upstream from the tac promoter (Ptac), can be removed by blunting with Klenow and religating (FIG. 1). Absence of the site can be confirmed by restriction digestion. A plasmid produced according to this procedure was called pMYC1050ΔBamHI. The construct can now have a BamHI site added to the plasmid by SOE mutagenesis. SOE mutagenesis can be facilitated by subcloning an NsiI toxin-containing DNA fragment into the smaller pGEM5 (Promega Corp., Madison, Wis.) vector which uses the ampicillin resistance (bla) gene as a selectable marker (FIG. 1). The fragment can be oriented by restriction digestion. A plasmid produced according to this procedure was called pGEMtox.

Figure 2:
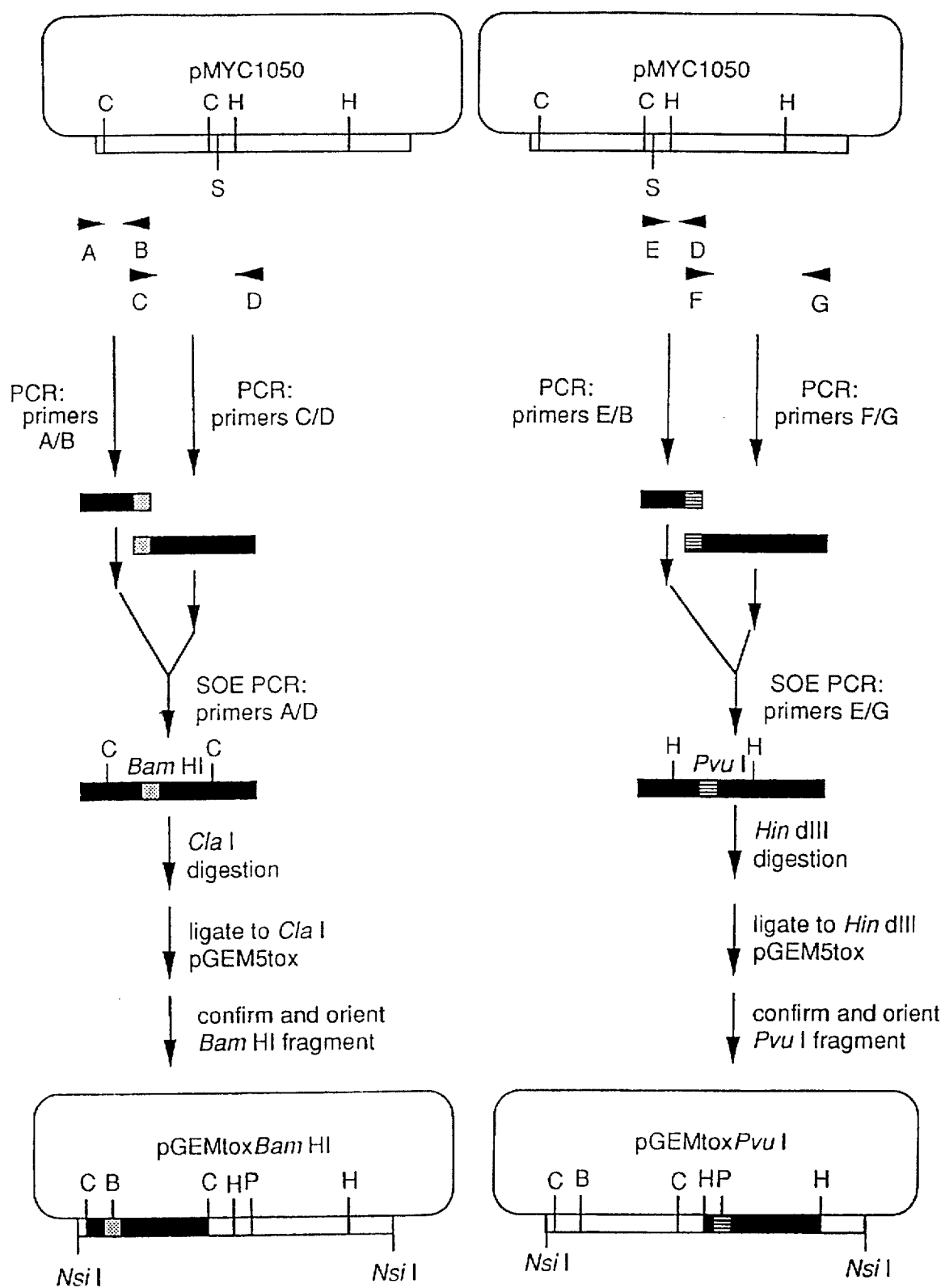
FIG. 2—BamHI or PvuI cloning sites were introduced into toxin DNA by the technique of Splice Overlap Extension (SOE). DNA fragments with the new sites are used to replace homologous DNA fragments in pGEMtox. The resulting plasmids are pGEMtoxBamHI or pGEMtoxPvuI. The letters A through G below the arrows correspond to oligonucleotide primers in the text. Letters above vertical lines correspond to restriction enzyme sites. B=BamHI, C=ClaI, H=HindIII, P=PvuI, S=SacI.

DNA in the toxin coding region can be mutated by the PCR-mediated technique of SOE to introduce restriction enzyme cloning sites as shown in FIG. 2. Oligonucleotides useful as primers are shown below:

"A" (SEQ ID NO. 1)
5' GCATACTAGTAGGAGATTTCCATG-GATAACAATCCGAAC 3'

"B" (SEQ ID NO. 2)
5' GGATCCGCFTCCCAGTCT 3'

"C" (SEQ ID NO. 3)
5' AGAGAGTGGGAAGCGGATCCTACTAATCC 3'

"D" (SEQ ID NO. 4)
5' TGGATACTCGATCGATATGATAATCCGT 3'

"E" (SEQ ID NO. 5)
5' TAATAAGAGCTCCTATGT 3'

"F" (SEQ ID NO. 6)
5' TATCATATCGATCGAGTATCCAATTTAG 3'

"G" (SEQ ID NO. 7)
5' GTCACATAGCCAGCTGGT 3' pMYC1050 DNA was used as the template for PCR amplification using primer sets A/B, C/D, E/D, and F/G. Amplified DNA fragments were named AB, CD, ED, and FG. Amplified DNAs were purified by agarose-TBE gel electrophoresis, electroelution, and NACS column chromatography, methods all well-known in the art. Purified template DNAs were used in a second set of PCR reactions. Fragments AB and CD were mixed and amplified with primers A and D. In a separate reaction, fragments ED and FG were mixed and amplified with primers E and G. Amplified DNA was resolved by agarose-TBE gel electrophoresis and the fragments with the corresponding increase in size were excised, electroeluted, and purified over NACS columns by means well known in the art. Amplified DNA fragments are called AD or EG for reference.

DNA fragments AD or EG with the new restriction enzyme sites were incorporated into the toxin-containing DNA by several subcloning procedures (FIGS. 2 and 3). pGEMtox was digested with ClaI or HindIII. Vector-containing DNA was gel-purified. Fragment AD was digested with ClaI and ligated to ClaI-digested pGEMtox vector DNA. Fragment EG was digested with HindIII and ligated to HindIII-digested pGEMtox vector DNA. *E. coli* strain NM522 was transformed with ligation mixes. Correctly assembled constructs were identified by restriction enzyme digestion of plasmid DNA from isolated colonies. The plasmid with the new BamHI site was called pGEMtox BamHI. The plasmid with the new PvuI site was called pGEMtox PvuI. The ClaI fragment containing the BamHI site from plasmid pGEMtox BamHI was ligated to the phosphatased ClaI vector-containing fragment from pGEMtox PvuI. *E. coli* strain NM522 was transformed with ligation mixes. Correctly assembled constructs were identified by PCR analysis with primer set C/D, and by restriction digestion. The plasmid with both new restriction enzyme sites was called pGEMtox BamHI/PvuI.

Figure 3:
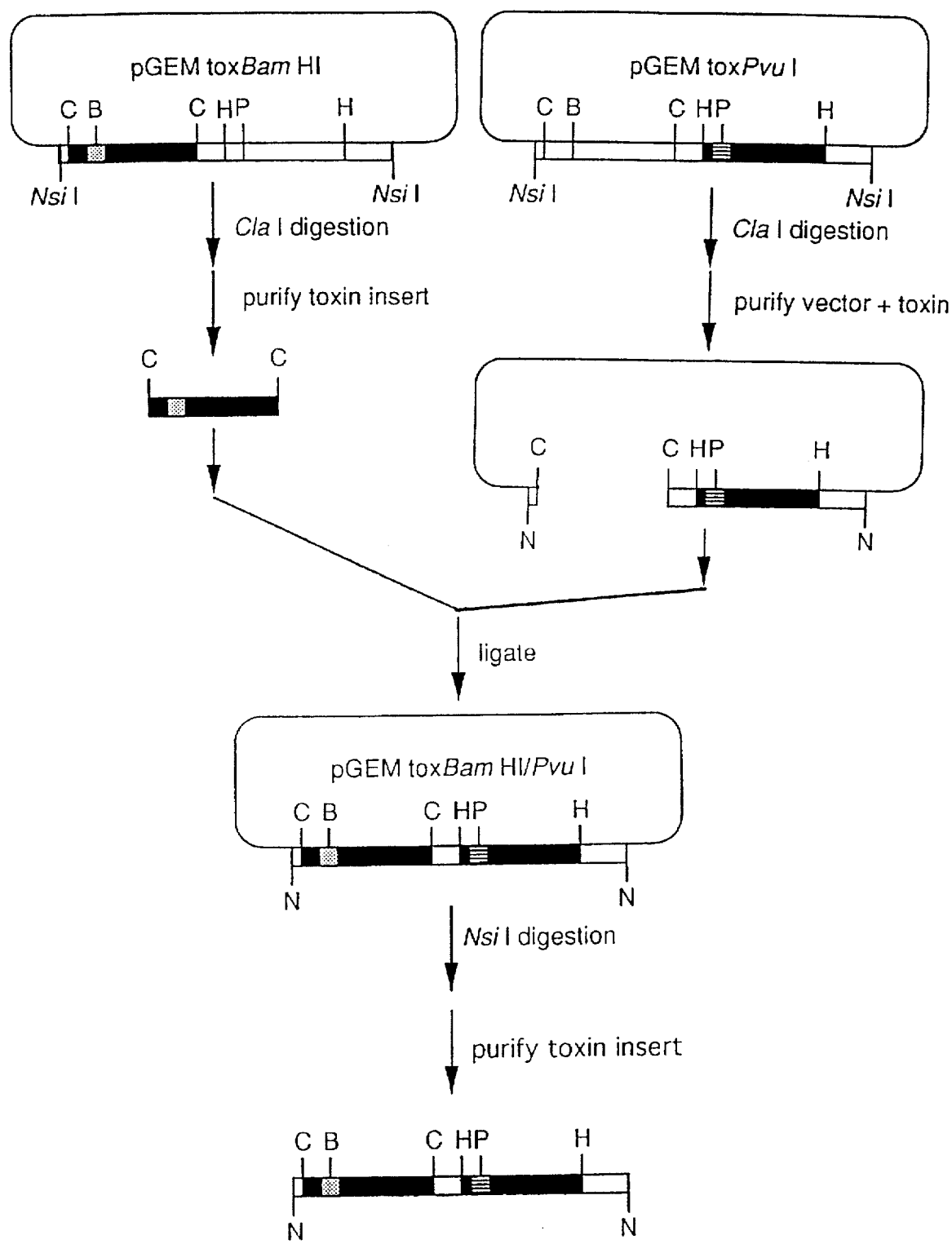
FIG. 3—The DNA fragment containing the BamHI mutation is used to replace the homologous fragment in pGEMtoxPvuI. The resulting plasmid which contains both cloning sites is pGEMtoxBamHI/PvuI. To construct an expression plasmid, the toxin-containing NsiI fragment is excised for cloning into the pTJS260 broad host-range vector. B=BamHI, C=ClaI, H=HindIII, P=PvuI.
Figure 4:
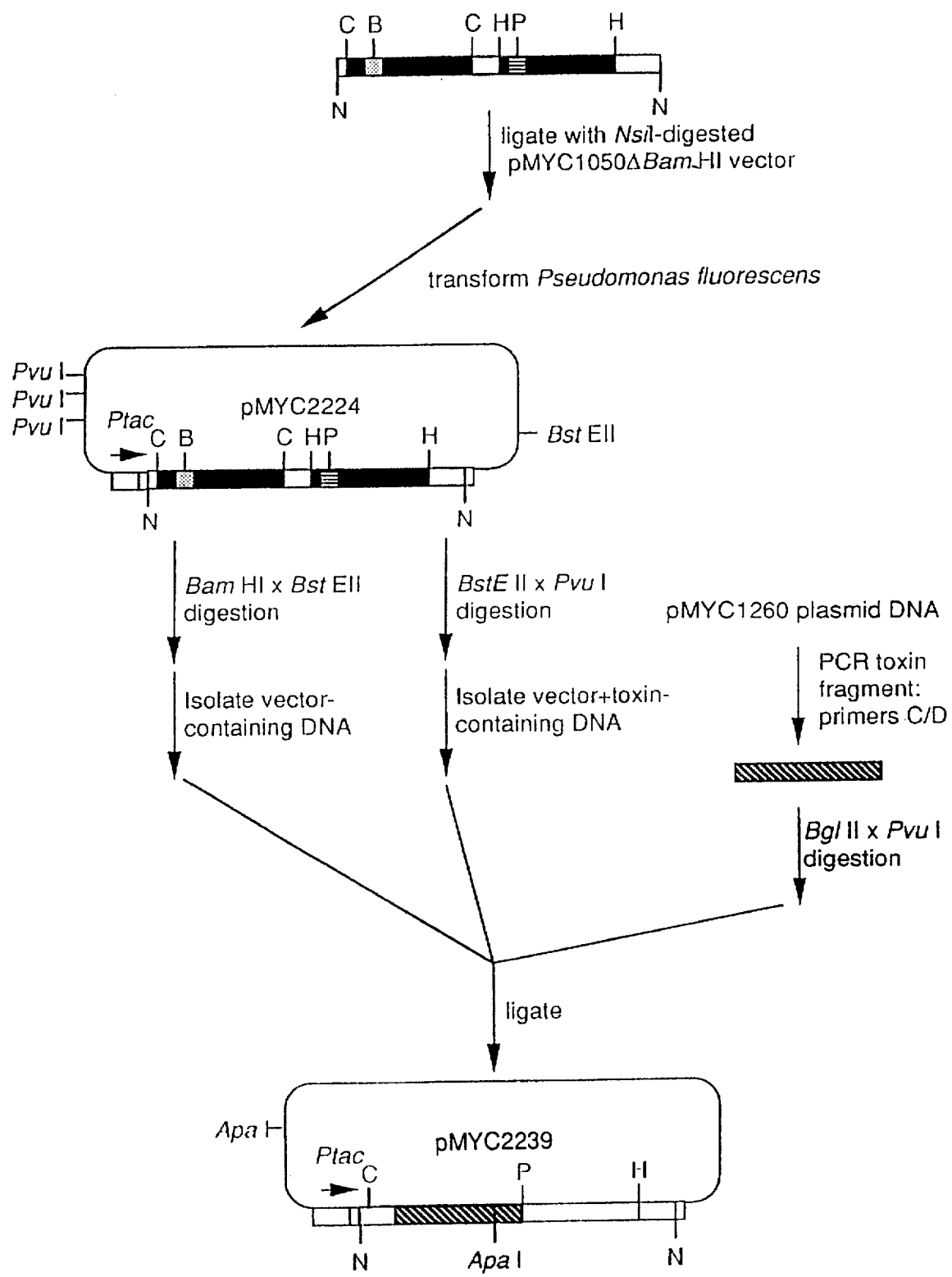
FIG. 4—The NsiI toxin-containing fragment with the new restriction sites is ligated to the vector-containing DNA from pMYC1050ΔBamHI to give pMYC2224. A BamHI-PvuI PCR-derived DNA fragment containing the cryIF toxin is exchanged for the equivalent fragment in pMYC2224. The resulting chimera is called pMYC2239. B=BamHI, C=ClaI, H=HindIII, N=NsiI, P=PvuI.
Figure 5:
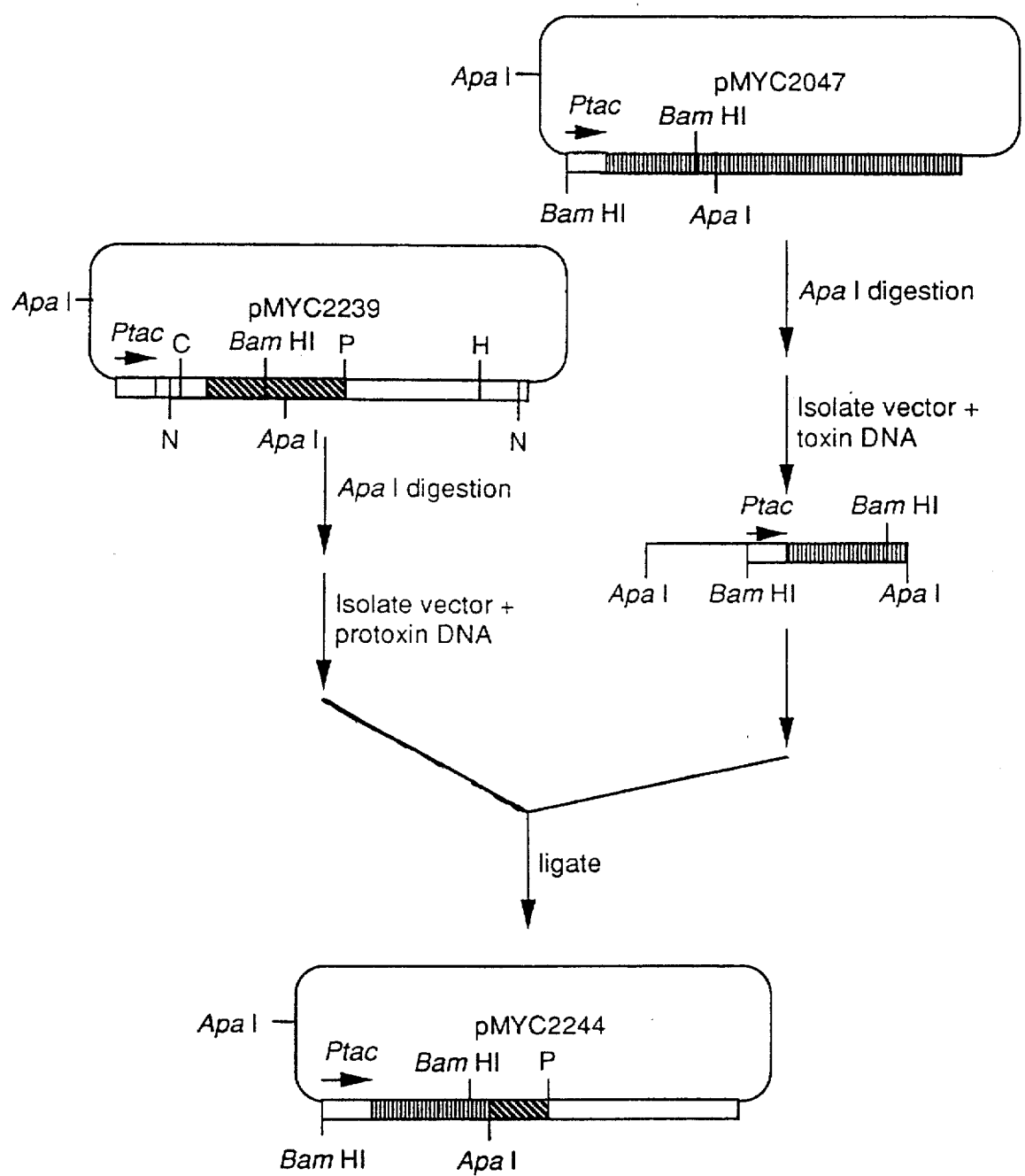
FIG. 5—The small ApaI DNA fragment of pMYC2047 is substituted for the homologous region of pMYC2239 to give plasmid pMYC2244. This chimera consists of cryIF in the toxin region and cryIA(b) in the protoxin. C=ClaI, H=HindIII, N=NsiI, P=PvuI.

A completed expression vector was assembled with insert from pGEMtox BamHI/PvuI and vector from pMYC1050ΔABamHI (FIGS. 3 and 4). Gel-purified insert was prepared from pGEMtoxBamHI/PvuI by NsiI digestion, and ScaI digestion (to remove contaminating vector). It was ligated to gel-purified NsiI-digested vector-containing pMYC1050ΔBamHI DNA. *E. coli* strain NM522 was transformed with the ligation mixes, and transformation mixes were plated on LB agar containing tetracycline at 12 μg/ml. Colonies containing the NsiI insert were identified by colony hybridization and autoradiography. Inserts were oriented by PCR, using primer set A/D, which bridges an NsiI cloning site, and agarose-TBE gel electrophoresis. The correctly assembled plasmid is called pMYC2224. DNA and protein sequences of the toxin are found in SEQ ID NOS. 18 and 19, respectively. A lactose-inducible *P. fluorescens* strain was electroporated with correctly assembled plasmid DNA. Transformation mixes were plated on LB agar containing tetracycline at 20 μg/ml. Plasmid DNA was prepared from *P. fluorescens* for use in subsequent cloning experiments.

EXAMPLE 2

Subcloning the cryIF Hypervariable Region into pMYC2224

A DNA fragment containing the hypervariable region from cryIF (pMYC1260) was exchanged for the BamHI-PvuI toxin-containing DNA fragment from pMYC2224 (FIG. 4). Since the coding sequence contains a preexisting BamHI site, BglII was chosen for cloning. The 4-base overhangs of BamHI and BglII are compatible, permitting ligation while eliminating both sites from the junction. It was necessary to synthesize a new primer for PCR:

"L" (SEQ ID NO. 8)

5' GAGTGGGAAGCAGATCTFAATAATGCACAATFAAGG 3'

A toxin-containing DNA fragment was generated by PCR with primers L/D on template pMYC1260. The DNA was digested with BglII and PvuI for subcloning. Since the tetAR locus contains multiple PvuI sites, it was necessary to isolate the vector-containing DNA on two separate fragments. To obtain the first fragment, pMYC2224 was digested with BamHI×BstEII, and the large DNA fragment containing the Ptac-tetAR locus-rep functions was gel-purified. To obtain the second fragment, pMYC2224 was digested with BstEII×PvuI, and the DNA fragment containing the vector-protoxin module was gel-purified. A three-piece ligation was set up and used for *E. coli* strain NM522 transformation. Grossly correct plasmids were identified by PCR analysis and agarose-TBE gel electrophoresis using the primer set N/O, which bridges the BamHI/BglII fusion junction.

"N" (tac promoter) (SEQ ID NO. 9)

5' TTAATCATCGGCTCGTA 3'

"O" (SEQ ID NO. 10)

5' ACTCGATCGATATGATA(GA)TCCGT 3'

The correct plasmid was named pMYC2239. It consists of cryIA(c) at the amino-terminus, cryIF up to the toxin/protoxin junction, and cryIA(b) through the protoxin segment. The toxin DNA and protein sequences are in SEQ ID NOS. 20 and 21, respectively.

EXAMPLE 3

Construction of the *P. fluorescens* Expression Plasmids pMYC1260 and pMYC2047

The cloned toxin gene cryIF can be modified for expression in *P. fluorescens* in the following way:

1. A plasmid containing the pKK223-3 rrnB termination sequences in the pTJS260-derived vector (Dr. Donald Helinski, U.C. San Diego) can be made by ligating the BamHI-ScaI fragment containing the Ptac promoter and rnnB terminator from pKK223-3 (Pharmacia *E. coli* vector) into the BamHI to blunted KpnI vector fragment of pMYC1197 (described in EP 0 417 564). The assembled plasmid is recovered following transformation of *E. coli* and growth under tetracycline selection.

2. A plasmid containing the Ptac-promoted cryIF toxin gene can be made by ligating toxin gene-containing NdeI-Nde-I fragment (with ends blunted using DNA polymerase and dNTPs) of about 3800 bp from pMYC1603 (from NRRL B-18517) into the blunted EcoRI and HindIII sites of pKK223-3. The Ptac-promoted cryIF toxin plasmid can be recovered following transformation of *E. coli*, grown under ampicillin selection, and screening for plasmids with inserts in the proper orientation for expression from the Ptac promoter by techniques well known in the art.

3. The Ptac-promoted cryIF toxin can be assembled into the pTJS260derived vector in a three-piece ligation using the 2.4 kb DNA fragment having BamHI and ApaI ends from the plasmid pTJS260, ApaI to HindIII fragment of 8.5 kb containing the replication region of the plasmid from step 1 above, and a HindIII to partial BamHI fragment containing the Ptac promoter and cryIF toxin gene from step 2 above.

The resulting pTJS260-derived cryIF toxin expression plasmid (pMYC1260) can be introduced into *P. fluorescens* by electroporation.

4. pMYC2047 can be constructed by ligating an SpeI to KpnI fragment obtained through PCR of a suitable cryIF template with primers H and K followed by digestion with SpeI and KpnI and gel purification, an ApaI to KpnI fragment of ca. 10 kb from the plasmid of step 3, and the ApaI to SpeI fragment of ca. 2600 bp from pMYC1197 containing the Ptac promoter. The correct cryIF toxin expression plasmids are determined by restriction enzyme digestion of plasmids following electroporation into *Pseudomonas fluorescens*.

EXAMPLE 4

Construction of a cryIF/cryIA(b) Chimera

The cryIA(c) segment at the amino-terminus can be replaced by the cryIF coding sequence by a simple, straightforward swap (FIG. 5). Both the tetAR locus and cryIF coding sequence contain an ApaI site. A small ApaI fragment containing a portion of the tetAR genes and the amino-terminus of cryIF can be isolated from pMYC2047 and ligated to the large ApaI vector-containing fragment from pMYC2239. A *P. fluorescens* lactose-inducible strain can be electroporated with the ligation mix and plated on LB agar containing tetracycline at 20 μg/ml. Lactose-inducible strains are known to those skilled in the art and are described, for example, in U.S. Pat. No. 5,169,760. Correct orientation of the ApaI fragment reconstitutes tetracycline resistance. A clone produced in this manner was shown to be grossly correct by restriction enzyme digestion, and it was named pMYC2244. The toxin DNA sequence is shown in SEQ ID NO. 22, and the predicted protein sequence is shown in SEQ ID NO. 23.

EXAMPLE 5

Construction of a Limited Codon Rework of cryIF

Figure 6:
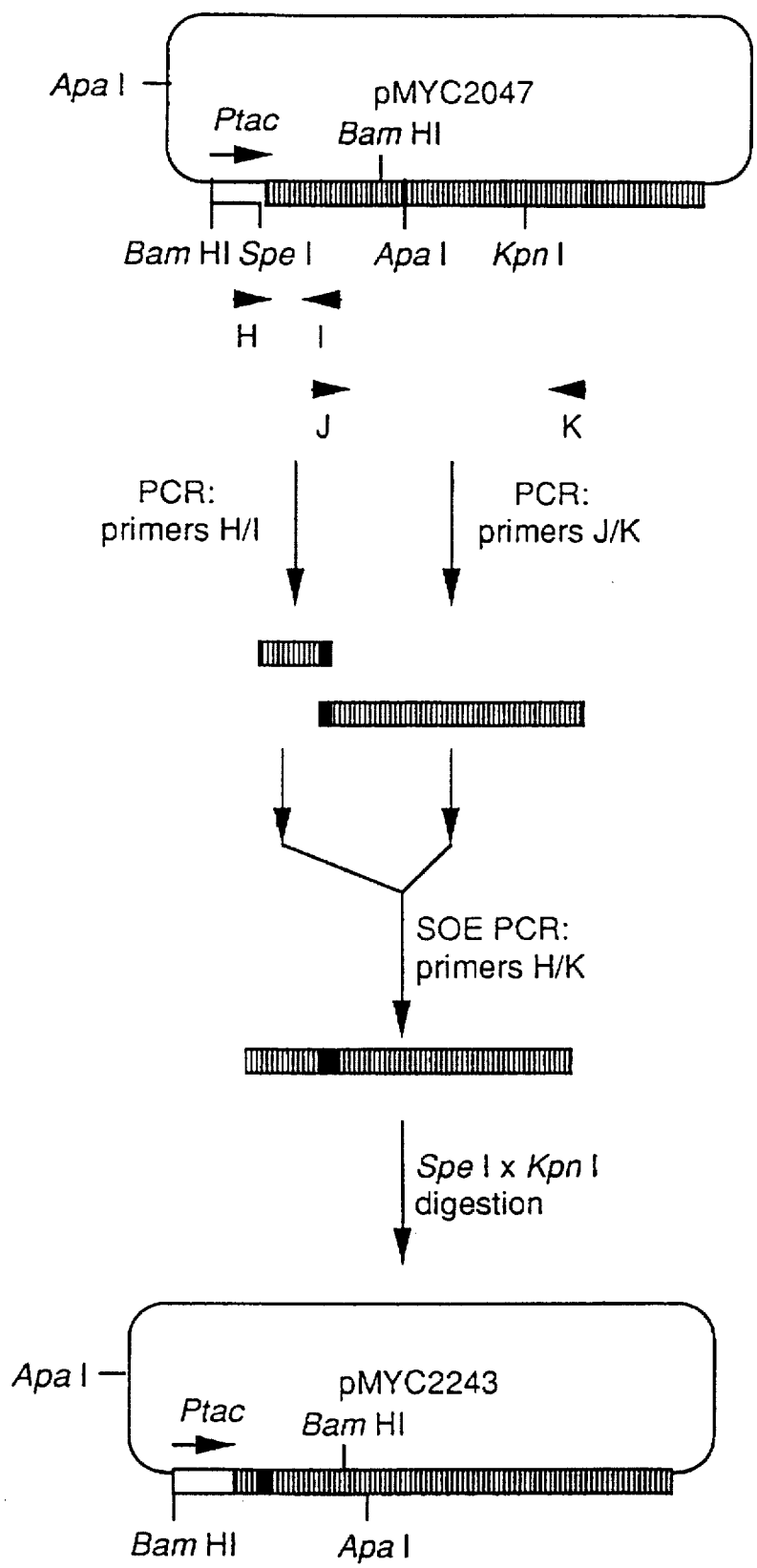
FIG. 6—Silent codon changes are introduced into the cryIF toxin by SOE. The SpeI-KpnI PCR DNA fragment with the changes is substituted for the homologous toxin-containing fragment in pMYC2047. The resulting plasmid is pMYC2243. Letters H through K below the arrows correspond to oligonucleotide primers in the text.
Figure 7:
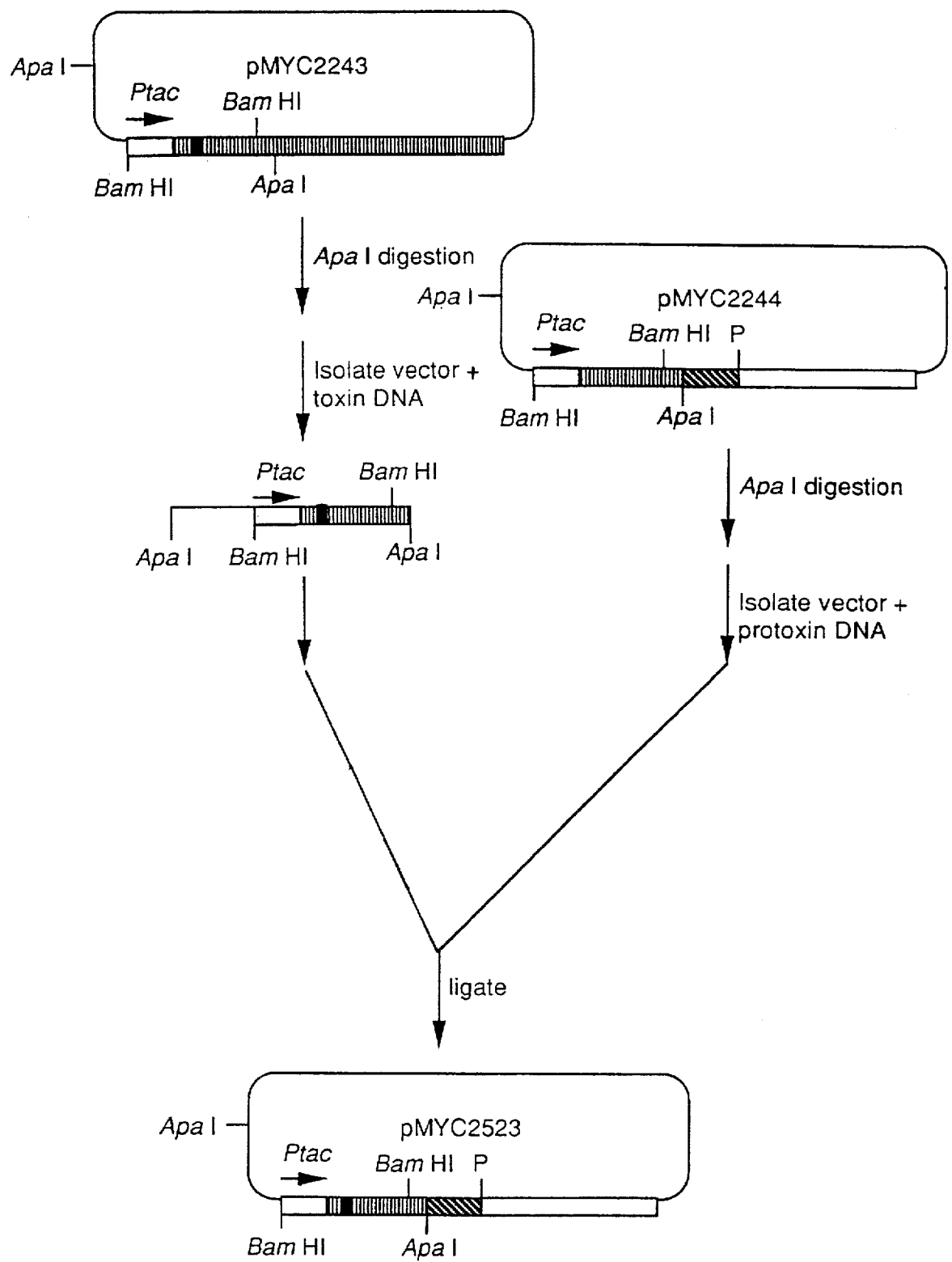
FIG. 7—Silent codon changes are introduced into pMYC2244 by substitution of the homologous fragment with the small ApaI DNA fragment of pMYC2243. The final plasmid is pMYC2523. P=PvuI.

Codon usage in Pseudomonas spp. favors G or C in the wobble position of triplet codons, as determined by analysis of genes in the GenBank/EMBL sequence libraries. A limited region of the cryIF gene was reworked by SOE to incorporate favored wobble position changes that were silent (FIG. 6). Oligos used are shown below:

"H" (SEQ ID NO. 11)
5' GGACTAGTAAAAAGGAGATAACCATG-GAAAATAATATTCAAAATC 3'

"I" (SEQ ID NO. 12)
5' TCCAGCGGCAGGCGGCCGGTGCTGCGT-TCTFCGTTCAGTATTTCTACT TCAGGATTATT-TAAAC 3'

"J" (SEQ ID NO. 13)
5' AACGCAGCACCGGCCGCCTGCCGCTGGA-CATCAGCCTGAGCCITACAC GTTTCCTTTTGAGT-GAA 3'

"K" (SEQ ID NO. 14)
5' CATCAAAGGTACCTGGT 3'

Two separate PCR reactions were done on pMYC2047 template with primer sets H/I or J/K. Amplified DNA fragments were called HI or JK. A second PCR reaction was set up by mixing fragments HI and JK and PCR amplifying with primer set H/K. The larger SOE DNA was gel-purified and digested with SpeIxKpnI. A three-piece ligation was set up with SpeI-ApaI Ptac-tetAR locus DNA, ApaI-KpnI vector-protoxin module DNA, and SpeI-KpnI PCR DNA. A *P. fluorescens* lactose-inducible strain can be electroporated with the ligation mix. Grossly correct clones can be identified by PCR analysis using the primer set P/Q and agarose-TBE gel electrophoresis. Oligo P (SEQ ID NO. 15) was designed to discriminate between the wild-type and codon-reworked gene.

"P" (SEQ ID NO. 15)
5' TGCCGCTGGACATCAGCCTGAG 3'

"Q" (SEQ ID NO. 16)
5' TCTAGAGCGGCCGCITATAC(CT)CGATC-GATATGATA(GA)TCCGT 3'

The complete plasmid was named pMYC2243. The toxin DNA sequence is shown in SEQ ID NO. 24. The toxin protein sequence is predicted to be unchanged, and is shown in SEQ ID NO. 25.

EXAMPLE 6

Construction of the cryIF/cryIA(b) Chimera Containing the Limited Codon Rework

The construct was assembled (FIG. 7) using the same ApaI fragment exchange strategy as for pMYC2244 (cryIF/cryIA(b)) above. The small, toxin-tetAR locus ApaI DNA fragment was gel-purified from pMYC2243. The larger vector-protoxin module ApaI DNA fragment was gel-purified from pMYC2244. The completed plasmid was named pMYC2523. Predicted DNA and protein sequences are in SEQ ID NOS. 26 and 27, respectively.

EXAMPLE 7

Comparative Expression of Toxins from pMYC2243 and pMYC2523

Toxin expression in *P. fluorescens* was analyzed as described above. At 24 and 48 hours post-induction, the pMYC2523-containing strain produced more toxin than the pMYC2243-containing strain. Toxin specific activity on *Spodoptera exigua* was statistically unchanged.

EXAMPLE 8

Construction of the cryIF/436 Chimera Containing the Limited Codon Rework

Figure 8:
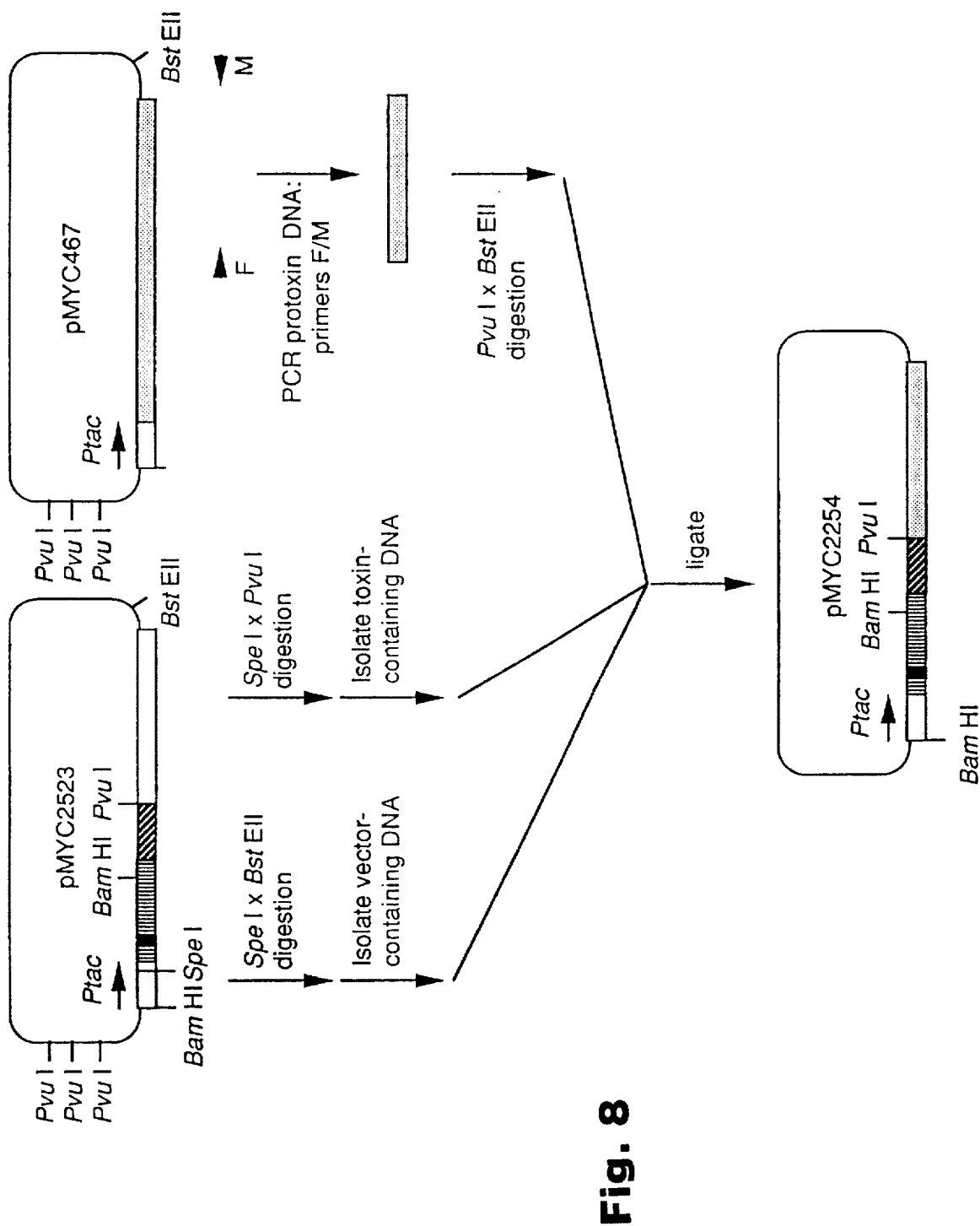
FIG. 8—A chimeric toxin containing the 436 protoxin is constructed by substituting a PCR-generated PvuI-BstEII protoxin DNA for the homologous fragment in pMYC2523. The final plasmid is pMYC2254. Letters F and M below the arrows correspond to oligonucleotide primers in the text.

A second type of chimeric toxin was assembled by substituting the 436 protoxin module for the cryIA(b) protoxin in pMYC2523 (FIG. 8). The 436 protoxin sequence consists of cryIA(c) sequence except at the very C-terminus (See U.S. Pat. Nos. 5,128,130 and 5,169,760, incorporated herein by reference in their entirety). Protoxin DNA for cloning was generated by PCR with the primer set F/M using a plasmid such as pMYC467 (U.S. Pat. No. 5,169,760) as a template.

"M" (SEQ ID NO. 17)
5' AGGCTTCCATAGATACCTTGTGCG 3'

PCR DNA was digested with PvuIxBstEII. A three-piece ligation was set up with SpeI-PvuI toxin DNA from pMYC2523, SpeI-BstEII vector DNA from pMYC2523, and PvuI-BstEII PCR protoxin module DNA. A lactose-inducible *P. fluorescens* strain was electroporated with the ligation mix. Grossly correct plasmids were identified by PCR with primer set F/G and screening for slight size increase by agarose-TBE gel electrophoresis. The construct was named pMYC2254. Predicted DNA and protein sequences are found in SEQ ID NOS. 28 and 29, respectively.

EXAMPLE 9

Comparative Expression of Toxins from pMYC2243 and pMYC23254

Toxic expression in *P. fluorescens* was analyzed as described above. Toxin expression from pMYC2254 was improved over pMYC2243 expression.

EXAMPLE 10

Insertion of the Gene Encoding the Chimeric Toxin Into Plants

One aspect of the subject invention is the transformation of plants with genes encoding the insecticidal toxin. The transformed plants are resistant to attack by the target pest.

The gene encoding the chimeric toxin, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the *B.t.* toxin can be inserted into the vector at a suitable

19 restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 0 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are flamed by the right and left T-DNA border regions. They can be transformed directly into agrobacteria (Holsters et al. [1978] *Mol. Gen. Genet.* 163:181–187). The agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed traits to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. Also, advantageously, plants encoding a truncated toxin will be used. The truncated toxin typically will encode about 55% to about 80% of the full length toxin. Methods for creating synthetic genes for use in plants are known in the art.

EXAMPLE 11

Cloning of the Gene Encoding the Chimeric Toxin Into Insect Viruses

A number of viruses are known to infect insects. These viruses include, for example, baculoviruses and entomopoxviruses. In one embodiment of the subject invention, genes encoding the insecticidal toxins, as described herein, can be placed within the genome of the insect virus, thus enhancing the pathogenicity of the virus. Methods for constructing insect viruses which comprise the chimeric toxin gene are well known and readily practiced by those skilled in the art. These procedures are described, for example, in Merryweather et al. (Merryweather, A. T., U. Weyer, M. P. G. Harris, M. Hirst, T. Booth, R. D. Possee (1990) *J. Gen. Virol.* 71:1535–1544) and Martens et al. (Martens, J. W. M., G. Honee, D. Zuidema, J. W. M. van Lent, B. Visser, J. M. Vlak (1990) *Appl. Environmental Microbid.* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. An isolated polynucleotide molecule comprising a nucleotide sequence encoding a Bacillus thuringiensis toxin wherein said Bacillus thuringiensis toxin is a chimeric toxin comprising a cryIF core N-terminal toxin portion and a heterologous protoxin portion from a cryIA(b) or a cryIA(c)/cryIA(b) chimeric toxin.

2. The isolated polynucleotide molecule, according to claim 1, comprising a nucleotide sequence encoding a chimeric Bacillus thuringiensis toxin of approximately 1150 to 1200 amino acids, wherein said toxin comprises a cryIF core N-terminal sequence of at least about 590 amino acids and no more than about 1100 amino acids, and wherein said cryIA(b) or cryIA(c)/cryIA(b) protoxin portion comprises at least 100 amino acids at the C-terminus of said toxin.

3. The isolated polynucleotide molecule, according to claim 2, wherein the transition from cryIF core N-terminal toxin portion to heterologous protoxin portion occurs after the sequence shown in SEQ ID NO. 30 and before the end of the peptide sequence of SEQ ID NO. 31.

4. The isolated polynucleotide molecule, according to claim 3, wherein said core toxin portion comprises the first about 601 amino acids of a cryIF toxin and wherein said heterologous protoxin portion comprises the cryIA(b) or cryIA(c)/cryIA(b) amino acid sequence which follows the peptide sequence shown in SEQ ID NO. 31.

5. The isolated polynucleotide molecule, according to claim 1, comprising a nucleotide sequence encoding a toxin having the amino acid sequence of SEQ ID. NO. 23.

6. The isolated polynucleotide molecule, according to claim 5, comprising the nucleotide sequence of SEQ ID NO. 22.

7. The isolated polynucleotide molecule, according to claim 1, comprising a nucleotide sequence encoding a toxin having the amino acid sequence of SEQ ID. NO. 29.

8. The isolated polynucleotide molecule, according to claim 7, comprising the nucleotide sequence of SEQ ID NO. 28.

9. The isolated polynucleotide molecule, according to claim 1, wherein said gene has been modified so as to utilize a higher percentage of codons which are favored by Pseudomonads.

10. The isolated polynucleotide molecule, according to claim 9, wherein said Pseudomonad is transformed with a polynucleotide sequence comprising DNA which encodes the amino acid sequence of SEQ ID NO. 27.

11. The isolated polynucleotide molecule, according to claim 10, wherein said DNA consists essentially of the sequence of SEQ ID NO. 26.

12. The isolated polynucleotide molecule, according to claim 1, which encodes an amino acid sequence of FIG. 9.

13. A DNA transfer vector comprising the polynucleotide of claim 1.

14. A Pseudomonad transformed to comprise the polynucleotide of claim 1 such that the toxin encoded thereby is expressed.

15. A substantially pure chimeric Bacillus thuringiensis toxin comprising a cryIF core N-terminal toxin portion and a heterologous C-terminal protoxin portion from a cryIA(b) toxin or cryIA(b)/cryIA(c) chimeric toxin.

16. The chimeric Bacillus thuringiensis toxin, according to claim 15, having approximately 1150 to 1200 amino acids, wherein said toxin comprises a cryIF core N-terminal sequence of at least about 590 amino acids and no more than about 1100 amino acids, wherein said cryIA(b) or cryIA(c)/cryIA(b) protoxin portion comprises at least 100 amino acids at the C-terminus of said toxin.

17. The chimeric *Bacillus thuringiensis* toxin, according to claim 16, wherein the transition from cryIF core N-terminal toxin portion to heterologous protoxin portion occurs after the sequence shown in SEQ ID NO. 30 and before the end of the peptide sequence of SEQ ID NO. 31.

18. The chimeric *Bacillus thuringiensis* toxin, according to claim 17, wherein said core toxin portion comprises the first about 601 amino acids of a cryIF toxin and wherein said C-terminal protoxin portion comprises the cryIA(b) or cryIA(c)/cryIA(b) amino acid sequence which follows the peptide sequence shown in SEQ ID NO. 31.

19. The toxin, according to claim 15, wherein said toxin comprises the amino acid sequence shown in SEQ ID NO. 23.

20. The toxin, according to claim 15, wherein said toxin comprises the amino acid sequence shown in SEQ ID NO. 29.

21. The chimeric *Bacillus thuringiensis* toxin, according to claim 15, comprises an amino acid sequence shown in FIG. 9.

* * * * *

UNITED STATES PATENT AND TRADEMARK OFFICE
CERTIFICATE OF CORRECTION

PATENT NO. : 5,527,883
DATED : June 18, 1996
INVENTOR(S) : Mark Thompson, et al

Page 1 of 2

It is certified that error appears in the above-indentified patent and that said Letters Patent is hereby corrected as shown below:

Column 2: Line 31: "Carey.," should read --Carey,--.
Column 5: Line 60: "acryIA(c)" should read --a cryIA(c)--.
Column 6: Line 37: "o:15" should read --of--; Line 60: "Ash" should read --Asn--.
Column 10: Line 27: "SerraHa," should read --Serratia,--; Line 40: "diffiuens," should read --diffluens,--.
Column 11: Line 18: "Hetty's" should read --Helly's--.
Column 12: Line 59: "Pseudornonas" should read --Pseudomonas--.
Column 14: Line 30: "5'GGATCCGCFTCCCAGTCT 3'" should read --5'GGATCCGCTTCCCAGTCT 3'--.
Column 15: Line 13: "pMYC1050ΔABamHI" should read --pMYC1050ΔBamHI--; Lines 46-47: "5'GAGTGGGAAGCAGATCTFAATAATGCACAATFAAGG 3'" should read --5'GAGTGGGAAGCAGATCTTAATAATGCACAATTAAGG 3'--.
Column 16: Line 17: "rmB" should read --rrnB--; Line 34: "pTJS260derived" should read --pTJS260-derived--.
Column 17: Line 25: "5'TCCAGCGGCAGGCGGCCGGTGCTGCGTTCTFCG...3'" should read --5'TCCAGCGGCAGGCGGCCGGTGCTGCGTTCTTCG...3'--; Line 29: "5'AACGCAGCACCGGCCGCCTGCCGCTGGACATCAGCC-TGA- GCCL...3'" should read --5'AACGCAGCACCGGCCGCCTGCCGCTGGACATCAGCCTGAGCCT...3'--; Line 50: "5'TCTAGAGCGGC-CGCL...3'" should read --5'TCTAGAGCGGCCGCT...3'--.

UNITED STATES PATENT AND TRADEMARK OFFICE
CERTIFICATE OF CORRECTION

PATENT NO.  : 5,527,883
DATED       : June 18, 1996
INVENTOR(S) : Mark Thompson, et al It is certified that error appears in the above-indentified patent and that said Letters Patent is hereby corrected as shown below:

Column 18: Line 45: "pMYC2243 and pMYC23254" should read --pMYC2243 and pMYC2254--.
Column 19: Line 50: "flamed" should read --framed--.
Column 20: Line 49: "Microbid." should read --Microbiol.--.

Signed and Sealed this

Tenth Day of December, 1996

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:

( A ) LENGTH: 39 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:1:

GCATACTAGT AGGAGATTTC CATGGATAAC AATCCGAAC 39

( 2 ) INFORMATION FOR SEQ ID NO:2:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

GGATCCGCTT CCCAGTCT 18

( 2 ) INFORMATION FOR SEQ ID NO:3:

( i ) SEQUENCE CHARACTERISTICS:
        ( A ) LENGTH: 29 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:3:

AGAGAGTGGG AAGCGGATCC TACTAATCC 29

( 2 ) INFORMATION FOR SEQ ID NO:4:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:4:

TGGATACTCG ATCGATATGA TAATCCGT 28

( 2 ) INFORMATION FOR SEQ ID NO:5:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:5:

TAATAAGAGC TCCTATGT 18

( 2 ) INFORMATION FOR SEQ ID NO:6:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:6:

TATCATATCG ATCGAGTATC CAATTTAG 28

( 2 ) INFORMATION FOR SEQ ID NO:7:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:7:

GTCACATAGC CAGCTGGT 18

( 2 ) INFORMATION FOR SEQ ID NO:8:

( i ) SEQUENCE CHARACTERISTICS:
        ( A ) LENGTH: 36 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:8:

GAGTGGGAAG CAGATCTTAA TAATGCACAA TTAAGG 36

( 2 ) INFORMATION FOR SEQ ID NO:9:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:9:

TTAATCATCG GCTCGTA 17

( 2 ) INFORMATION FOR SEQ ID NO:10:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:10:

ACTCGATCGA TATGATARTC CGT 23

( 2 ) INFORMATION FOR SEQ ID NO:11:

( i ) SEQUENCE CHARACTERISTICS:
        ( A ) LENGTH: 45 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:11:

GGACTAGTAA AAAGGAGATA ACCATGGAAA ATAATATTCA AAATC 45

( 2 ) INFORMATION FOR SEQ ID NO:12:

( i ) SEQUENCE CHARACTERISTICS:
        ( A ) LENGTH: 64 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:12:

```
TCCAGCGGCA GGCGGCCGGT GCTGCGTTCT TCGTTCAGTA TTTCTACTTC AGGATTATTT      60
AAAC                                                                  64
```

( 2 ) INFORMATION FOR SEQ ID NO:13:

( i ) SEQUENCE CHARACTERISTICS:
        ( A ) LENGTH: 65 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:13:

```
AACGCAGCAC CGGCCGCCTG CCGCTGGACA TCAGCCTGAG CCTTACACGT TTCCTTTTGA      60
GTGAA                                                                 65
```

( 2 ) INFORMATION FOR SEQ ID NO:14:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:14:

```
CATCAAAGGT ACCTGGT                                                    17
```

( 2 ) INFORMATION FOR SEQ ID NO:15:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:15:

```
TGCCGCTGGA CATCAGCCTG AG                                              22
```

( 2 ) INFORMATION FOR SEQ ID NO:16:

( i ) SEQUENCE CHARACTERISTICS:
        ( A ) LENGTH: 41 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:16:

```
TCTAGAGCGG CCGCTTATAC YCGATCGATA TGATARTCCG T                         41
```

( 2 ) INFORMATION FOR SEQ ID NO:17:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:17:

```
AGGCTTCCAT AGATACCTTG TGCG                                          24
```

( 2 ) INFORMATION FOR SEQ ID NO:18:

( i ) SEQUENCE CHARACTERISTICS:
        ( A ) LENGTH: 3465 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

```
ATGGATAACA ATCCGAACAT CAATGAATGC ATTCCTTATA ATTGTTTAAG TAACCCTGAA     60
GTAGAAGTAT TAGGTGGAGA AAGAATAGAA ACTGGTTACA CCCCAATCGA TATTTCCTTG    120
TCGCTAACGC AATTTCTTTT GAGTGAATTT GTTCCCGGTG CTGGATTTGT GTTAGGACTA    180
GTTGATATAA TATGGGGAAT TTTTGGTCCC TCTCAATGGG ACGCATTTCT TGTACAAATT    240
GAACAGTTAA TTAACCAAAG AATAGAAGAA TTCGCTAGGA ACCAAGCCAT TTCTAGATTA    300
GAAGGACTAA GCAATCTTTA TCAAATTTAC GCAGAATCTT TAGAGAGTG GAAGCGGAT     360
CCTACTAATC CAGCATTAAG AGAAGAGATG CGTATTCAAT TCAATGACAT GAACAGTGCC    420
CTTACAACCG CTATTCCTCT TTTTGCAGTT CAAAATTATC AAGTTCCTCT TTTATCAGTA    480
TATGTTCAAG CTGCAAATTT ACATTTATCA GTTTGAGAG ATGTTCAGT GTTTGGACAA     540
AGGTGGGGAT TTGATGCCGC GACTATCAAT AGTCGTTATA ATGATTTAAC TAGGCTTATT    600
GGCAACTATA CAGATTATGC TGTACGCTGG TACAATACGG GATTAGAACG TGTATGGGGA    660
CCGGATTCTA GAGATTGGGT AAGGTATAAT CAATTTAGAA GAGAATTAAC ACTAACTGTA    720
TTAGATATCG TTGCTCTGTT CCCGAATTAT GATAGTAGAA GATATCCAAT TCGAACAGTT    780
TCCCAATTAA CAAGAGAAAT TTATACAAAC CCAGTATTAG AAAATTTTGA TGGTAGTTTT    840
CGAGGCTCGG CTCAGGGCAT AGAAAGAAGT ATTAGGAGTC CACATTTGAT GGATATACTT    900
AACAGTATAA CCATCTATAC GGATGCTCAT AGGGGTTATT ATTATTGGTC AGGGCATCAA    960
ATAATGGCTT CTCCTGTAGG GTTTTCGGGG CCAGAATTCA CTTTTCCGCT ATATGGAACT   1020
ATGGGAAATG CAGCTCCACA ACAACGTATT GTTGCTCAAC TAGGTCAGGG CGTGTATAGA   1080
ACATTATCGT CCACTTTATA TAGAAGACCT TTTAATATAG GGATAAATAA TCAACAACTA   1140
TCTGTTCTTG ACGGGACAGA ATTTGCTTAT GGAACCTCCT CAAATTTGCC ATCCGCTGTA   1200
TACAGAAAAA GCGGAACGGT AGATTCGCTG GATGAAATAC CGCCACAGAA TAACAACGTG   1260
CCACCTAGGC AAGGATTTAG TCATCGATTA AGCCATGTTT CAATGTTTCG TTCAGGCTTT   1320
AGTAATAGTA GTGTAAGTAT AATAAGAGCT CCTATGTTCT CTTGGATACA TCGTAGTGCT   1380
GAATTTAATA ATATAATTCC TTCATCACAA ATTACACAAA TACCTTTAAC AAAATCTACT   1440
AATCTTGGCT CTGGAACTTC TGTCGTTAAA GGACCAGGAT TTACAGGAGG AGATATTCTT   1500
CGAAGAACTT CACCTGGCCA GATTTCAACC TTAAGAGTAA ATATTACTGC ACCATTATCA   1560
```

| | | | | | |
|---|---|---|---|---|---|
| CAAAGATATC | GGGTAAGAAT | TCGCTACGCT | TCTACCACAA | ATTTACAATT | CCATACATCA | 1620 |
| ATTGACGGAA | GACCTATTAA | TCAGGGGAAT | TTTTCAGCAA | CTATGAGTAG | TGGGAGTAAT | 1680 |
| TTACAGTCCG | GAAGCTTTAG | GACTGTAGGT | TTTACTACTC | CGTTTAACTT | TTCAAATGGA | 1740 |
| TCAAGTGTAT | TTACGTTAAG | TGCTCATGTC | TTCAATTCAG | GCAATGAAGT | TTATATAGAT | 1800 |
| CGAATTGAAT | TTGTTCCGGC | AGAAGTAACC | TTTGAGGCAG | AATATGATTT | AGAAAGAGCA | 1860 |
| CAAAAGGCGG | TGAATGAGCT | GTTTACTTCT | TCCAATCAAA | TCGGGTTAAA | AACAGATGTG | 1920 |
| ACGGATTATC | ATATCGATCG | AGTATCCAAT | TTAGTTGAGT | GTTTATCTGA | TGAATTTTGT | 1980 |
| CTGGATGAAA | AAAAAGAATT | GTCCGAGAAA | GTCAAACATG | CGAAGCGACT | TAGTGATGAG | 2040 |
| CGGAATTTAC | TTCAAGATCC | AAACTTTAGA | GGGATCAATA | GACAACTAGA | CCGTGGCTGG | 2100 |
| AGAGGAAGTA | CGGATATTAC | CATCCAAGGA | GGCGATGACG | TATTCAAAGA | GAATTACGTT | 2160 |
| ACGCTATTGG | GTACCTTTGA | TGAGTGCTAT | CCAACGTATT | TATATCAAAA | AATAGATGAG | 2220 |
| TCGAAATTAA | AAGCCTATAC | CCGTTACCAA | TTAAGAGGGT | ATATCGAAGA | TAGTCAAGAC | 2280 |
| TTAGAAATCT | ATTTAATTCG | CTACAATGCC | AAACACGAAA | CAGTAAATGT | GCCAGGTACG | 2340 |
| GGTTCCTTAT | GGCCGCTTTC | AGCCCCAAGT | CCAATCGGAA | AATGTGCCCA | TCATTCCCAT | 2400 |
| CATTTCTCCT | TGGACATTGA | TGTTGGATGT | ACAGACTTAA | ATGAGGACTT | AGGTGTATGG | 2460 |
| GTGATATTCA | AGATTAAGAC | GCAAGATGGC | CATGCAAGAC | TAGGAAATCT | AGAATTTCTC | 2520 |
| GAAGAGAAAC | CATTAGTAGG | AGAAGCACTA | GCTCGTGTGA | AAAGAGCGGA | GAAAAAATGG | 2580 |
| AGAGACAAAC | GTGAAAAATT | GGAATGGGAA | ACAAATATTG | TTTATAAAGA | GGCAAAAGAA | 2640 |
| TCTGTAGATG | CTTTATTTGT | AAACTCTCAA | TATGATAGAT | TACAAGCGGA | TACCAACATC | 2700 |
| GCGATGATTC | ATGCGGCAGA | TAAACGCGTT | CATAGCATTC | GAGAAGCTTA | TCTGCCTGAG | 2760 |
| CTGTCTGTGA | TTCCGGGTGT | CAATGCGGCT | ATTTTTGAAG | AATTAGAAGG | GCGTATTTTC | 2820 |
| ACTGCATTCT | CCCTATATGA | TGCGAGAAAT | GTCATTAAAA | ATGGTGATTT | TAATAATGGC | 2880 |
| TTATCCTGCT | GGAACGTGAA | AGGGCATGTA | GATGTAGAAG | AACAAAACAA | CCACCGTTCG | 2940 |
| GTCCTTGTTG | TTCCGGAATG | GGAAGCAGAA | GTGTCACAAG | AAGTTCGTGT | CTGTCCGGGT | 3000 |
| CGTGGCTATA | TCCTTCGTGT | CACAGCGTAC | AAGGAGGGAT | ATGGAGAAGG | TTGCGTAACC | 3060 |
| ATTCATGAGA | TCGAGAACAA | TACAGACGAA | CTGAAGTTTA | GCAACTGTGT | AGAAGAGGAA | 3120 |
| GTATATCCAA | ACAACACGGT | AACGTGTAAT | GATTATACTG | CGACTCAAGA | AGAATATGAG | 3180 |
| GGTACGTACA | CTTCTCGTAA | TCGAGGATAT | GACGGAGCCT | ATGAAAGCAA | TTCTTCTGTA | 3240 |
| CCAGCTGATT | ATGCATCAGC | CTATGAAGAA | AAAGCATATA | CAGATGGACG | AAGAGACAAT | 3300 |
| CCTTGTGAAT | CTAACAGAGG | ATATGGGGAT | TACACACCAC | TACCAGCTGG | CTATGTGACA | 3360 |
| AAAGAATTAG | AGTACTTCCC | AGAAACCGAT | AAGGTATGGA | TTGAGATCGG | AGAAACGGAA | 3420 |
| GGAACATTCA | TCGTGGACAG | CGTGGAATTA | CTTCTTATGG | AGGAA | | 3465 |

( 2 ) INFORMATION FOR SEQ ID NO:19:

( i ) SEQUENCE CHARACTERISTICS:
        ( A ) LENGTH: 1155 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:19:

```
Met  Asp  Asn  Asn  Pro  Asn  Ile  Asn  Glu  Cys  Ile  Pro  Tyr  Asn  Cys  Leu
 1                 5                    10                       15
```

| | | | | | | | | | | | | | | |
|---|---|---|---|---|---|---|---|---|---|---|---|---|---|---|
| Ser | Asn | Pro | Glu 20 | Val | Glu | Val | Leu 25 | Gly | Gly | Glu | Arg | Ile | Glu 30 | Thr | Gly |
| Tyr | Thr | Pro 35 | Ile | Asp | Ile | Ser | Leu 40 | Ser | Leu | Thr | Gln | Phe 45 | Leu | Leu | Ser |
| Glu | Phe 50 | Val | Pro | Gly | Ala 55 | Gly | Phe | Val | Leu | Gly 60 | Leu | Val | Asp | Ile | Ile |
| Trp 65 | Gly | Ile | Phe | Gly | Pro 70 | Ser | Gln | Trp | Asp 75 | Ala | Phe | Leu | Val | Gln | Ile 80 |
| Glu | Gln | Leu | Ile | Asn 85 | Gln | Arg | Ile | Glu | Glu 90 | Phe | Ala | Arg | Asn | Gln 95 | Ala |
| Ile | Ser | Arg | Leu 100 | Glu | Gly | Leu | Ser | Asn 105 | Leu | Tyr | Gln | Ile | Tyr 110 | Ala | Glu |
| Ser | Phe | Arg 115 | Glu | Trp | Glu | Ala | Asp 120 | Pro | Thr | Asn | Pro | Ala 125 | Leu | Arg | Glu |
| Glu | Met 130 | Arg | Ile | Gln | Phe | Asn 135 | Asp | Met | Asn | Ser | Ala 140 | Leu | Thr | Thr | Ala |
| Ile 145 | Pro | Leu | Phe | Ala | Val 150 | Gln | Asn | Tyr | Gln | Val 155 | Pro | Leu | Leu | Ser | Val 160 |
| Tyr | Val | Gln | Ala | Ala 165 | Asn | Leu | His | Leu | Ser 170 | Val | Leu | Arg | Asp | Val 175 | Ser |
| Val | Phe | Gly | Gln 180 | Arg | Trp | Gly | Phe | Asp 185 | Ala | Ala | Thr | Ile | Asn 190 | Ser | Arg |
| Tyr | Asn | Asp 195 | Leu | Thr | Arg | Leu | Ile 200 | Gly | Asn | Tyr | Thr | Asp 205 | Tyr | Ala | Val |
| Arg | Trp 210 | Tyr | Asn | Thr | Gly | Leu 215 | Glu | Arg | Val | Trp | Gly 220 | Pro | Asp | Ser | Arg |
| Asp 225 | Trp | Val | Arg | Tyr | Asn 230 | Gln | Phe | Arg | Arg | Glu 235 | Leu | Thr | Leu | Thr | Val 240 |
| Leu | Asp | Ile | Val | Ala 245 | Leu | Phe | Pro | Asn | Tyr 250 | Asp | Ser | Arg | Arg | Tyr 255 | Pro |
| Ile | Arg | Thr | Val 260 | Ser | Gln | Leu | Thr | Arg 265 | Glu | Ile | Tyr | Thr | Asn 270 | Pro | Val |
| Leu | Glu | Asn 275 | Phe | Asp | Gly | Ser | Phe 280 | Arg | Gly | Ser | Ala | Gln 285 | Gly | Ile | Glu |
| Arg | Ser 290 | Ile | Arg | Ser | Pro | His 295 | Leu | Met | Asp | Ile | Leu 300 | Asn | Ser | Ile | Thr |
| Ile 305 | Tyr | Thr | Asp | Ala | His 310 | Arg | Gly | Tyr | Tyr | Tyr 315 | Trp | Ser | Gly | His | Gln 320 |
| Ile | Met | Ala | Ser | Pro 325 | Val | Gly | Phe | Ser | Gly 330 | Pro | Glu | Phe | Thr | Phe 335 | Pro |
| Leu | Tyr | Gly | Thr 340 | Met | Gly | Asn | Ala | Ala 345 | Pro | Gln | Gln | Arg | Ile 350 | Val | Ala |
| Gln | Leu | Gly 355 | Gln | Gly | Val | Tyr | Arg 360 | Thr | Leu | Ser | Ser | Thr 365 | Leu | Tyr | Arg |
| Arg | Pro 370 | Phe | Asn | Ile | Gly | Ile 375 | Asn | Asn | Gln | Gln | Leu 380 | Ser | Val | Leu | Asp |
| Gly 385 | Thr | Glu | Phe | Ala | Tyr 390 | Gly | Thr | Ser | Ser | Asn 395 | Leu | Pro | Ser | Ala | Val 400 |
| Tyr | Arg | Lys | Ser | Gly 405 | Thr | Val | Asp | Ser | Leu 410 | Asp | Glu | Ile | Pro | Pro 415 | Gln |
| Asn | Asn | Asn | Val 420 | Pro | Pro | Arg | Gln | Gly 425 | Phe | Ser | His | Arg | Leu 430 | Ser | His |
| Val | Ser | Met 435 | Phe | Arg | Ser | Gly | Phe 440 | Ser | Asn | Ser | Ser | Val 445 | Ser | Ile | Ile |

| | | | | | | | | | | | | | | |
|---|---|---|---|---|---|---|---|---|---|---|---|---|---|---|
| Arg | Ala | Pro | Met | Phe | Ser | Trp | Ile | His | Arg | Ser | Ala | Glu | Phe | Asn | Asn |
| | 450 | | | | 455 | | | | | 460 | | | | |
| Ile | Ile | Pro | Ser | Ser | Gln | Ile | Thr | Gln | Ile | Pro | Leu | Thr | Lys | Ser | Thr |
| 465 | | | | | 470 | | | | | 475 | | | | | 480 |
| Asn | Leu | Gly | Ser | Gly | Thr | Ser | Val | Val | Lys | Gly | Pro | Gly | Phe | Thr | Gly |
| | | | | 485 | | | | | 490 | | | | | 495 | |
| Gly | Asp | Ile | Leu | Arg | Arg | Thr | Ser | Pro | Gly | Gln | Ile | Ser | Thr | Leu | Arg |
| | | | 500 | | | | | 505 | | | | | 510 | | |
| Val | Asn | Ile | Thr | Ala | Pro | Leu | Ser | Gln | Arg | Tyr | Arg | Val | Arg | Ile | Arg |
| | | 515 | | | | | 520 | | | | | 525 | | | |
| Tyr | Ala | Ser | Thr | Thr | Asn | Leu | Gln | Phe | His | Thr | Ser | Ile | Asp | Gly | Arg |
| | 530 | | | | | 535 | | | | | 540 | | | | |
| Pro | Ile | Asn | Gln | Gly | Asn | Phe | Ser | Ala | Thr | Met | Ser | Ser | Gly | Ser | Asn |
| 545 | | | | | 550 | | | | | 555 | | | | | 560 |
| Leu | Gln | Ser | Gly | Ser | Phe | Arg | Thr | Val | Gly | Phe | Thr | Thr | Pro | Phe | Asn |
| | | | | 565 | | | | | 570 | | | | | 575 | |
| Phe | Ser | Asn | Gly | Ser | Ser | Val | Phe | Thr | Leu | Ser | Ala | His | Val | Phe | Asn |
| | | | 580 | | | | | 585 | | | | | 590 | | |
| Ser | Gly | Asn | Glu | Val | Tyr | Ile | Asp | Arg | Ile | Glu | Phe | Val | Pro | Ala | Glu |
| | | 595 | | | | | 600 | | | | | 605 | | | |
| Val | Thr | Phe | Glu | Ala | Glu | Tyr | Asp | Leu | Glu | Arg | Ala | Gln | Lys | Ala | Val |
| | 610 | | | | | 615 | | | | | 620 | | | | |
| Asn | Glu | Leu | Phe | Thr | Ser | Ser | Asn | Gln | Ile | Gly | Leu | Lys | Thr | Asp | Val |
| 625 | | | | | 630 | | | | | 635 | | | | | 640 |
| Thr | Asp | Tyr | His | Ile | Asp | Arg | Val | Ser | Asn | Leu | Val | Glu | Cys | Leu | Ser |
| | | | 645 | | | | | 650 | | | | | 655 | | |
| Asp | Glu | Phe | Cys | Leu | Asp | Glu | Lys | Lys | Glu | Leu | Ser | Glu | Lys | Val | Lys |
| | | | 660 | | | | | 665 | | | | | 670 | | |
| His | Ala | Lys | Arg | Leu | Ser | Asp | Glu | Arg | Asn | Leu | Leu | Gln | Asp | Pro | Asn |
| | | 675 | | | | | 680 | | | | | 685 | | | |
| Phe | Arg | Gly | Ile | Asn | Arg | Gln | Leu | Asp | Arg | Gly | Trp | Arg | Gly | Ser | Thr |
| | 690 | | | | | 695 | | | | | 700 | | | | |
| Asp | Ile | Thr | Ile | Gln | Gly | Gly | Asp | Asp | Val | Phe | Lys | Glu | Asn | Tyr | Val |
| 705 | | | | | 710 | | | | | 715 | | | | | 720 |
| Thr | Leu | Leu | Gly | Thr | Phe | Asp | Glu | Cys | Tyr | Pro | Thr | Tyr | Leu | Tyr | Gln |
| | | | | 725 | | | | | 730 | | | | | 735 | |
| Lys | Ile | Asp | Glu | Ser | Lys | Leu | Lys | Ala | Tyr | Thr | Arg | Tyr | Gln | Leu | Arg |
| | | | 740 | | | | | 745 | | | | | 750 | | |
| Gly | Tyr | Ile | Glu | Asp | Ser | Gln | Asp | Leu | Glu | Ile | Tyr | Leu | Ile | Arg | Tyr |
| | | 755 | | | | | 760 | | | | | 765 | | | |
| Asn | Ala | Lys | His | Glu | Thr | Val | Asn | Val | Pro | Gly | Thr | Gly | Ser | Leu | Trp |
| | 770 | | | | | 775 | | | | | 780 | | | | |
| Pro | Leu | Ser | Ala | Pro | Ser | Pro | Ile | Gly | Lys | Cys | Ala | His | His | Ser | His |
| 785 | | | | | 790 | | | | | 795 | | | | | 800 |
| His | Phe | Ser | Leu | Asp | Ile | Asp | Val | Gly | Cys | Thr | Asp | Leu | Asn | Glu | Asp |
| | | | | 805 | | | | | 810 | | | | | 815 | |
| Leu | Gly | Val | Trp | Val | Ile | Phe | Lys | Ile | Lys | Thr | Gln | Asp | Gly | His | Ala |
| | | | 820 | | | | | 825 | | | | | 830 | | |
| Arg | Leu | Gly | Asn | Leu | Glu | Phe | Leu | Glu | Lys | Pro | Leu | Val | Gly | Glu |
| | | 835 | | | | | 840 | | | | | 845 | | | |
| Ala | Leu | Ala | Arg | Val | Lys | Arg | Ala | Glu | Lys | Lys | Trp | Arg | Asp | Lys | Arg |
| | 850 | | | | | 855 | | | | | 860 | | | | |
| Glu | Lys | Leu | Glu | Trp | Glu | Thr | Asn | Ile | Val | Tyr | Lys | Glu | Ala | Lys | Glu |

| | 865 | | | | | 870 | | | | | 875 | | | | | 880 | |
|---|---|---|---|---|---|---|---|---|---|---|---|---|---|---|---|---|---|
| Ser | Val | Asp | Ala | Leu | Phe | Val | Asn | Ser | Gln | Tyr | Asp | Arg | Leu | Gln | Ala |
| | | | | 885 | | | | | 890 | | | | | 895 | |
| Asp | Thr | Asn | Ile | Ala | Met | Ile | His | Ala | Ala | Asp | Lys | Arg | Val | His | Ser |
| | | | 900 | | | | | 905 | | | | | 910 | | |
| Ile | Arg | Glu | Ala | Tyr | Leu | Pro | Glu | Leu | Ser | Val | Ile | Pro | Gly | Val | Asn |
| | | 915 | | | | | 920 | | | | | 925 | | | |
| Ala | Ala | Ile | Phe | Glu | Glu | Leu | Glu | Gly | Arg | Ile | Phe | Thr | Ala | Phe | Ser |
| | 930 | | | | | 935 | | | | | 940 | | | | |
| Leu | Tyr | Asp | Ala | Arg | Asn | Val | Ile | Lys | Asn | Gly | Asp | Phe | Asn | Asn | Gly |
| 945 | | | | | 950 | | | | | 955 | | | | | 960 |
| Leu | Ser | Cys | Trp | Asn | Val | Lys | Gly | His | Val | Asp | Val | Glu | Glu | Gln | Asn |
| | | | | 965 | | | | | 970 | | | | | 975 | |
| Asn | His | Arg | Ser | Val | Leu | Val | Val | Pro | Glu | Trp | Glu | Ala | Glu | Val | Ser |
| | | | 980 | | | | | 985 | | | | | 990 | | |
| Gln | Glu | Val | Arg | Val | Cys | Pro | Gly | Arg | Gly | Tyr | Ile | Leu | Arg | Val | Thr |
| | | 995 | | | | | 1000 | | | | | 1005 | | | |
| Ala | Tyr | Lys | Glu | Gly | Tyr | Gly | Glu | Gly | Cys | Val | Thr | Ile | His | Glu | Ile |
| | 1010 | | | | | 1015 | | | | | 1020 | | | | |
| Glu | Asn | Asn | Thr | Asp | Glu | Leu | Lys | Phe | Ser | Asn | Cys | Val | Glu | Glu | Glu |
| 1025 | | | | | 1030 | | | | | 1035 | | | | | 1040 |
| Val | Tyr | Pro | Asn | Asn | Thr | Val | Thr | Cys | Asn | Asp | Tyr | Thr | Ala | Thr | Gln |
| | | | | 1045 | | | | | 1050 | | | | | 1055 | |
| Glu | Glu | Tyr | Glu | Gly | Thr | Tyr | Thr | Ser | Arg | Asn | Arg | Gly | Tyr | Asp | Gly |
| | | | 1060 | | | | | 1065 | | | | | 1070 | | |
| Ala | Tyr | Glu | Ser | Asn | Ser | Ser | Val | Pro | Ala | Asp | Tyr | Ala | Ser | Ala | Tyr |
| | | 1075 | | | | | 1080 | | | | | 1085 | | | |
| Glu | Glu | Lys | Ala | Tyr | Thr | Asp | Gly | Arg | Arg | Asp | Asn | Pro | Cys | Glu | Ser |
| | 1090 | | | | | 1095 | | | | | 1100 | | | | |
| Asn | Arg | Gly | Tyr | Gly | Asp | Tyr | Thr | Pro | Leu | Pro | Ala | Gly | Tyr | Val | Thr |
| 1105 | | | | | 1110 | | | | | 1115 | | | | | 1120 |
| Lys | Glu | Leu | Glu | Tyr | Phe | Pro | Glu | Thr | Asp | Lys | Val | Trp | Ile | Glu | Ile |
| | | | | 1125 | | | | | 1130 | | | | | 1135 | |
| Gly | Glu | Thr | Glu | Gly | Thr | Phe | Ile | Val | Asp | Ser | Val | Glu | Leu | Leu | Leu |
| | | | 1140 | | | | | 1145 | | | | | 1150 | | |
| Met | Glu | Glu |
| | 1155 | |

(2) INFORMATION FOR SEQ ID NO:20:

(i) SEQUENCE CHARACTERISTICS:
        (A) LENGTH: 3450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

| | | | | | |
|---|---|---|---|---|---|
| ATGGATAACA | ATCCGAACAT | CAATGAATGC | ATTCCTTATA | ATTGTTTAAG | TAACCCTGAA | 60 |
| GTAGAAGTAT | TAGGTGGAGA | AAGAATAGAA | ACTGGTTACA | CCCCAATCGA | TATTTCCTTG | 120 |
| TCGCTAACGC | AATTTCTTTT | GAGTGAATTT | GTTCCCGGTG | CTGGATTTGT | GTTAGGACTA | 180 |
| GTTGATATAA | TATGGGGAAT | TTTTGGTCCC | TCTCAATGGG | ACGCATTTCT | TGTACAAATT | 240 |
| GAACAGTTAA | TTAACCAAAG | AATAGAAGAA | TTCGCTAGGA | ACCAAGCCAT | TTCTAGATTA | 300 |
| GAAGGACTAA | GCAATCTTTA | TCAAATTTAC | GCAGAATCTT | TTAGAGAGTG | GGAAGCGGAT | 360 |

| | | | | | | |
|---|---|---|---|---|---|---|
| CTTAATAATG | CACAATTAAG | GGAAGATGTG | CGTATTCGAT | TTGCTAATAC | AGACGACGCT | 420 |
| TTAATAACAG | CAATAAATAA | TTTTACACTT | ACAAGTTTTG | AAATCCCTCT | TTTATCGGTC | 480 |
| TATGTTCAAG | CGGCGAATTT | ACATTTATCA | CTATTAAGAG | ACGCTGTATC | GTTTGGGCAG | 540 |
| GGTTGGGGAC | TGGATATAGC | TACTGTTAAT | AATCATTATA | ATAGATTAAT | AAATCTTATT | 600 |
| CATAGATATA | CGAAACATTG | TTTGGACACA | TACAATCAAG | GATTAGAAAA | CTTAAGAGGT | 660 |
| ACTAATACTC | GACAATGGGC | AAGATTCAAT | CAGTTTAGGA | GAGATTTAAC | ACTTACTGTA | 720 |
| TTAGATATCG | TTGCTCTTTT | TCCGAACTAC | GATGTTAGAA | CATATCCAAT | TCAAACGTCA | 780 |
| TCCCAATTAA | CAAGGGAAAT | TTATACAAGT | TCAGTAATTG | AGGATTCTCC | AGTTTCTGCT | 840 |
| AATATACCTA | ATGGTTTTAA | TAGGGCGGAA | TTTGGAGTTA | GACCGCCCCA | TCTTATGGAC | 900 |
| TTTATGAATT | CTTTGTTTGT | AACTGCAGAG | ACTGTTAGAA | GTCAAACTGT | GTGGGGAGGA | 960 |
| CACTTAGTTA | GTTCACGAAA | TACGGCTGGT | AACCGTATAA | ATTTCCCTAG | TTACGGGTC | 1020 |
| TTCAATCCTG | GTGGCGCCAT | TTGGATTGCA | GATGAGGATC | CACGTCCTTT | TTATCGGACA | 1080 |
| TTATCAGATC | CTGTTTTTGT | CCGAGGAGGA | TTTGGGAATC | CTCATTATGT | ACTGGGGCTT | 1140 |
| AGGGGAGTAG | CATTTCAACA | AACTGGTACG | AACCACACCC | GAACATTTAG | AAATAGTGGG | 1200 |
| ACCATAGATT | CTCTAGATGA | AATCCCACCT | CAGGATAATA | GTGGGGCACC | TTGGAATGAT | 1260 |
| TATAGTCATG | TATTAAATCA | TGTTACATTT | GTACGATGGC | CAGGTGAGAT | TCAGGAAGT | 1320 |
| GATTCATGGA | GAGCTCCAAT | GTTTCTTGG | ACGCACCGTA | GTGCAACCCC | TACAAATACA | 1380 |
| ATTGATCCGG | AGAGGATTAC | TCAAATACCA | TTGGTAAAAG | CACATACACT | TCAGTCAGGT | 1440 |
| ACTACTGTTG | TAAGAGGGCC | CGGGTTTACG | GGAGGAGATA | TTCTTCGACG | AACAAGTGGA | 1500 |
| GGACCATTTG | CTTATACTAT | TGTTAATATA | AATGGGCAAT | TACCCCAAAG | GTATCGTGCA | 1560 |
| AGAATACGCT | ATGCCTCTAC | TACAAATCTA | AGAATTTACG | TAACGGTTGC | AGGTGAACGG | 1620 |
| ATTTTTGCTG | GTCAATTTAA | CAAAACAATG | GATACCGGTG | ACCCATTAAC | ATTCCAATCT | 1680 |
| TTTAGTTACG | CAACTATTAA | TACAGCTTTT | ACATTCCCAA | TGAGCCAGAG | TAGTTTCACA | 1740 |
| GTAGGTGCTG | ATACTTTTAG | TTCAGGGAAT | GAAGTTTATA | TAGACAGATT | TGAATTGATT | 1800 |
| CCAGTTACTG | CAACATTTGA | AGCAGAATAT | GATTTAGAAA | GAGCACAAAA | GGCGGTGAAT | 1860 |
| GCGCTGTTTA | CTTCTATAAA | CCAAATAGGG | ATAAAAACAG | ATGTGACGGA | TTATCATATC | 1920 |
| GATCGAGTAT | CCAATTTAGT | TGAGTGTTTA | TCTGATGAAT | TTTGTCTGGA | TGAAAAAAAA | 1980 |
| GAATTGTCCG | AGAAAGTCAA | ACATGCGAAG | CGACTTAGTG | ATGAGCGGAA | TTTACTTCAA | 2040 |
| GATCCAAACT | TTAGAGGGAT | CAATAGACAA | CTAGACCGTG | GCTGGAGAGG | AAGTACGGAT | 2100 |
| ATTACCATCC | AAGGAGGCGA | TGACGTATTC | AAAGAGAATT | ACGTTACGCT | ATTGGGTACC | 2160 |
| TTTGATGAGT | GCTATCCAAC | GTATTTATAT | CAAAAAATAG | ATGAGTCGAA | ATTAAAAGCC | 2220 |
| TATACCCGTT | ACCAATTAAG | AGGGTATATC | GAAGATAGTC | AAGACTTAGA | AATCTATTTA | 2280 |
| ATTCGCTACA | ATGCCAAACA | CGAAACAGTA | AATGTGCCAG | GTACGGGTTC | CTTATGGCCG | 2340 |
| CTTTCAGCCC | CAAGTCCAAT | CGGAAAATGT | GCCCATCATT | CCCATCATTT | CTCCTTGGAC | 2400 |
| ATTGATGTTG | GATGTACAGA | CTTAAATGAG | GACTTAGGTG | TATGGGTGAT | ATTCAAGATT | 2460 |
| AAGACGCAAG | ATGGCCATGC | AAGACTAGGA | AATCTAGAAT | TTCTCGAAGA | GAAACCATTA | 2520 |
| GTAGGAGAAG | CACTAGCTCG | TGTGAAAAGA | GCGGAGAAAA | AATGGAGAGA | CAAACGTGAA | 2580 |
| AAATTGGAAT | GGGAAACAAA | TATTGTTTAT | AAAGAGGCAA | AAGAATCTGT | AGATGCTTTA | 2640 |
| TTTGTAAACT | CTCAATATGA | TAGATTACAA | GCGGATACCA | ACATCGCGAT | GATTCATGCG | 2700 |
| GCAGATAAAC | GCGTTCATAG | CATTCGAGAA | GCTTATCTGC | CTGAGCTGTC | TGTGATTCCG | 2760 |

```
GGTGTCAATG CGGCTATTTT TGAAGAATTA GAAGGGCGTA TTTTCACTGC ATTCTCCCTA    2820
TATGATGCGA GAAATGTCAT TAAAAATGGT GATTTTAATA ATGGCTTATC CTGCTGGAAC    2880
GTGAAAGGGC ATGTAGATGT AGAAGAACAA AACAACCACC GTTCGGTCCT TGTTGTTCCG    2940
GAATGGGAAG CAGAAGTGTC ACAAGAAGTT CGTGTCTGTC CGGGTCGTGG CTATATCCTT    3000
CGTGTCACAG CGTACAAGGA GGGATATGGA GAAGGTTGCG TAACCATTCA TGAGATCGAG    3060
AACAATACAG ACGAACTGAA GTTTAGCAAC TGTGTAGAAG AGGAAGTATA TCCAAACAAC    3120
ACGGTAACGT GTAATGATTA TACTGCGACT CAAGAAGAAT ATGAGGGTAC GTACACTTCT    3180
CGTAATCGAG GATATGACGG AGCCTATGAA AGCAATTCTT CTGTACCAGC TGATTATGCA    3240
TCAGCCTATG AAGAAAAAGC ATATACAGAT GGACGAAGAG ACAATCCTTG TGAATCTAAC    3300
AGAGGATATG GGGATTACAC ACCACTACCA GCTGGCTATG TGACAAAAGA ATTAGAGTAC    3360
TTCCCAGAAA CCGATAAGGT ATGGATTGAG ATCGGAGAAA CGGAAGGAAC ATTCATCGTG    3420
GACAGCGTGG AATTACTTCT TATGGAGGAA                                       3450
```

(2) INFORMATION FOR SEQ ID NO:21:

(i) SEQUENCE CHARACTERISTICS:
    (A) LENGTH: 1150 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:21:

```
Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
                100                 105                 110

Ser Phe Arg Glu Trp Glu Ala Asp Leu Asn Asn Ala Gln Leu Arg Glu
        115                 120                 125

Asp Val Arg Ile Arg Phe Ala Asn Thr Asp Asp Ala Leu Ile Thr Ala
    130                 135                 140

Ile Asn Asn Phe Thr Leu Thr Ser Phe Glu Ile Pro Leu Leu Ser Val
145                 150                 155                 160

Tyr Val Gln Ala Ala Asn Leu His Leu Ser Leu Leu Arg Asp Ala Val
                165                 170                 175

Ser Phe Gly Gln Gly Trp Gly Leu Asp Ile Ala Thr Val Asn Asn His
        180                 185                 190

Tyr Asn Arg Leu Ile Asn Leu Ile His Arg Tyr Thr Lys His Cys Leu
    195                 200                 205

Asp Thr Tyr Asn Gln Gly Leu Glu Asn Leu Arg Gly Thr Asn Thr Arg
210                 215                 220
```

```
Gln  Trp  Ala  Arg  Phe  Asn  Gln  Phe  Arg  Arg  Asp  Leu  Thr  Leu  Thr  Val
225            230                      235                      240

Leu  Asp  Ile  Val  Ala  Leu  Phe  Pro  Asn  Tyr  Asp  Val  Arg  Thr  Tyr  Pro
               245                      250                      255

Ile  Gln  Thr  Ser  Ser  Gln  Leu  Thr  Arg  Glu  Ile  Tyr  Thr  Ser  Ser  Val
                    260                      265                      270

Ile  Glu  Asp  Ser  Pro  Val  Ser  Ala  Asn  Ile  Pro  Asn  Gly  Phe  Asn  Arg
          275                      280                      285

Ala  Glu  Phe  Gly  Val  Arg  Pro  Pro  His  Leu  Met  Asp  Phe  Met  Asn  Ser
     290                      295                      300

Leu  Phe  Val  Thr  Ala  Glu  Thr  Val  Arg  Ser  Gln  Thr  Val  Trp  Gly  Gly
305                 310                      315                      320

His  Leu  Val  Ser  Ser  Arg  Asn  Thr  Ala  Gly  Asn  Arg  Ile  Asn  Phe  Pro
                    325                      330                      335

Ser  Tyr  Gly  Val  Phe  Asn  Pro  Gly  Gly  Ala  Ile  Trp  Ile  Ala  Asp  Glu
               340                      345                      350

Asp  Pro  Arg  Pro  Phe  Tyr  Arg  Thr  Leu  Ser  Asp  Pro  Val  Phe  Val  Arg
          355                      360                      365

Gly  Gly  Phe  Gly  Asn  Pro  His  Tyr  Val  Leu  Gly  Leu  Arg  Gly  Val  Ala
          370                      375                      380

Phe  Gln  Gln  Thr  Gly  Thr  Asn  His  Thr  Arg  Thr  Phe  Arg  Asn  Ser  Gly
385                      390                      395                      400

Thr  Ile  Asp  Ser  Leu  Asp  Glu  Ile  Pro  Pro  Gln  Asp  Asn  Ser  Gly  Ala
                    405                      410                      415

Pro  Trp  Asn  Asp  Tyr  Ser  His  Val  Leu  Asn  His  Val  Thr  Phe  Val  Arg
               420                      425                      430

Trp  Pro  Gly  Glu  Ile  Ser  Gly  Ser  Asp  Ser  Trp  Arg  Ala  Pro  Met  Phe
          435                      440                      445

Ser  Trp  Thr  His  Arg  Ser  Ala  Thr  Pro  Thr  Asn  Thr  Ile  Asp  Pro  Glu
     450                      455                      460

Arg  Ile  Thr  Gln  Ile  Pro  Leu  Val  Lys  Ala  His  Thr  Leu  Gln  Ser  Gly
465                      470                      475                      480

Thr  Thr  Val  Val  Arg  Gly  Pro  Gly  Phe  Thr  Gly  Gly  Asp  Ile  Leu  Arg
                    485                      490                      495

Arg  Thr  Ser  Gly  Gly  Pro  Phe  Ala  Tyr  Thr  Ile  Val  Asn  Ile  Asn  Gly
               500                      505                      510

Gln  Leu  Pro  Gln  Arg  Tyr  Arg  Ala  Arg  Ile  Arg  Tyr  Ala  Ser  Thr  Thr
          515                      520                      525

Asn  Leu  Arg  Ile  Tyr  Val  Thr  Val  Ala  Gly  Glu  Arg  Ile  Phe  Ala  Gly
     530                      535                      540

Gln  Phe  Asn  Lys  Thr  Met  Asp  Thr  Gly  Asp  Pro  Leu  Thr  Phe  Gln  Ser
545                      550                      555                      560

Phe  Ser  Tyr  Ala  Thr  Ile  Asn  Thr  Ala  Phe  Thr  Phe  Pro  Met  Ser  Gln
                    565                      570                      575

Ser  Ser  Phe  Thr  Val  Gly  Ala  Asp  Thr  Phe  Ser  Ser  Gly  Asn  Glu  Val
               580                      585                      590

Tyr  Ile  Asp  Arg  Phe  Glu  Leu  Ile  Pro  Val  Thr  Ala  Thr  Phe  Glu  Ala
          595                      600                      605

Glu  Tyr  Asp  Leu  Glu  Arg  Ala  Gln  Lys  Ala  Val  Asn  Ala  Leu  Phe  Thr
     610                      615                      620

Ser  Ile  Asn  Gln  Ile  Gly  Ile  Lys  Thr  Asp  Val  Thr  Asp  Tyr  His  Ile
625                      630                      635                      640

Asp  Arg  Val  Ser  Asn  Leu  Val  Glu  Cys  Leu  Ser  Asp  Glu  Phe  Cys  Leu
                    645                      650                      655
```

```
Asp  Glu  Lys  Lys  Glu  Leu  Ser  Glu  Lys  Val  Lys  His  Ala  Lys  Arg  Leu
               660                 665                 670

Ser  Asp  Glu  Arg  Asn  Leu  Leu  Gln  Asp  Pro  Asn  Phe  Arg  Gly  Ile  Asn
          675                      680                 685

Arg  Gln  Leu  Asp  Arg  Gly  Trp  Arg  Gly  Ser  Thr  Asp  Ile  Thr  Ile  Gln
     690                 695                      700

Gly  Gly  Asp  Asp  Val  Phe  Lys  Glu  Asn  Tyr  Val  Thr  Leu  Leu  Gly  Thr
705                      710                 715                           720

Phe  Asp  Glu  Cys  Tyr  Pro  Thr  Tyr  Leu  Tyr  Gln  Lys  Ile  Asp  Glu  Ser
                    725                 730                      735

Lys  Leu  Lys  Ala  Tyr  Thr  Arg  Tyr  Gln  Leu  Arg  Gly  Tyr  Ile  Glu  Asp
               740                      745                      750

Ser  Gln  Asp  Leu  Glu  Ile  Tyr  Leu  Ile  Arg  Tyr  Asn  Ala  Lys  His  Glu
          755                      760                      765

Thr  Val  Asn  Val  Pro  Gly  Thr  Gly  Ser  Leu  Trp  Pro  Leu  Ser  Ala  Pro
770                           775                 780

Ser  Pro  Ile  Gly  Lys  Cys  Ala  His  Ser  His  His  Phe  Ser  Leu  Asp
785                      790                 795                      800

Ile  Asp  Val  Gly  Cys  Thr  Asp  Leu  Asn  Asp  Leu  Gly  Val  Trp  Val
                    805                 810                      815

Ile  Phe  Lys  Ile  Lys  Thr  Gln  Asp  Gly  His  Ala  Arg  Leu  Gly  Asn  Leu
               820                 825                      830

Glu  Phe  Leu  Glu  Glu  Lys  Pro  Leu  Val  Gly  Glu  Ala  Leu  Ala  Arg  Val
          835                      840                 845

Lys  Arg  Ala  Glu  Lys  Lys  Trp  Arg  Asp  Lys  Arg  Glu  Lys  Leu  Glu  Trp
850                           855                 860

Glu  Thr  Asn  Ile  Val  Tyr  Lys  Glu  Ala  Lys  Glu  Ser  Val  Asp  Ala  Leu
865                      870                 875                           880

Phe  Val  Asn  Ser  Gln  Tyr  Asp  Arg  Leu  Gln  Ala  Asp  Thr  Asn  Ile  Ala
                    885                      890                      895

Met  Ile  His  Ala  Ala  Asp  Lys  Arg  Val  His  Ser  Ile  Arg  Glu  Ala  Tyr
                    900                 905                      910

Leu  Pro  Glu  Leu  Ser  Val  Ile  Pro  Gly  Val  Asn  Ala  Ala  Ile  Phe  Glu
          915                      920                 925

Glu  Leu  Glu  Gly  Arg  Ile  Phe  Thr  Ala  Phe  Ser  Leu  Tyr  Asp  Ala  Arg
     930                      935                      940

Asn  Val  Ile  Lys  Asn  Gly  Asp  Phe  Asn  Asn  Gly  Leu  Ser  Cys  Trp  Asn
945                      950                      955                      960

Val  Lys  Gly  His  Val  Asp  Val  Glu  Glu  Gln  Asn  Asn  His  Arg  Ser  Val
               965                      970                      975

Leu  Val  Val  Pro  Glu  Trp  Glu  Ala  Glu  Val  Ser  Gln  Glu  Val  Arg  Val
               980                      985                      990

Cys  Pro  Gly  Arg  Gly  Tyr  Ile  Leu  Arg  Val  Thr  Ala  Tyr  Lys  Glu  Gly
          995                      1000                1005

Tyr  Gly  Glu  Gly  Cys  Val  Thr  Ile  His  Glu  Ile  Glu  Asn  Asn  Thr  Asp
     1010                1015                     1020

Glu  Leu  Lys  Phe  Ser  Asn  Cys  Val  Glu  Glu  Val  Tyr  Pro  Asn  Asn
1025                     1030                     1035                     1040

Thr  Val  Thr  Cys  Asn  Asp  Tyr  Thr  Ala  Thr  Gln  Glu  Glu  Tyr  Glu  Gly
                    1045                     1050                     1055

Thr  Tyr  Thr  Ser  Arg  Asn  Arg  Gly  Tyr  Asp  Gly  Ala  Tyr  Glu  Ser  Asn
                    1060                     1065                     1070

Ser  Ser  Val  Pro  Ala  Asp  Tyr  Ala  Ser  Ala  Tyr  Glu  Glu  Lys  Ala  Tyr
```

|   | 1075 | 1080 | 1085 |
|---|---|---|---|

Thr Asp Gly Arg Arg Asp Asn Pro Cys Glu Ser Asn Arg Gly Tyr Gly
    1090                1095            1100

Asp Tyr Thr Pro Leu Pro Ala Gly Tyr Val Thr Lys Glu Leu Glu Tyr
1105            1110                1115                1120

Phe Pro Glu Thr Asp Lys Val Trp Ile Glu Ile Gly Glu Thr Glu Gly
            1125            1130                    1135

Thr Phe Ile Val Asp Ser Val Glu Leu Leu Leu Met Glu Glu
            1140            1145                1150

( 2 ) INFORMATION FOR SEQ ID NO:22:

( i ) SEQUENCE CHARACTERISTICS:
        ( A ) LENGTH: 3444 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

```
ATGGAGAATA ATATTCAAAA TCAATGCGTA CCTTACAATT GTTTAAATAA TCCTGAAGTA      60
GAAATATTAA ATGAAGAAAG AAGTACTGGC AGATTACCGT TAGATATATC CTTATCGCTT     120
ACACGTTTCC TTTTGAGTGA ATTTGTTCCA GGTGTGGGAG TTGCGTTTGG ATTATTTGAT     180
TTAATATGGG GTTTTATAAC TCCTTCTGAT TGGAGCTTAT TTCTTTTACA GATTGAACAA     240
TTGATTGAGC AAAGAATAGA AACATTGGAA AGGAACCGGG CAATTACTAC ATTACGAGGG     300
TTAGCAGATA GCTATGAAAT TTATATTGAA GCACTAAGAG AGTGGGAAGC AAATCCTAAT     360
AATGCACAAT TAAGGGAAGA TGTGCGTATT CGATTTGCTA ATACAGACGA CGCTTTAATA     420
ACAGCAATAA ATAATTTTAC ACTTACAAGT TTTGAAATCC CTCTTTTATC GGTCTATGTT     480
CAAGCGGCGA ATTTACATTT ATCACTATTA AGAGACGCTG TATCGTTTGG GCAGGGTTGG     540
GGACTGGATA TAGCTACTGT TAATAATCAT TATAATAGAT TAATAAATCT TATTCATAGA     600
TATACGAAAC ATTGTTTGGA CACATACAAT CAAGGATTAG AAAACTTAAG AGGTACTAAT     660
ACTCGACAAT GGGCAAGATT CAATCAGTTT AGGAGAGATT TAACACTTAC TGTATTAGAT     720
ATCGTTGCTC TTTTTCCGAA CTACGATGTT AGAACATATC CAATTCAAAC GTCATCCCAA     780
TTAACAAGGG AAATTTATAC AAGTTCAGTA ATTGAGGATT CTCCAGTTTC TGCTAATATA     840
CCTAATGGTT TTAATAGGGC GGAATTTGGA GTTAGACCGC CCATCTTAT GGACTTTATG     900
AATTCTTTGT TTGTAACTGC AGAGACTGTT AGAAGTCAAA CTGTGTGGGG AGGACACTTA     960
GTTAGTTCAC GAAATACGGC TGGTAACCGT ATAAATTTCC CTAGTTACGG GGTCTTCAAT    1020
CCTGGTGGCG CCATTTGGAT TGCAGATGAG GATCCACGTC CTTTTTATCG GACATTATCA    1080
GATCCTGTTT TTGTCCGAGG AGGATTTGGG AATCCTCATT ATGTACTGGG GCTTAGGGGA    1140
GTAGCATTTC AACAAACTGG TACGAACCAC ACCCGAACAT TTAGAAATAG TGGGACCATA    1200
GATTCTCTAG ATGAAATCCC ACCTCAGGAT AATAGTGGGG CACCTTGGAA TGATTATAGT    1260
CATGTATTAA ATCATGTTAC ATTTGTACGA TGGCCAGGTG AGATTTCAGG AAGTGATTCA    1320
TGGAGAGCTC CAATGTTTTC TTGGACGCAC CGTAGTGCAA CCCCTACAAA TACAATTGAT    1380
CCGGAGAGGA TTACTCAAAT ACCATTGGTA AAAGCACATA CACTTCAGTC AGGTACTACT    1440
GTTGTAAGAG GGCCCGGGTT TACGGGAGGA GATATTCTTC GACGAACAAG TGGAGGACCA    1500
TTTGCTTATA CTATTGTTAA TATAAATGGG CAATTACCCC AAAGGTATCG TGCAAGAATA    1560
CGCTATGCCT CTACTACAAA TCTAAGAATT TACGTAACGG TTGCAGGTGA ACGGATTTTT    1620
```

| | | | | | |
|---|---|---|---|---|---|
| GCTGGTCAAT | TTAACAAAAC | AATGGATACC | GGTGACCCAT | TAACATTCCA | ATCTTTTAGT | 1680
| TACGCAACTA | TTAATACAGC | TTTTACATTC | CCAATGAGCC | AGAGTAGTTT | CACAGTAGGT | 1740
| GCTGATACTT | TTAGTTCAGG | GAATGAAGTT | TATATAGACA | GATTTGAATT | GATTCCAGTT | 1800
| ACTGCAACAT | TTGAAGCAGA | ATATGATTTA | GAAAGAGCAC | AAAAGGCGGT | GAATGCGCTG | 1860
| TTTACTTCTA | TAAACCAAAT | AGGGATAAAA | ACAGATGTGA | CGGATTATCA | TATCGATCGA | 1920
| GTATCCAATT | TAGTTGAGTG | TTTATCTGAT | GAATTTTGTC | TGGATGAAAA | AAAAGAATTG | 1980
| TCCGAGAAAG | TCAAACATGC | GAAGCGACTT | AGTGATGAGC | GGAATTTACT | TCAAGATCCA | 2040
| AACTTTAGAG | GGATCAATAG | ACAACTAGAC | CGTGGCTGGA | GAGGAAGTAC | GGATATTACC | 2100
| ATCCAAGGAG | GCGATGACGT | ATTCAAAGAG | AATTACGTTA | CGCTATTGGG | TACCTTTGAT | 2160
| GAGTGCTATC | CAACGTATTT | ATATCAAAAA | ATAGATGAGT | CGAAATTAAA | AGCCTATACC | 2220
| CGTTACCAAT | TAAGAGGGTA | TATCGAAGAT | AGTCAAGACT | TAGAAATCTA | TTTAATTCGC | 2280
| TACAATGCCA | AACACGAAAC | AGTAAATGTG | CCAGGTACGG | GTTCCTTATG | GCCGCTTTCA | 2340
| GCCCCAAGTC | CAATCGGAAA | ATGTGCCCAT | CATTCCATC | ATTTCTCCTT | GGACATTGAT | 2400
| GTTGGATGTA | CAGACTTAAA | TGAGGACTTA | GGTGTATGGG | TGATATTCAA | GATTAAGACG | 2460
| CAAGATGGCC | ATGCAAGACT | AGGAAATCTA | GAATTTCTCG | AAGAGAAACC | ATTAGTAGGA | 2520
| GAAGCACTAG | CTCGTGTGAA | AAGAGCGGAG | AAAAAATGGA | GAGACAAACG | TGAAAAATTG | 2580
| GAATGGGAAA | CAAATATTGT | TTATAAAGAG | GCAAAAGAAT | CTGTAGATGC | TTTATTTGTA | 2640
| AACTCTCAAT | ATGATAGATT | ACAAGCGGAT | ACCAACATCG | CGATGATTCA | TGCGGCAGAT | 2700
| AAACGCGTTC | ATAGCATTCG | AGAAGCTTAT | CTGCCTGAGC | TGTCTGTGAT | TCCGGGTGTC | 2760
| AATGCGGCTA | TTTTTGAAGA | ATTAGAAGGG | CGTATTTTCA | CTGCATTCTC | CCTATATGAT | 2820
| GCGAGAAATG | TCATTAAAAA | TGGTGATTTT | AATAATGGCT | TATCCTGCTG | GAACGTGAAA | 2880
| GGGCATGTAG | ATGTAGAAGA | ACAAAACAAC | CACCGTTCGG | TCCTTGTTGT | TCCGGAATGG | 2940
| GAAGCAGAAG | TGTCACAAGA | AGTTCGTGTC | TGTCCGGGTC | GTGGCTATAT | CCTTCGTGTC | 3000
| ACAGCGTACA | AGGAGGGATA | TGGAGAAGGT | TGCGTAACCA | TTCATGAGAT | CGAGAACAAT | 3060
| ACAGACGAAC | TGAAGTTTAG | CAACTGTGTA | GAAGAGGAAG | TATATCCAAA | CAACACGGTA | 3120
| ACGTGTAATG | ATTATACTGC | GACTCAAGAA | GAATATGAGG | GTACGTACAC | TTCTCGTAAT | 3180
| CGAGGATATG | ACGGAGCCTA | TGAAAGCAAT | TCTTCTGTAC | CAGCTGATTA | TGCATCAGCC | 3240
| TATGAAGAAA | AAGCATATAC | AGATGGACGA | AGAGACAATC | CTTGTGAATC | TAACAGAGGA | 3300
| TATGGGGATT | ACACACCACT | ACCAGCTGGC | TATGTGACAA | AAGAATTAGA | GTACTTCCCA | 3360
| GAAACCGATA | AGGTATGGAT | TGAGATCGGA | GAAACGGAAG | GAACATTCAT | CGTGGACAGC | 3420
| GTGGAATTAC | TTCTTATGGA | GGAA | | | | 3444

(2) INFORMATION FOR SEQ ID NO:23:

(i) SEQUENCE CHARACTERISTICS:
  (A) LENGTH: 1148 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:23:

```
Met Glu Asn Asn Ile Gln Asn Gln Cys Val Pro Tyr Asn Cys Leu Asn
 1               5                  10                  15

Asn Pro Glu Val Glu Ile Leu Asn Glu Glu Arg Ser Thr Gly Arg Leu
```

|    |    |    |    |    |    |    | 20 |    |    |    |    |    | 25 |    |    |    |    |    | 30 |    |    |
|----|----|----|----|----|----|----|----|----|----|----|----|----|----|----|----|----|----|----|----|----|----|

Pro Leu Asp Ile Ser Leu Ser Leu Thr Arg Phe Leu Leu Ser Glu Phe
    35                      40                  45

Val Pro Gly Val Gly Val Ala Phe Gly Leu Phe Asp Leu Ile Trp Gly
    50                      55                  60

Phe Ile Thr Pro Ser Asp Trp Ser Leu Phe Leu Leu Gln Ile Glu Gln
65                      70                  75                      80

Leu Ile Glu Gln Arg Ile Glu Thr Leu Glu Arg Asn Arg Ala Ile Thr
                85                      90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
            115                 120                 125

Arg Ile Arg Phe Ala Asn Thr Asp Asp Ala Leu Ile Thr Ala Ile Asn
    130                     135                 140

Asn Phe Thr Leu Thr Ser Phe Glu Ile Pro Leu Leu Ser Val Tyr Val
145                     150                 155                     160

Gln Ala Ala Asn Leu His Leu Ser Leu Leu Arg Asp Ala Val Ser Phe
                165                 170                 175

Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
    195                     200                 205

Tyr Asn Gln Gly Leu Glu Asn Leu Arg Gly Thr Asn Thr Arg Gln Trp
    210                     215                 220

Ala Arg Phe Asn Gln Phe Arg Arg Asp Leu Thr Leu Thr Val Leu Asp
225                     230                 235                     240

Ile Val Ala Leu Phe Pro Asn Tyr Asp Val Arg Thr Tyr Pro Ile Gln
                245                 250                 255

Thr Ser Ser Gln Leu Thr Arg Glu Ile Tyr Thr Ser Ser Val Ile Glu
            260                 265                 270

Asp Ser Pro Val Ser Ala Asn Ile Pro Asn Gly Phe Asn Arg Ala Glu
    275                     280                 285

Phe Gly Val Arg Pro Pro His Leu Met Asp Phe Met Asn Ser Leu Phe
    290                     295                 300

Val Thr Ala Glu Thr Val Arg Ser Gln Thr Val Trp Gly Gly His Leu
305                     310                 315                     320

Val Ser Ser Arg Asn Thr Ala Gly Asn Arg Ile Asn Phe Pro Ser Tyr
                325                 330                 335

Gly Val Phe Asn Pro Gly Gly Ala Ile Trp Ile Ala Asp Glu Asp Pro
            340                 345                 350

Arg Pro Phe Tyr Arg Thr Leu Ser Asp Pro Val Phe Val Arg Gly Gly
    355                     360                 365

Phe Gly Asn Pro His Tyr Val Leu Gly Leu Arg Gly Val Ala Phe Gln
    370                     375                 380

Gln Thr Gly Thr Asn His Thr Arg Thr Phe Arg Asn Ser Gly Thr Ile
385                     390                 395                     400

Asp Ser Leu Asp Glu Ile Pro Pro Gln Asp Asn Ser Gly Ala Pro Trp
                405                 410                 415

Asn Asp Tyr Ser His Val Leu Asn His Val Thr Phe Val Arg Trp Pro
            420                 425                 430

Gly Glu Ile Ser Gly Ser Asp Ser Trp Arg Ala Pro Met Phe Ser Trp
    435                     440                 445

```
Thr  His  Arg  Ser  Ala  Thr  Pro  Thr  Asn  Thr  Ile  Asp  Pro  Glu  Arg  Ile
     450                 455                      460

Thr  Gln  Ile  Pro  Leu  Val  Lys  Ala  His  Thr  Leu  Gln  Ser  Gly  Thr  Thr
465                      470                 475                           480

Val  Val  Arg  Gly  Pro  Gly  Phe  Thr  Gly  Gly  Asp  Ile  Leu  Arg  Arg  Thr
                    485                 490                           495

Ser  Gly  Gly  Pro  Phe  Ala  Tyr  Thr  Ile  Val  Asn  Ile  Asn  Gly  Gln  Leu
               500                 505                           510

Pro  Gln  Arg  Tyr  Arg  Ala  Arg  Ile  Arg  Tyr  Ala  Ser  Thr  Thr  Asn  Leu
          515                      520                 525

Arg  Ile  Tyr  Val  Thr  Val  Ala  Gly  Glu  Arg  Ile  Phe  Ala  Gly  Gln  Phe
     530                 535                      540

Asn  Lys  Thr  Met  Asp  Thr  Gly  Asp  Pro  Leu  Thr  Phe  Gln  Ser  Phe  Ser
545                      550                 555                           560

Tyr  Ala  Thr  Ile  Asn  Thr  Ala  Phe  Thr  Phe  Pro  Met  Ser  Gln  Ser  Ser
                    565                 570                           575

Phe  Thr  Val  Gly  Ala  Asp  Thr  Phe  Ser  Ser  Gly  Asn  Glu  Val  Tyr  Ile
               580                 585                           590

Asp  Arg  Phe  Glu  Leu  Ile  Pro  Val  Thr  Ala  Thr  Phe  Glu  Ala  Glu  Tyr
          595                      600                 605

Asp  Leu  Glu  Arg  Ala  Gln  Lys  Ala  Val  Asn  Ala  Leu  Phe  Thr  Ser  Ile
     610                 615                      620

Asn  Gln  Ile  Gly  Ile  Lys  Thr  Asp  Val  Thr  Asp  Tyr  His  Ile  Asp  Arg
625                      630                 635                           640

Val  Ser  Asn  Leu  Val  Glu  Cys  Leu  Ser  Asp  Glu  Phe  Cys  Leu  Asp  Glu
               645                 650                           655

Lys  Lys  Glu  Leu  Ser  Glu  Lys  Val  Lys  His  Ala  Lys  Arg  Leu  Ser  Asp
          660                      665                 670

Glu  Arg  Asn  Leu  Leu  Gln  Asp  Pro  Asn  Phe  Arg  Gly  Ile  Asn  Arg  Gln
          675                      680                 685

Leu  Asp  Arg  Gly  Trp  Arg  Gly  Ser  Thr  Asp  Ile  Thr  Ile  Gln  Gly  Gly
     690                 695                      700

Asp  Asp  Val  Phe  Lys  Glu  Asn  Tyr  Val  Thr  Leu  Leu  Gly  Thr  Phe  Asp
705                      710                 715                           720

Glu  Cys  Tyr  Pro  Thr  Tyr  Leu  Tyr  Gln  Lys  Ile  Asp  Glu  Ser  Lys  Leu
                    725                 730                           735

Lys  Ala  Tyr  Thr  Arg  Tyr  Gln  Leu  Arg  Gly  Tyr  Ile  Glu  Asp  Ser  Gln
               740                 745                           750

Asp  Leu  Glu  Ile  Tyr  Leu  Ile  Arg  Tyr  Asn  Ala  Lys  His  Glu  Thr  Val
          755                      760                 765

Asn  Val  Pro  Gly  Thr  Gly  Ser  Leu  Trp  Pro  Leu  Ser  Ala  Pro  Ser  Pro
     770                 775                      780

Ile  Gly  Lys  Cys  Ala  His  His  Ser  His  His  Phe  Ser  Leu  Asp  Ile  Asp
785                      790                 795                           800

Val  Gly  Cys  Thr  Asp  Leu  Asn  Glu  Asp  Leu  Gly  Val  Trp  Val  Ile  Phe
                    805                 810                           815

Lys  Ile  Lys  Thr  Gln  Asp  Gly  His  Ala  Arg  Leu  Gly  Asn  Leu  Glu  Phe
               820                 825                           830

Leu  Glu  Glu  Lys  Pro  Leu  Val  Gly  Glu  Ala  Leu  Ala  Arg  Val  Lys  Arg
          835                      840                 845

Ala  Glu  Lys  Lys  Trp  Arg  Asp  Lys  Arg  Glu  Lys  Leu  Glu  Trp  Glu  Thr
     850                 855                      860

Asn  Ile  Val  Tyr  Lys  Glu  Ala  Lys  Glu  Ser  Val  Asp  Ala  Leu  Phe  Val
865                      870                 875                           880
```

| | | | | | | | | | | | | | | |
|---|---|---|---|---|---|---|---|---|---|---|---|---|---|---|
| Asn | Ser | Gln | Tyr | Asp 885 | Arg | Leu | Gln | Ala | Asp 890 | Thr | Asn | Ile | Ala | Met 895 | Ile |
| His | Ala | Ala | Asp 900 | Lys | Arg | Val | His | Ser 905 | Ile | Arg | Glu | Ala | Tyr 910 | Leu | Pro |
| Glu | Leu | Ser 915 | Val | Ile | Pro | Gly | Val 920 | Asn | Ala | Ala | Ile | Phe 925 | Glu | Glu | Leu |
| Glu | Gly 930 | Arg | Ile | Phe | Thr | Ala 935 | Phe | Ser | Leu | Tyr | Asp 940 | Ala | Arg | Asn | Val |
| Ile 945 | Lys | Asn | Gly | Asp | Phe 950 | Asn | Asn | Gly | Leu | Ser 955 | Cys | Trp | Asn | Val | Lys 960 |
| Gly | His | Val | Asp | Val 965 | Glu | Glu | Gln | Asn | Asn 970 | His | Arg | Ser | Val | Leu 975 | Val |
| Val | Pro | Glu | Trp 980 | Glu | Ala | Glu | Val | Ser 985 | Gln | Glu | Val | Arg | Val 990 | Cys | Pro |
| Gly | Arg | Gly 995 | Tyr | Ile | Leu | Arg | Val 1000 | Thr | Ala | Tyr | Lys | Glu 1005 | Gly | Tyr | Gly |
| Glu | Gly | Cys 1010 | Val | Thr | Ile | His 1015 | Glu | Ile | Glu | Asn | Asn 1020 | Thr | Asp | Glu | Leu |
| Lys 1025 | Phe | Ser | Asn | Cys | Val 1030 | Glu | Glu | Glu | Val | Tyr 1035 | Pro | Asn | Asn | Thr | Val 1040 |
| Thr | Cys | Asn | Asp | Tyr 1045 | Thr | Ala | Thr | Gln | Glu 1050 | Glu | Tyr | Glu | Gly | Thr 1055 | Tyr |
| Thr | Ser | Arg | Asn 1060 | Arg | Gly | Tyr | Asp | Gly 1065 | Ala | Tyr | Glu | Ser | Asn 1070 | Ser | Ser |
| Val | Pro | Ala 1075 | Asp | Tyr | Ala | Ser | Ala 1080 | Tyr | Glu | Glu | Lys | Ala 1085 | Tyr | Thr | Asp |
| Gly | Arg 1090 | Arg | Asp | Asn | Pro | Cys 1095 | Glu | Ser | Asn | Arg | Gly 1100 | Tyr | Gly | Asp | Tyr |
| Thr 1105 | Pro | Leu | Pro | Ala | Gly 1110 | Tyr | Val | Thr | Lys | Glu 1115 | Leu | Glu | Tyr | Phe | Pro 1120 |
| Glu | Thr | Asp | Lys | Val 1125 | Trp | Ile | Glu | Ile | Gly 1130 | Glu | Thr | Glu | Gly | Thr 1135 | Phe |
| Ile | Val | Asp | Ser 1140 | Val | Glu | Leu | Leu | Leu 1145 | Met | Glu | Glu | | | | |

( 2 ) INFORMATION FOR SEQ ID NO:24:

( i ) SEQUENCE CHARACTERISTICS:
  ( A ) LENGTH: 3522 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:24:

```
ATGGAAAATA ATATTCAAAA TCAATGCGTA CCTTACAATT GTTTAAATAA TCCTGAAGTA      60
GAAATACTGA ACGAAGAACG CAGCACCGGC CGCCTGCCGC TGGACATCAG CCTGAGCCTT     120
ACACGTTTCC TTTTGAGTGA ATTTGTTCCA GGTGTGGGAG TTGCGTTTGG ATTATTTGAT     180
TTAATATGGG GTTTTATAAC TCCTTCTGAT TGGAGCTTAT TTCTTTTACA GATTGAACAA     240
TTGATTGAGC AAAGAATAGA AACATTGGAA AGGAACCGGG CAATTACTAC ATTACGAGGG     300
TTAGCAGATA GCTATGAAAT TTATATTGAA GCACTAAGAG AGTGGGAAGC AAATCCTAAT     360
AATGCACAAT TAAGGGAAGA TGTGCGTATT CGATTTGCTA ATACAGACGA CGCTTTAATA     420
ACAGCAATAA ATAATTTTAC ACTTACAAGT TTTGAAATCC CTCTTTTATC GGTCTATGTT     480
```

```
CAAGCGGCGA  ATTTACATTT  ATCACTATTA  AGAGACGCTG  TATCGTTTGG  GCAGGGTTGG   540
GGACTGGATA  TAGCTACTGT  TAATAATCAT  TATAATAGAT  TAATAAATCT  TATTCATAGA   600
TATACGAAAC  ATTGTTTGGA  CACATACAAT  CAAGGATTAG  AAAACTTAAG  AGGTACTAAT   660
ACTCGACAAT  GGGCAAGATT  CAATCAGTTT  AGGAGAGATT  TAACACTTAC  TGTATTAGAT   720
ATCGTTGCTC  TTTTTCCGAA  CTACGATGTT  AGAACATATC  CAATTCAAAC  GTCATCCCAA   780
TTAACAAGGG  AAATTTATAC  AAGTTCAGTA  ATTGAGGATT  CTCCAGTTTC  TGCTAATATA   840
CCTAATGGTT  TTAATAGGGC  GGAATTTGGA  GTTAGACCGC  CCCATCTTAT  GGACTTTATG   900
AATTCTTTGT  TTGTAACTGC  AGAGACTGTT  AGAAGTCAAA  CTGTGTGGGG  AGGACACTTA   960
GTTAGTTCAC  GAAATACGGC  TGGTAACCGT  ATAAATTTCC  CTAGTTACGG  GGTCTTCAAT  1020
CCTGGTGGCG  CCATTTGGAT  TGCAGATGAG  GATCCACGTC  CTTTTTATCG  GACATTATCA  1080
GATCCTGTTT  TTGTCCGAGG  AGGATTTGGG  AATCCTCATT  ATGTACTGGG  GCTTAGGGGA  1140
GTAGCATTTC  AACAAACTGG  TACGAACCAC  ACCCGAACAT  TTAGAAATAG  TGGGACCATA  1200
GATTCTCTAG  ATGAAATCCC  ACCTCAGGAT  AATAGTGGGG  CACCTTGGAA  TGATTATAGT  1260
CATGTATTAA  ATCATGTTAC  ATTTGTACGA  TGGCCAGGTG  AGATTTCAGG  AAGTGATTCA  1320
TGGAGAGCTC  CAATGTTTTC  TTGGACGCAC  CGTAGTGCAA  CCCCTACAAA  TACAATTGAT  1380
CCGGAGAGGA  TTACTCAAAT  ACCATTGGTA  AAAGCACATA  CACTTCAGTC  AGGTACTACT  1440
GTTGTAAGAG  GGCCCGGGTT  TACGGGAGGA  GATATTCTTC  GACGAACAAG  TGGAGGACCA  1500
TTTGCTTATA  CTATTGTTAA  TATAAATGGG  CAATTACCCC  AAAGGTATCG  TGCAAGAATA  1560
CGCTATGCCT  CTACTACAAA  TCTAAGAATT  TACGTAACGG  TTGCAGGTGA  ACGGATTTTT  1620
GCTGGTCAAT  TTAACAAAAC  AATGGATACC  GGTGACCCAT  TAACATTCCA  ATCTTTTAGT  1680
TACGCAACTA  TTAATACAGC  TTTTACATTC  CCAATGAGCC  AGAGTAGTTT  CACAGTAGGT  1740
GCTGATACTT  TTAGTTCAGG  GAATGAAGTT  TATATAGACA  GATTTGAATT  GATTCCAGTT  1800
ACTGCAACAT  TTGAAGCAGA  ATATGATTTA  GAAAGAGCAC  AAAAGGCGGT  GAATGCGCTG  1860
TTTACTTCTA  TAAACCAAAT  AGGGATAAAA  ACAGATGTGA  CGGATTATCA  TATTGATCAA  1920
GTATCCAATT  TAGTGGATTG  TTTATCAGAT  GAATTTTGTC  TGGATGAAAA  GCGAGAATTG  1980
TCCGAGAAAG  TCAAACATGC  GAAGCGACTC  AGTGATGAGC  GGAATTTACT  TCAAGATCCA  2040
AACTTCAAAG  GCATCAATAG  GCAACTAGAC  CGTGGTTGGA  GAGGAAGTAC  GGATATTACC  2100
ATCCAAAGAG  GAGATGACGT  ATTCAAAGAA  AATTATGTCA  CACTACCAGG  TACCTTTGAT  2160
GAGTGCTATC  CAACGTATTT  ATATCAAAAA  ATAGATGAGT  CGAAATTAAA  ACCCTATACT  2220
CGTTATCAAT  TAAGAGGGTA  TATCGAGGAT  AGTCAAGACT  TAGAAATCTA  TTTGATCCGC  2280
TATAATGCAA  AACACGAAAC  AGTAAATGTG  CTAGGTACGG  GTTCTTTATG  GCCGCTTTCA  2340
GTCCAAAGTC  CAATCAGAAA  GTGTGGAGAA  CCGAATCGAT  GCGCGCCACA  CCTTGAATGG  2400
AATCCTGATC  TAGATTGTTC  CTGCAGAGAC  GGGGAAAAAT  GTGCACATCA  TTCGCATCAT  2460
TTCTCCTTGG  ACATTGATGT  TGGATGTACA  GACTTAAATG  AGGACTTAGA  TGTATGGGTG  2520
ATATTCAAGA  TTAAGACGCA  AGATGGCCAT  GCAAGACTAG  GAAATCTAGA  GTTTCTCGAA  2580
GAGAAACCAT  TAGTCGGGGA  AGCACTAGCT  CGTGTGAAAA  GAGCAGAGAA  AAAATGGAGA  2640
GATAAACGTG  AAAAATTGGA  ATTGGAAACA  AATATTGTTT  ATAAAGAGGC  AAAAGAATCT  2700
GTAGATGCTT  TATTTGTAAA  CTCTCAATAT  GATCAATTAC  AAGCGGATAC  GAATATTGCC  2760
ATGATTCATG  CGGCAGATAA  ACGTGTTCAT  AGAATTCGGG  AAGCGTATCT  TCCAGAGTTA  2820
TCTGTGATTC  CGGGTGTAAA  TGTAGACATT  TTCGAAGAAT  TAAAAGGGCG  TATTTTCACT  2880
```

```
GCATTCTTCC TATATGATGC GAGAAATGTC ATTAAAAACG GTGATTTCAA TAATGGCTTA      2940

TCATGCTGGA ACGTGAAAGG GCATGTAGAT GTAGAAGAAC AAAACAACCA CCGTTCGGTC      3000

CTTGTTGTTC CGGAATGGGA AGCAGAAGTG TCACAAGAAG TTCGTGTCTG TCCGGGTCGT      3060

GGCTATATCC TTCGTGTCAC AGCGTACAAG GAGGGATATG GAGAAGGTTG CGTAACCATT      3120

CATGAGATCG AGAACAATAC AGACGAACTG AAGTTTAGCA ACTGCGTAGA AGAGGAAGTC      3180

TATCCAAACA ACACGGTAAC GTGTAATGAT TATACTGCAA ATCAAGAAGA ATACGGGGGT      3240

GCGTACACTT CCCGTAATCG TGGATATGAC GAAACTTATG GAAGCAATTC TTCTGTACCA      3300

GCTGATTATG CGTCAGTCTA TGAAGAAAAA TCGTATACAG ATGGACGAAG AGACAATCCT      3360

TGTGAATCTA ACAGAGGATA TGGGGATTAC ACACCACTAC CAGCTGGCTA TGTGACAAAA      3420

GAATTAGAGT ACTTCCCAGA AACCGATAAG GTATGGATTG AGATCGGAGA AACGGAAGGA      3480

ACATTCATCG TGGACAGCGT GGAATTACTC CTTATGGAGG AA                         3522
```

( 2 ) INFORMATION FOR SEQ ID NO:25:

( i ) SEQUENCE CHARACTERISTICS:
        ( A ) LENGTH: 1174 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:25:

```
Met Glu Asn Asn Ile Gln Asn Gln Cys Val Pro Tyr Asn Cys Leu Asn
  1               5                  10                  15

Asn Pro Glu Val Glu Ile Leu Asn Glu Glu Arg Ser Thr Gly Arg Leu
             20                  25                  30

Pro Leu Asp Ile Ser Leu Ser Leu Thr Arg Phe Leu Leu Ser Glu Phe
         35                  40                  45

Val Pro Gly Val Gly Val Ala Phe Gly Leu Phe Asp Leu Ile Trp Gly
     50                  55                  60

Phe Ile Thr Pro Ser Asp Trp Ser Leu Phe Leu Leu Gln Ile Glu Gln
 65                  70                  75                  80

Leu Ile Glu Gln Arg Ile Glu Thr Leu Glu Arg Asn Arg Ala Ile Thr
                 85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
                165                 170                 175

Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
        195                 200                 205

Tyr Asn Gln Gly Leu Glu Asn Leu Arg Gly Thr Asn Thr Arg Gln Trp
    210                 215                 220

Ala Arg Phe Asn Gln Phe Arg Arg Asp Leu Thr Leu Thr Val Leu Asp
225                 230                 235                 240
```

```
Ile Val Ala Leu Phe Pro Asn Tyr Asp Val Arg Thr Tyr Pro Ile Gln
            245                 250                 255

Thr Ser Ser Gln Leu Thr Arg Glu Ile Tyr Thr Ser Ser Val Ile Glu
            260                 265                 270

Asp Ser Pro Val Ser Ala Asn Ile Pro Asn Gly Phe Asn Arg Ala Glu
            275                 280                 285

Phe Gly Val Arg Pro Pro His Leu Met Asp Phe Met Asn Ser Leu Phe
            290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Arg Ile Asn Phe Pro Ser Tyr
            325                 330                 335

Gly Val Phe Asn Pro Gly Gly Ala Ile Trp Ile Ala Asp Glu Asp Pro
            340                 345                 350

Arg Pro Phe Tyr Arg Thr Leu Ser Asp Pro Val Phe Val Arg Gly Gly
            355                 360                 365

Phe Gly Asn Pro His Tyr Val Leu Gly Leu Arg Gly Val Ala Phe Gln
            370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
            405                 410                 415

Asn Asp Tyr Ser His Val Leu Asn His Val Thr Phe Val Arg Trp Pro
            420                 425                 430

Gly Glu Ile Ser Gly Ser Asp Ser Trp Arg Ala Pro Met Phe Ser Trp
            435                 440                 445

Thr His Arg Ser Ala Thr Pro Thr Asn Thr Ile Asp Pro Glu Arg Ile
            450                 455                 460

Thr Gln Ile Pro Leu Val Lys Ala His Thr Leu Gln Ser Gly Thr Thr
465                 470                 475                 480

Val Val Arg Gly Pro Gly Phe Thr Gly Gly Asp Ile Leu Arg Arg Thr
            485                 490                 495

Ser Gly Gly Pro Phe Ala Tyr Thr Ile Val Asn Ile Asn Gly Gln Leu
            500                 505                 510

Pro Gln Arg Tyr Arg Ala Arg Ile Arg Tyr Ala Ser Thr Thr Asn Leu
            515                 520                 525

Arg Ile Tyr Val Thr Val Ala Gly Glu Arg Ile Phe Ala Gly Gln Phe
            530                 535                 540

Asn Lys Thr Met Asp Thr Gly Asp Pro Leu Thr Phe Gln Ser Phe Ser
545                 550                 555                 560

Tyr Ala Thr Ile Asn Thr Ala Phe Thr Phe Pro Met Ser Gln Ser Ser
            565                 570                 575

Phe Thr Val Gly Ala Asp Thr Phe Ser Ser Gly Asn Glu Val Tyr Ile
            580                 585                 590

Asp Arg Phe Glu Leu Ile Pro Val Thr Ala Thr Phe Glu Ala Glu Tyr
            595                 600                 605

Asp Leu Glu Arg Ala Gln Lys Ala Val Asn Ala Leu Phe Thr Ser Ile
            610                 615                 620

Asn Gln Ile Gly Ile Lys Thr Asp Val Thr Asp Tyr His Ile Asp Gln
625                 630                 635                 640

Val Ser Asn Leu Val Asp Cys Leu Ser Asp Glu Phe Cys Leu Asp Glu
            645                 650                 655

Lys Arg Glu Leu Ser Glu Lys Val Lys His Ala Lys Arg Leu Ser Asp
```

-continued

|     |     |     |     |     |     |     |     |     |     |     |     |     |     |     |
|---|---|---|---|---|---|---|---|---|---|---|---|---|---|---|
| | | | | 660 | | | | 665 | | | | 670 | | |
| Glu | Arg | Asn | Leu | Leu | Gln | Asp | Pro | Asn | Phe | Lys | Gly | Ile | Asn | Arg | Gln |
| | | 675 | | | | | 680 | | | | | 685 | | | |
| Leu | Asp | Arg | Gly | Trp | Arg | Gly | Ser | Thr | Asp | Ile | Thr | Ile | Gln | Arg | Gly |
| | | 690 | | | | | 695 | | | | | 700 | | | |
| Asp | Asp | Val | Phe | Lys | Glu | Asn | Tyr | Val | Thr | Leu | Pro | Gly | Thr | Phe | Asp |
| 705 | | | | | | 710 | | | | | 715 | | | | 720 |
| Glu | Cys | Tyr | Pro | Thr | Tyr | Leu | Tyr | Gln | Lys | Ile | Asp | Glu | Ser | Lys | Leu |
| | | | | 725 | | | | | 730 | | | | | 735 | |
| Lys | Pro | Tyr | Thr | Arg | Tyr | Gln | Leu | Arg | Gly | Tyr | Ile | Glu | Asp | Ser | Gln |
| | | | 740 | | | | | 745 | | | | | 750 | | |
| Asp | Leu | Glu | Ile | Tyr | Leu | Ile | Arg | Tyr | Asn | Ala | Lys | His | Glu | Thr | Val |
| | | | 755 | | | | | 760 | | | | | 765 | | |
| Asn | Val | Leu | Gly | Thr | Gly | Ser | Leu | Trp | Pro | Leu | Ser | Val | Gln | Ser | Pro |
| | 770 | | | | | 775 | | | | | 780 | | | | |
| Ile | Arg | Lys | Cys | Gly | Glu | Pro | Asn | Arg | Cys | Ala | Pro | His | Leu | Glu | Trp |
| 785 | | | | | 790 | | | | | 795 | | | | | 800 |
| Asn | Pro | Asp | Leu | Asp | Cys | Ser | Cys | Arg | Asp | Gly | Glu | Lys | Cys | Ala | His |
| | | | | 805 | | | | | 810 | | | | | 815 | |
| His | Ser | His | His | Phe | Ser | Leu | Asp | Ile | Asp | Val | Gly | Cys | Thr | Asp | Leu |
| | | | 820 | | | | | 825 | | | | | 830 | | |
| Asn | Glu | Asp | Leu | Asp | Val | Trp | Val | Ile | Phe | Lys | Ile | Lys | Thr | Gln | Asp |
| | | 835 | | | | | 840 | | | | | 845 | | | |
| Gly | His | Ala | Arg | Leu | Gly | Asn | Leu | Glu | Phe | Leu | Glu | Glu | Lys | Pro | Leu |
| | | 850 | | | | | 855 | | | | | 860 | | | |
| Val | Gly | Glu | Ala | Leu | Ala | Arg | Val | Lys | Arg | Ala | Glu | Lys | Lys | Trp | Arg |
| 865 | | | | | 870 | | | | | 875 | | | | | 880 |
| Asp | Lys | Arg | Glu | Lys | Leu | Glu | Leu | Glu | Thr | Asn | Ile | Val | Tyr | Lys | Glu |
| | | | | 885 | | | | | 890 | | | | | 895 | |
| Ala | Lys | Glu | Ser | Val | Asp | Ala | Leu | Phe | Val | Asn | Ser | Gln | Tyr | Asp | Gln |
| | | | 900 | | | | | 905 | | | | | 910 | | |
| Leu | Gln | Ala | Asp | Thr | Asn | Ile | Ala | Met | Ile | His | Ala | Ala | Asp | Lys | Arg |
| | | 915 | | | | | 920 | | | | | 925 | | | |
| Val | His | Arg | Ile | Arg | Glu | Ala | Tyr | Leu | Pro | Glu | Leu | Ser | Val | Ile | Pro |
| | | 930 | | | | | 935 | | | | | 940 | | | |
| Gly | Val | Asn | Val | Asp | Ile | Phe | Glu | Glu | Leu | Lys | Gly | Arg | Ile | Phe | Thr |
| 945 | | | | | 950 | | | | | 955 | | | | | 960 |
| Ala | Phe | Phe | Leu | Tyr | Asp | Ala | Arg | Asn | Val | Ile | Lys | Asn | Gly | Asp | Phe |
| | | | | 965 | | | | | 970 | | | | | 975 | |
| Asn | Asn | Gly | Leu | Ser | Cys | Trp | Asn | Val | Lys | Gly | His | Val | Asp | Val | Glu |
| | | | 980 | | | | | 985 | | | | | 990 | | |
| Glu | Gln | Asn | Asn | His | Arg | Ser | Val | Leu | Val | Val | Pro | Glu | Trp | Glu | Ala |
| | | 995 | | | | | 1000 | | | | | 1005 | | | |
| Glu | Val | Ser | Gln | Glu | Val | Arg | Val | Cys | Pro | Gly | Arg | Gly | Tyr | Ile | Leu |
| | 1010 | | | | | 1015 | | | | | 1020 | | | | |
| Arg | Val | Thr | Ala | Tyr | Lys | Glu | Gly | Tyr | Gly | Glu | Gly | Cys | Val | Thr | Ile |
| 1025 | | | | | 1030 | | | | | 1035 | | | | | 1040 |
| His | Glu | Ile | Glu | Asn | Asn | Thr | Asp | Glu | Leu | Lys | Phe | Ser | Asn | Cys | Val |
| | | | | 1045 | | | | | 1050 | | | | | 1055 | |
| Glu | Glu | Glu | Val | Tyr | Pro | Asn | Asn | Thr | Val | Thr | Cys | Asn | Asp | Tyr | Thr |
| | | | 1060 | | | | | 1065 | | | | | 1070 | | |
| Ala | Asn | Gln | Glu | Glu | Tyr | Gly | Gly | Ala | Tyr | Thr | Ser | Arg | Asn | Arg | Gly |
| | | 1075 | | | | | 1080 | | | | | 1085 | | | |

```
                Tyr   Asp   Glu   Thr   Tyr   Gly   Ser   Asn   Ser   Ser   Val   Pro   Ala   Asp   Tyr   Ala
                      1090                    1095                          1100

Ser   Val   Tyr   Glu   Glu   Lys   Ser   Tyr   Thr   Asp   Gly   Arg   Arg   Asp   Asn   Pro
                1105                          1110                    1115                                1120

Cys   Glu   Ser   Asn   Arg   Gly   Tyr   Gly   Asp   Tyr   Thr   Pro   Leu   Pro   Ala   Gly
                                  1125                          1130                          1135

Tyr   Val   Thr   Lys   Glu   Leu   Glu   Tyr   Phe   Pro   Glu   Thr   Asp   Lys   Val   Trp
                                  1140                          1145                          1150

Ile   Glu   Ile   Gly   Glu   Thr   Gly   Gly   Thr   Phe   Ile   Val   Asp   Ser   Val   Glu
                                  1155                          1160                          1165

Leu   Leu   Leu   Met   Glu   Glu
                                  1170
```

( 2 ) INFORMATION FOR SEQ ID NO:26:

( i ) SEQUENCE CHARACTERISTICS:
       ( A ) LENGTH: 3444 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:26:

```
ATGGAAAATA   ATATTCAAAA   TCAATGCGTA   CCTTACAATT   GTTTAAATAA   TCCTGAAGTA    60

GAAATACTGA   ACGAAGAACG   CAGCACCGGC   CGCCTGCCGC   TGGACATCAG   CCTGAGCCTT   120

ACACGTTTCC   TTTTGAGTGA   ATTTGTTCCA   GGTGTGGGAG   TTGCGTTTGG   ATTATTTGAT   180

TTAATATGGG   GTTTTATAAC   TCCTTCTGAT   TGGAGCTTAT   TTCTTTTACA   GATTGAACAA   240

TTGATTGAGC   AAAGAATAGA   AACATTGGAA   AGGAACCGGG   CAATTACTAC   ATTACGAGGG   300

TTAGCAGATA   GCTATGAAAT   TTATATTGAA   GCACTAAGAG   AGTGGGAAGC   AAATCCTAAT   360

AATGCACAAT   TAAGGGAAGA   TGTGCGTATT   CGATTTGCTA   ATACAGACGA   CGCTTTAATA   420

ACAGCAATAA   ATAATTTTAC   ACTTACAAGT   TTTGAAATCC   CTCTTTTATC   GGTCTATGTT   480

CAAGCGGCGA   ATTTACATTT   ATCACTATTA   AGAGACGCTG   TATCGTTTGG   GCAGGGTTGG   540

GGACTGGATA   TAGCTACTGT   TAATAATCAT   TATAATAGAT   TAATAAATCT   TATTCATAGA   600

TATACGAAAC   ATTGTTTGGA   CACATACAAT   CAAGGATTAG   AAAACTTAAG   AGGTACTAAT   660

ACTCGACAAT   GGGCAAGATT   CAATCAGTTT   AGGAGAGATT   TAACACTTAC   TGTATTAGAT   720

ATCGTTGCTC   TTTTTCCGAA   CTACGATGTT   AGAACATATC   CAATTCAAAC   GTCATCCCAA   780

TTAACAAGGG   AAATTTATAC   AAGTTCAGTA   ATTGAGGATT   CTCCAGTTTC   TGCTAATATA   840

CCTAATGGTT   TAATAGGGC   GGAATTTGGA   GTTAGACCGC   CCATCTTAT   GGACTTTATG   900

AATTCTTTGT   TTGTAACTGC   AGAGACTGTT   AGAAGTCAAA   CTGTGTGGGG   AGGACACTTA   960

GTTAGTTCAC   GAAATACGGC   TGGTAACCGT   ATAAATTTCC   CTAGTTACGG   GGTCTTCAAT   1020

CCTGGTGGCG   CCATTTGGAT   TGCAGATGAG   GATCCACGTC   CTTTTTATCG   GACATTATCA   1080

GATCCTGTTT   TTGTCCGAGG   AGGATTTGGG   AATCCTCATT   ATGTACTGGG   GCTTAGGGGA   1140

GTAGCATTTC   AACAAACTGG   TACGAACCAC   ACCCGAACAT   TTAGAAATAG   TGGGACCATA   1200

GATTCTCTAG   ATGAAATCCC   ACCTCAGGAT   AATAGTGGGG   CACCTTGGAA   TGATTATAGT   1260

CATGTATTAA   ATCATGTTAC   ATTTGTACGA   TGGCCAGGTG   AGATTTCAGG   AAGTGATTCA   1320

TGGAGAGCTC   CAATGTTTTC   TTGGACGCAC   CGTAGTGCAA   CCCCTACAAA   TACAATTGAT   1380

CCGGAGAGGA   TTACTCAAAT   ACCATTGGTA   AAAGCACATA   CACTTCAGTC   AGGTACTACT   1440

GTTGTAAGAG   GGCCCGGGTT   TACGGGAGGA   GATATTCTTC   GACGAACAAG   TGGAGGACCA   1500
```

|                |                |                |                |                |                |      |
|----------------|----------------|----------------|----------------|----------------|----------------|------|
| TTTGCTTATA     | CTATTGTTAA     | TATAAATGGG     | CAATTACCCC     | AAAGGTATCG     | TGCAAGAATA     | 1560 |
| CGCTATGCCT     | CTACTACAAA     | TCTAAGAATT     | TACGTAACGG     | TTGCAGGTGA     | ACGGATTTTT     | 1620 |
| GCTGGTCAAT     | TTAACAAAAC     | AATGGATACC     | GGTGACCCAT     | TAACATTCCA     | ATCTTTTAGT     | 1680 |
| TACGCAACTA     | TTAATACAGC     | TTTTACATTC     | CCAATGAGCC     | AGAGTAGTTT     | CACAGTAGGT     | 1740 |
| GCTGATACTT     | TTAGTTCAGG     | GAATGAAGTT     | TATATAGACA     | GATTTGAATT     | GATTCCAGTT     | 1800 |
| ACTGCAACAT     | TTGAAGCAGA     | ATATGATTTA     | GAAAGAGCAC     | AAAAGGCGGT     | GAATGCGCTG     | 1860 |
| TTTACTTCTA     | TAAACCAAAT     | AGGGATAAAA     | ACAGATGTGA     | CGGATTATCA     | TATCGATCGA     | 1920 |
| GTATCCAATT     | TAGTTGAGTG     | TTTATCTGAT     | GAATTTGTC      | TGGATGAAAA     | AAAAGAATTG     | 1980 |
| TCCGAGAAAG     | TCAAACATGC     | GAAGCGACTT     | AGTGATGAGC     | GGAATTTACT     | TCAAGATCCA     | 2040 |
| AACTTTAGAG     | GGATCAATAG     | ACAACTAGAC     | CGTGGCTGGA     | GAGGAAGTAC     | GGATATTACC     | 2100 |
| ATCCAAGGAG     | GCGATGACGT     | ATTCAAAGAG     | AATTACGTTA     | CGCTATTGGG     | TACCTTTGAT     | 2160 |
| GAGTGCTATC     | CAACGTATTT     | ATATCAAAAA     | ATAGATGAGT     | CGAAATTAAA     | AGCCTATACC     | 2220 |
| CGTTACCAAT     | TAAGAGGGTA     | TATCGAAGAT     | AGTCAAGACT     | TAGAAATCTA     | TTTAATTCGC     | 2280 |
| TACAATGCCA     | AACACGAAAC     | AGTAAATGTG     | CCAGGTACGG     | GTTCCTTATG     | GCCGCTTTCA     | 2340 |
| GCCCCAAGTC     | CAATCGGAAA     | ATGTGCCCAT     | CATTCCCATC     | ATTTCTCCTT     | GGACATTGAT     | 2400 |
| GTTGGATGTA     | CAGACTTAAA     | TGAGGACTTA     | GGTGTATGGG     | TGATATTCAA     | GATTAAGACG     | 2460 |
| CAAGATGGCC     | ATGCAAGACT     | AGGAAATCTA     | GAATTTCTCG     | AAGAGAAACC     | ATTAGTAGGA     | 2520 |
| GAAGCACTAG     | CTCGTGTGAA     | AAGAGCGGAG     | AAAAAATGGA     | GAGACAAACG     | TGAAAAATTG     | 2580 |
| GAATGGGAAA     | CAAATATTGT     | TTATAAAGAG     | GCAAAGAAT      | CTGTAGATGC     | TTTATTTGTA     | 2640 |
| AACTCTCAAT     | ATGATAGATT     | ACAAGCGGAT     | ACCAACATCG     | CGATGATTCA     | TGCGGCAGAT     | 2700 |
| AAACGCGTTC     | ATAGCATTCG     | AGAAGCTTAT     | CTGCCTGAGC     | TGTCTGTGAT     | TCCGGGTGTC     | 2760 |
| AATGCGGCTA     | TTTTTGAAGA     | ATTAGAAGGG     | CGTATTTTCA     | CTGCATTCTC     | CCTATATGAT     | 2820 |
| GCGAGAAATG     | TCATTAAAAA     | TGGTGATTTT     | AATAATGGCT     | TATCCTGCTG     | GAACGTGAAA     | 2880 |
| GGGCATGTAG     | ATGTAGAAGA     | ACAAAACAAC     | CACCGTTCGG     | TCCTTGTTGT     | TCCGGAATGG     | 2940 |
| GAAGCAGAAG     | TGTCACAAGA     | AGTTCGTGTC     | TGTCCGGGTC     | GTGGCTATAT     | CCTTCGTGTC     | 3000 |
| ACAGCGTACA     | AGGAGGGATA     | TGGAGAAGGT     | TGCGTAACCA     | TTCATGAGAT     | CGAGAACAAT     | 3060 |
| ACAGACGAAC     | TGAAGTTTAG     | CAACTGTGTA     | GAAGAGGAAG     | TATATCCAAA     | CAACACGGTA     | 3120 |
| ACGTGTAATG     | ATTATACTGC     | GACTCAAGAA     | GAATATGAGG     | GTACGTACAC     | TTCTCGTAAT     | 3180 |
| CGAGGATATG     | ACGGAGCCTA     | TGAAAGCAAT     | TCTTCTGTAC     | CAGCTGATTA     | TGCATCAGCC     | 3240 |
| TATGAAGAAA     | AAGCATATAC     | AGATGGACGA     | AGAGACAATC     | CTTGTGAATC     | TAACAGAGGA     | 3300 |
| TATGGGGATT     | ACACACCACT     | ACCAGCTGGC     | TATGTGACAA     | AAGAATTAGA     | GTACTTCCCA     | 3360 |
| GAAACCGATA     | AGGTATGGAT     | TGAGATCGGA     | GAAACGGAAG     | GAACATTCAT     | CGTGGACAGC     | 3420 |
| GTGGAATTAC     | TTCTTATGGA     | GGAA           |                |                |                | 3444 |

( 2 ) INFORMATION FOR SEQ ID NO:27:

( i ) SEQUENCE CHARACTERISTICS:
        ( A ) LENGTH: 1148 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:27:

-continued

| | | | | | | | | | | | | | | |
|---|---|---|---|---|---|---|---|---|---|---|---|---|---|---|
| Met 1 | Glu | Asn | Asn | Ile 5 | Gln | Asn | Gln | Cys | Val 10 | Pro | Tyr | Asn | Cys | Leu 15 | Asn |
| Asn | Pro | Glu | Val 20 | Glu | Ile | Leu | Asn | Glu 25 | Arg | Ser | Thr | Gly 30 | Arg | Leu |
| Pro | Leu | Asp 35 | Ile | Ser | Leu | Ser | Leu 40 | Thr | Arg | Phe | Leu | Leu 45 | Ser | Glu | Phe |
| Val | Pro 50 | Gly | Val | Gly | Val 55 | Ala | Phe | Gly | Leu | Phe 60 | Asp | Leu | Ile | Trp | Gly |
| Phe 65 | Ile | Thr | Pro | Ser | Asp 70 | Trp | Ser | Leu | Phe 75 | Leu | Gln | Ile | Glu | Gln 80 |
| Leu | Ile | Glu | Gln | Arg 85 | Ile | Glu | Thr | Leu | Glu 90 | Arg | Asn | Arg | Ala | Ile 95 | Thr |
| Thr | Leu | Arg | Gly 100 | Leu | Ala | Asp | Ser | Tyr 105 | Glu | Ile | Tyr | Ile 110 | Glu | Ala | Leu |
| Arg | Glu | Trp 115 | Glu | Ala | Asn | Pro | Asn 120 | Asn | Ala | Gln | Leu | Arg 125 | Glu | Asp | Val |
| Arg | Ile 130 | Arg | Phe | Ala | Asn | Thr 135 | Asp | Asp | Ala | Leu | Ile 140 | Thr | Ala | Ile | Asn |
| Asn 145 | Phe | Thr | Leu | Thr | Ser 150 | Phe | Glu | Ile | Pro | Leu 155 | Leu | Ser | Val | Tyr | Val 160 |
| Gln | Ala | Ala | Asn | Leu 165 | His | Leu | Ser | Leu | Leu 170 | Arg | Asp | Ala | Val | Ser 175 | Phe |
| Gly | Gln | Gly | Trp 180 | Gly | Leu | Asp | Ile | Ala 185 | Thr | Val | Asn | Asn | His 190 | Tyr | Asn |
| Arg | Leu | Ile 195 | Asn | Leu | Ile | His | Arg 200 | Tyr | Thr | Lys | His | Cys 205 | Leu | Asp | Thr |
| Tyr | Asn 210 | Gln | Gly | Leu | Glu | Asn 215 | Leu | Arg | Gly | Thr | Asn 220 | Thr | Arg | Gln | Trp |
| Ala 225 | Arg | Phe | Asn | Gln | Phe 230 | Arg | Arg | Asp | Leu | Thr 235 | Leu | Thr | Val | Leu | Asp 240 |
| Ile | Val | Ala | Leu | Phe 245 | Pro | Asn | Tyr | Asp | Val 250 | Arg | Thr | Tyr | Pro | Ile 255 | Gln |
| Thr | Ser | Ser | Gln 260 | Leu | Thr | Arg | Glu | Ile 265 | Tyr | Thr | Ser | Ser | Val 270 | Ile | Glu |
| Asp | Ser | Pro 275 | Val | Ser | Ala | Asn | Ile 280 | Pro | Asn | Gly | Phe | Asn 285 | Arg | Ala | Glu |
| Phe | Gly 290 | Val | Arg | Pro | Pro | His 295 | Leu | Met | Asp | Phe | Met 300 | Asn | Ser | Leu | Phe |
| Val 305 | Thr | Ala | Glu | Thr | Val 310 | Arg | Ser | Gln | Thr | Val 315 | Trp | Gly | Gly | His | Leu 320 |
| Val | Ser | Ser | Arg | Asn 325 | Thr | Ala | Gly | Asn | Arg 330 | Ile | Asn | Phe | Pro | Ser 335 | Tyr |
| Gly | Val | Phe | Asn 340 | Pro | Gly | Gly | Ala | Ile 345 | Trp | Ile | Ala | Asp | Glu 350 | Asp | Pro |
| Arg | Pro | Phe 355 | Tyr | Arg | Thr | Leu | Ser 360 | Asp | Pro | Val | Phe | Val 365 | Arg | Gly | Gly |
| Phe | Gly 370 | Asn | Pro | His | Tyr | Val 375 | Leu | Gly | Leu | Arg | Gly 380 | Val | Ala | Phe | Gln |
| Gln 385 | Thr | Gly | Thr | Asn | His 390 | Thr | Arg | Thr | Phe | Arg 395 | Asn | Ser | Gly | Thr | Ile 400 |
| Asp | Ser | Leu | Asp | Glu 405 | Ile | Pro | Pro | Gln | Asp 410 | Asn | Ser | Gly | Ala | Pro 415 | Trp |
| Asn | Asp | Tyr | Ser | His 420 | Val | Leu | Asn | His | Val 425 | Thr | Phe | Val | Arg | Trp 430 | Pro |

```
Gly  Glu  Ile  Ser  Gly  Ser  Asp  Ser  Trp  Arg  Ala  Pro  Met  Phe  Ser  Trp
          435                     440                     445

Thr  His  Arg  Ser  Ala  Thr  Pro  Thr  Asn  Thr  Ile  Asp  Pro  Glu  Arg  Ile
          450                     455                     460

Thr  Gln  Ile  Pro  Leu  Val  Lys  Ala  His  Thr  Leu  Gln  Ser  Gly  Thr  Thr
465                      470                     475                          480

Val  Val  Arg  Gly  Pro  Gly  Phe  Thr  Gly  Gly  Asp  Ile  Leu  Arg  Arg  Thr
                    485                     490                          495

Ser  Gly  Gly  Pro  Phe  Ala  Tyr  Thr  Ile  Val  Asn  Ile  Asn  Gly  Gln  Leu
                    500                     505                     510

Pro  Gln  Arg  Tyr  Arg  Ala  Arg  Ile  Arg  Tyr  Ala  Ser  Thr  Thr  Asn  Leu
          515                     520                     525

Arg  Ile  Tyr  Val  Thr  Val  Ala  Gly  Glu  Arg  Ile  Phe  Ala  Gly  Gln  Phe
          530                     535                     540

Asn  Lys  Thr  Met  Asp  Thr  Gly  Asp  Pro  Leu  Thr  Phe  Gln  Ser  Phe  Ser
545                      550                     555                          560

Tyr  Ala  Thr  Ile  Asn  Thr  Ala  Phe  Thr  Phe  Pro  Met  Ser  Gln  Ser  Ser
                    565                     570                     575

Phe  Thr  Val  Gly  Ala  Asp  Thr  Phe  Ser  Ser  Gly  Asn  Glu  Val  Tyr  Ile
                    580                     585                     590

Asp  Arg  Phe  Glu  Leu  Ile  Pro  Val  Thr  Ala  Thr  Phe  Glu  Ala  Glu  Tyr
          595                     600                     605

Asp  Leu  Glu  Arg  Ala  Gln  Lys  Ala  Val  Asn  Ala  Leu  Phe  Thr  Ser  Ile
          610                     615                     620

Asn  Gln  Ile  Gly  Ile  Lys  Thr  Asp  Val  Thr  Asp  Tyr  His  Ile  Asp  Arg
625                      630                     635                          640

Val  Ser  Asn  Leu  Val  Glu  Cys  Leu  Ser  Asp  Glu  Phe  Cys  Leu  Asp  Glu
                    645                     650                          655

Lys  Lys  Glu  Leu  Ser  Glu  Lys  Val  Lys  His  Ala  Lys  Arg  Leu  Ser  Asp
                    660                     665                     670

Glu  Arg  Asn  Leu  Leu  Gln  Asp  Pro  Asn  Phe  Arg  Gly  Ile  Asn  Arg  Gln
          675                     680                     685

Leu  Asp  Arg  Gly  Trp  Arg  Gly  Ser  Thr  Asp  Ile  Thr  Ile  Gln  Gly  Gly
          690                     695                     700

Asp  Asp  Val  Phe  Lys  Glu  Asn  Tyr  Val  Thr  Leu  Leu  Gly  Thr  Phe  Asp
705                      710                     715                          720

Glu  Cys  Tyr  Pro  Thr  Tyr  Leu  Tyr  Gln  Lys  Ile  Asp  Glu  Ser  Lys  Leu
                    725                     730                     735

Lys  Ala  Tyr  Thr  Arg  Tyr  Gln  Leu  Arg  Gly  Tyr  Ile  Glu  Asp  Ser  Gln
                    740                     745                     750

Asp  Leu  Glu  Ile  Tyr  Leu  Ile  Arg  Tyr  Asn  Ala  Lys  His  Glu  Thr  Val
          755                     760                     765

Asn  Val  Pro  Gly  Thr  Gly  Ser  Leu  Trp  Pro  Leu  Ser  Ala  Pro  Ser  Pro
          770                     775                     780

Ile  Gly  Lys  Cys  Ala  His  His  Ser  His  His  Phe  Ser  Leu  Asp  Ile  Asp
785                      790                     795                          800

Val  Gly  Cys  Thr  Asp  Leu  Asn  Glu  Asp  Leu  Gly  Val  Trp  Val  Ile  Phe
                    805                     810                          815

Lys  Ile  Lys  Thr  Gln  Asp  Gly  His  Ala  Arg  Leu  Gly  Asn  Leu  Glu  Phe
                    820                     825                     830

Leu  Glu  Glu  Lys  Pro  Leu  Val  Gly  Glu  Ala  Leu  Ala  Arg  Val  Lys  Arg
          835                     840                     845

Ala  Glu  Lys  Lys  Trp  Arg  Asp  Lys  Arg  Glu  Lys  Leu  Glu  Trp  Glu  Thr
```

|   |   |   |   |   |   |   |   |   |   |   |   |   |   |   |
|---|---|---|---|---|---|---|---|---|---|---|---|---|---|---|
|   |   | 850 |   |   |   | 855 |   |   |   | 860 |   |   |   |   |
| Asn<br>865 | Ile | Val | Tyr | Lys | Glu<br>870 | Ala | Lys | Glu | Ser | Val<br>875 | Asp | Ala | Leu | Phe<br>880 | Val |
| Asn | Ser | Gln | Tyr | Asp<br>885 | Arg | Leu | Gln | Ala | Thr<br>890 | Asn | Ile | Ala | Met<br>895 | Ile |
| His | Ala | Ala | Asp<br>900 | Lys | Arg | Val | His | Ser<br>905 | Ile | Arg | Glu | Ala | Tyr<br>910 | Leu | Pro |
| Glu | Leu | Ser<br>915 | Val | Ile | Pro | Gly | Val<br>920 | Asn | Ala | Ala | Ile | Phe<br>925 | Glu | Glu | Leu |
| Glu | Gly<br>930 | Arg | Ile | Phe | Thr | Ala<br>935 | Phe | Ser | Leu | Tyr | Asp<br>940 | Ala | Arg | Asn | Val |
| Ile<br>945 | Lys | Asn | Gly | Asp | Phe<br>950 | Asn | Asn | Gly | Leu | Ser<br>955 | Cys | Trp | Asn | Val<br>960 | Lys |
| Gly | His | Val | Asp | Val<br>965 | Glu | Glu | Gln | Asn | Asn<br>970 | His | Arg | Ser | Val | Leu<br>975 | Val |
| Val | Pro | Glu | Trp<br>980 | Glu | Ala | Glu | Val | Ser<br>985 | Gln | Glu | Val | Arg | Val<br>990 | Cys | Pro |
| Gly | Arg | Gly<br>995 | Tyr | Ile | Leu | Arg | Val<br>1000 | Thr | Ala | Tyr | Lys | Glu<br>1005 | Gly | Tyr | Gly |
| Glu | Gly<br>1010 | Cys | Val | Thr | Ile | His<br>1015 | Glu | Ile | Glu | Asn | Asn<br>1020 | Thr | Asp | Glu | Leu |
| Lys<br>1025 | Phe | Ser | Asn | Cys | Val<br>1030 | Glu | Glu | Glu | Val | Tyr<br>1035 | Pro | Asn | Asn | Thr<br>1040 | Val |
| Thr | Cys | Asn | Asp | Tyr<br>1045 | Thr | Ala | Thr | Gln | Glu<br>1050 | Glu | Tyr | Glu | Gly<br>1055 | Thr | Tyr |
| Thr | Ser | Arg | Asn | Arg<br>1060 | Gly | Tyr | Asp | Gly | Ala<br>1065 | Tyr | Glu | Ser | Asn<br>1070 | Ser | Ser |
| Val | Pro | Ala<br>1075 | Asp | Tyr | Ala | Ser | Ala<br>1080 | Tyr | Glu | Glu | Lys | Ala<br>1085 | Tyr | Thr | Asp |
| Gly | Arg<br>1090 | Arg | Asp | Asn | Pro | Cys<br>1095 | Glu | Ser | Asn | Arg | Gly<br>1100 | Tyr | Gly | Asp | Tyr |
| Thr<br>1105 | Pro | Leu | Pro | Ala | Gly<br>1110 | Tyr | Val | Thr | Lys | Glu<br>1115 | Leu | Glu | Tyr | Phe<br>1120 | Pro |
| Glu | Thr | Asp | Lys | Val<br>1125 | Trp | Ile | Glu | Ile | Gly<br>1130 | Glu | Thr | Glu | Gly<br>1135 | Thr | Phe |
| Ile | Val | Asp | Ser<br>1140 | Val | Glu | Leu | Leu | Leu<br>1145 | Met | Glu | Glu |   |   |   |   |

( 2 ) INFORMATION FOR SEQ ID NO:28:

( i ) SEQUENCE CHARACTERISTICS:
        ( A ) LENGTH: 3522 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

| | | | | | | |
|---|---|---|---|---|---|---|
| ATGGAAAATA | ATATTCAAAA | TCAATGCGTA | CCTTACAATT | GTTTAAATAA | TCCTGAAGTA | 60 |
| GAAATACTGA | ACGAAGAACG | CAGCACCGGC | CGCCTGCCGC | TGGACATCAG | CCTGAGCCTT | 120 |
| ACACGTTTCC | TTTTGAGTGA | ATTTGTTCCA | GGTGTGGGAG | TTGCGTTTGG | ATTATTTGAT | 180 |
| TTAATATGGG | GTTTTATAAC | TCCTTCTGAT | TGGAGCTTAT | TTCTTTTACA | GATTGAACAA | 240 |
| TTGATTGAGC | AAAGAATAGA | AACATTGGAA | AGGAACCGGG | CAATTACTAC | ATTACGAGGG | 300 |
| TTAGCAGATA | GCTATGAAAT | TTATATTGAA | GCACTAAGAG | AGTGGGAAGC | AAATCCTAAT | 360 |

-continued

| | | | | | |
|---|---|---|---|---|---|
| AATGCACAAT | TAAGGGAAGA | TGTGCGTATT | CGATTTGCTA | ATACAGACGA | CGCTTTAATA | 420 |
| ACAGCAATAA | ATAATTTTAC | ACTTACAAGT | TTTGAAATCC | CTCTTTTATC | GGTCTATGTT | 480 |
| CAAGCGGCGA | ATTTACATTT | ATCACTATTA | AGAGACGCTG | TATCGTTTGG | GCAGGGTTGG | 540 |
| GGACTGGATA | TAGCTACTGT | TAATAATCAT | TATAATAGAT | TAATAAATCT | TATTCATAGA | 600 |
| TATACGAAAC | ATTGTTTGGA | CACATACAAT | CAAGGATTAG | AAAACTTAAG | AGGTACTAAT | 660 |
| ACTCGACAAT | GGGCAAGATT | CAATCAGTTT | AGGAGAGATT | TAACACTTAC | TGTATTAGAT | 720 |
| ATCGTTGCTC | TTTTTCCGAA | CTACGATGTT | AGAACATATC | CAATTCAAAC | GTCATCCCAA | 780 |
| TTAACAAGGG | AAATTTATAC | AAGTTCAGTA | ATTGAGGATT | CTCCAGTTTC | TGCTAATATA | 840 |
| CCTAATGGTT | TTAATAGGGC | GGAATTTGGA | GTTAGACCGC | CCCATCTTAT | GGACTTTATG | 900 |
| AATTCTTTGT | TTGTAACTGC | AGAGACTGTT | AGAAGTCAAA | CTGTGTGGGG | AGGACACTTA | 960 |
| GTTAGTTCAC | GAAATACGGC | TGGTAACCGT | ATAAATTTCC | CTAGTTACGG | GGTCTTCAAT | 1020 |
| CCTGGTGGCG | CCATTTGGAT | TGCAGATGAG | GATCCACGTC | CTTTTTATCG | GACATTATCA | 1080 |
| GATCCTGTTT | TTGTCCGAGG | AGGATTTGGG | AATCCTCATT | ATGTACTGGG | GCTTAGGGGA | 1140 |
| GTAGCATTTC | AACAAACTGG | TACGAACCAC | ACCCGAACAT | TTAGAAATAG | TGGGACCATA | 1200 |
| GATTCTCTAG | ATGAAATCCC | ACCTCAGGAT | AATAGTGGGG | CACCTTGGAA | TGATTATAGT | 1260 |
| CATGTATTAA | ATCATGTTAC | ATTTGTACGA | TGGCCAGGTG | AGATTTCAGG | AAGTGATTCA | 1320 |
| TGGAGAGCTC | CAATGTTTTC | TTGGACGCAC | CGTAGTGCAA | CCCCTACAAA | TACAATTGAT | 1380 |
| CCGGAGAGGA | TTACTCAAAT | ACCATTGGTA | AAAGCACATA | CACTTCAGTC | AGGTACTACT | 1440 |
| GTTGTAAGAG | GGCCCGGGTT | TACGGGAGGA | GATATTCTTC | GACGAACAAG | TGGAGGACCA | 1500 |
| TTTGCTTATA | CTATTGTTAA | TATAAATGGG | CAATTACCCC | AAAGGTATCG | TGCAAGAATA | 1560 |
| CGCTATGCCT | CTACTACAAA | TCTAAGAATT | TACGTAACGG | TTGCAGGTGA | ACGGATTTTT | 1620 |
| GCTGGTCAAT | TTAACAAAAC | AATGGATACC | GGTGACCCAT | TAACATTCCA | ATCTTTTAGT | 1680 |
| TACGCAACTA | TTAATACAGC | TTTTACATTC | CCAATGAGCC | AGAGTAGTTT | CACAGTAGGT | 1740 |
| GCTGATACTT | TTAGTTCAGG | GAATGAAGTT | TATATAGACA | GATTTGAATT | GATTCCAGTT | 1800 |
| ACTGCAACAT | TTGAAGCAGA | ATATGATTTA | GAAAGAGCAC | AAAAGGCGGT | GAATGCGCTG | 1860 |
| TTTACTTCTA | TAAACCAAAT | AGGGATAAAA | ACAGATGTGA | CGGATTATCA | TATCGATCGA | 1920 |
| GTGTCCAATT | TAGTTACGTA | TTTATCGGAT | GAATTTTGTC | TGGATGAAAA | GCGAGAATTG | 1980 |
| TCCGAGAAAG | TCAAACATGC | GAAGCGACTC | AGTGATGAAC | GCAATTTACT | CCAAGATTCA | 2040 |
| AATTTCAAAG | ACATTAATAG | GCAACCAGAA | CGTGGGTGGG | GCGGAAGTAC | AGGGATTACC | 2100 |
| ATCCAAGGAG | GGGATGACGT | ATTTAAAGAA | AATTACGTCA | CACTATCAGG | TACCTTTGAT | 2160 |
| GAGTGCTATC | CAACATATTT | GTATCAAAAA | ATCGATGAAT | CAAAATTAAA | AGCCTTTACC | 2220 |
| CGTTATCAAT | TAAGAGGGTA | TATCGAAGAT | AGTCAAGACT | TAGAAATCTA | TTTAATTCGC | 2280 |
| TACAATGCAA | AACATGAAAC | AGTAAATGTG | CCAGGTACGG | GTTCCTTATG | GCCGCTTTCA | 2340 |
| GCCCAAAGTC | CAATCGGAAA | GTGTGGAGAG | CCGAATCGAT | GCGCGCCACA | CCTTGAATGG | 2400 |
| AATCCTGACT | TAGATTGTTC | GTGTAGGGAT | GGAGAAAAGT | GTGCCCATCA | TTCGCATCAT | 2460 |
| TTCTCCTTAG | ACATTGATGT | AGGATGTACA | GACTTAAATG | AGGACCTAGG | TGTATGGGTG | 2520 |
| ATCTTTAAGA | TTAAGACGCA | AGATGGGCAC | GCAAGACTAG | GAATCTAGA | GTTTCTCGAA | 2580 |
| GAGAAACCAT | TAGTAGGAGA | AGCGCTAGCT | CGTGTGAAAA | GAGCGGAGAA | AAAATGGAGA | 2640 |
| GACAAACGTG | AAAAATTGGA | ATGGGAAACA | AATATCGTTT | ATAAAGAGGC | AAAAGAATCT | 2700 |
| GTAGATGCTT | TATTTGTAAA | CTCTCAATAT | GATCAATTAC | AAGCGGATAC | GAATATTGCC | 2760 |

```
ATGATTCATG CGGCAGATAA ACGTGTTCAT AGCATTCGAG AAGCTTATCT GCCTGAGCTG    2820
TCTGTGATTC CGGGTGTCAA TGCGGCTATT TTTGAAGAAT TAGAAGGGCG TATTTTCACT    2880
GCATTCTCCC TATATGATGC GAGAAATGTC ATTAAAAATG GTGATTTTAA TAATGGCTTA    2940
TCCTGCTGGA ACGTGAAAGG GCATGTAGAT GTAGAAGAAC AAAACAACCA CCGTTCGGTC    3000
CTTGTTGTTC CGGAATGGGA AGCAGAAGTG TCACAAGAAG TTCGTGTCTG TCCGGGTCGT    3060
GGCTATATCC TTCGTGTCAC AGCGTACAAG GAGGGATATG GAGAAGGTTG CGTAACCATT    3120
CATGAGATCG AGAACAATAC AGACGAACTG AAGTTTAGCA ACTGTGTAGA AGAGGAAGTA    3180
TATCCAAACA ACACGGTAAC GTGTAATGAT TATACTGCGA CTCAAGAAGA ATATGAGGGT    3240
ACGTACACTT CTCGTAATCG AGGATATGAC GGAGCCTATG AAAGCAATTC TTCTGTACCA    3300
GCTGATTATG CATCAGCCTA TGAAGAAAAA GCATATACAG ATGGACGAAG AGACAATCCT    3360
TGTGAATCTA ACAGAGGATA TGGGGATTAC ACACCACTAC CAGCTGGCTA TGTGACAAAA    3420
GAATTAGAGT ACTTCCCAGA AACCGATAAG GTATGGATTG AGATCGGAGA AACGGAAGGA    3480
ACATTCATCG TGGACAGCGT GGAATTACTT CTTATGGAGG AA                       3522
```

( 2 ) INFORMATION FOR SEQ ID NO:29:

( i ) SEQUENCE CHARACTERISTICS:
    ( A ) LENGTH: 1174 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:29:

```
Met Glu Asn Asn Ile Gln Asn Gln Cys Val Pro Tyr Asn Cys Leu Asn
 1               5                  10                  15
Asn Pro Glu Val Glu Ile Leu Asn Glu Glu Arg Ser Thr Gly Arg Leu
                20                  25                  30
Pro Leu Asp Ile Ser Leu Ser Leu Thr Arg Phe Leu Leu Ser Glu Phe
            35                  40                  45
Val Pro Gly Val Gly Val Ala Phe Gly Leu Phe Asp Leu Ile Trp Gly
    50                  55                  60
Phe Ile Thr Pro Ser Asp Trp Ser Leu Phe Leu Leu Gln Ile Glu Gln
 65                 70                  75                  80
Leu Ile Glu Gln Arg Ile Glu Thr Leu Glu Arg Asn Arg Ala Ile Thr
                85                  90                  95
Thr Leu Arg Gly Leu Ala Asp Ser Tyr Glu Ile Tyr Ile Glu Ala Leu
               100                 105                 110
Arg Glu Trp Glu Ala Asn Pro Asn Asn Ala Gln Leu Arg Glu Asp Val
           115                 120                 125
Arg Ile Arg Phe Ala Asn Thr Asp Asp Ala Leu Ile Thr Ala Ile Asn
       130                 135                 140
Asn Phe Thr Leu Thr Ser Phe Glu Ile Pro Leu Leu Ser Val Tyr Val
145                 150                 155                 160
Gln Ala Ala Asn Leu His Leu Ser Leu Leu Arg Asp Ala Val Ser Phe
               165                 170                 175
Gly Gln Gly Trp Gly Leu Asp Ile Ala Thr Val Asn Asn His Tyr Asn
           180                 185                 190
Arg Leu Ile Asn Leu Ile His Arg Tyr Thr Lys His Cys Leu Asp Thr
       195                 200                 205
Tyr Asn Gln Gly Leu Glu Asn Leu Arg Gly Thr Asn Thr Arg Gln Trp
```

|     |     |     |     |     |     |     |     |     |     |     |     |     |     |     |     |
|---|---|---|---|---|---|---|---|---|---|---|---|---|---|---|---|
|     |     |     |     | 210 |     |     |     |     | 215 |     |     |     |     | 220 |     |
| Ala | Arg | Phe | Asn | Gln | Phe | Arg | Arg | Asp | Leu | Thr | Leu | Thr | Val | Leu | Asp |
| 225 |     |     |     | 230 |     |     |     |     | 235 |     |     |     |     |     | 240 |
| Ile | Val | Ala | Leu | Phe | Pro | Asn | Tyr | Asp | Val | Arg | Thr | Tyr | Pro | Ile | Gln |
|     |     |     |     | 245 |     |     |     |     | 250 |     |     |     |     | 255 |     |
| Thr | Ser | Ser | Gln | Leu | Thr | Arg | Glu | Ile | Tyr | Thr | Ser | Ser | Val | Ile | Glu |
|     |     |     | 260 |     |     |     |     | 265 |     |     |     |     | 270 |     |     |
| Asp | Ser | Pro | Val | Ser | Ala | Asn | Ile | Pro | Asn | Gly | Phe | Asn | Arg | Ala | Glu |
|     |     | 275 |     |     |     |     | 280 |     |     |     |     | 285 |     |     |     |
| Phe | Gly | Val | Arg | Pro | Pro | His | Leu | Met | Asp | Phe | Met | Asn | Ser | Leu | Phe |
|     | 290 |     |     |     |     | 295 |     |     |     |     | 300 |     |     |     |     |
| Val | Thr | Ala | Glu | Thr | Val | Arg | Ser | Gln | Thr | Val | Trp | Gly | Gly | His | Leu |
| 305 |     |     |     | 310 |     |     |     |     | 315 |     |     |     |     |     | 320 |
| Val | Ser | Ser | Arg | Asn | Thr | Ala | Gly | Asn | Arg | Ile | Asn | Phe | Pro | Ser | Tyr |
|     |     |     |     | 325 |     |     |     |     | 330 |     |     |     |     | 335 |     |
| Gly | Val | Phe | Asn | Pro | Gly | Gly | Ala | Ile | Trp | Ile | Ala | Asp | Glu | Asp | Pro |
|     |     |     | 340 |     |     |     |     | 345 |     |     |     |     | 350 |     |     |
| Arg | Pro | Phe | Tyr | Arg | Thr | Leu | Ser | Asp | Pro | Val | Phe | Val | Arg | Gly | Gly |
|     |     | 355 |     |     |     |     | 360 |     |     |     |     | 365 |     |     |     |
| Phe | Gly | Asn | Pro | His | Tyr | Val | Leu | Gly | Leu | Arg | Gly | Val | Ala | Phe | Gln |
|     | 370 |     |     |     |     | 375 |     |     |     |     | 380 |     |     |     |     |
| Gln | Thr | Gly | Thr | Asn | His | Thr | Arg | Thr | Phe | Arg | Asn | Ser | Gly | Thr | Ile |
| 385 |     |     |     |     | 390 |     |     |     |     | 395 |     |     |     |     | 400 |
| Asp | Ser | Leu | Asp | Glu | Ile | Pro | Pro | Gln | Asp | Asn | Ser | Gly | Ala | Pro | Trp |
|     |     |     |     | 405 |     |     |     |     | 410 |     |     |     |     | 415 |     |
| Asn | Asp | Tyr | Ser | His | Val | Leu | Asn | His | Val | Thr | Phe | Val | Arg | Trp | Pro |
|     |     |     | 420 |     |     |     |     | 425 |     |     |     |     | 430 |     |     |
| Gly | Glu | Ile | Ser | Gly | Ser | Asp | Ser | Trp | Arg | Ala | Pro | Met | Phe | Ser | Trp |
|     |     |     | 435 |     |     |     | 440 |     |     |     |     | 445 |     |     |     |
| Thr | His | Arg | Ser | Ala | Thr | Pro | Thr | Asn | Thr | Ile | Asp | Pro | Glu | Arg | Ile |
|     | 450 |     |     |     |     | 455 |     |     |     |     | 460 |     |     |     |     |
| Thr | Gln | Ile | Pro | Leu | Val | Lys | Ala | His | Thr | Leu | Gln | Ser | Gly | Thr | Thr |
| 465 |     |     |     |     | 470 |     |     |     |     | 475 |     |     |     |     | 480 |
| Val | Val | Arg | Gly | Pro | Gly | Phe | Thr | Gly | Gly | Asp | Ile | Leu | Arg | Arg | Thr |
|     |     |     |     | 485 |     |     |     |     | 490 |     |     |     |     | 495 |     |
| Ser | Gly | Gly | Pro | Phe | Ala | Tyr | Thr | Ile | Val | Asn | Ile | Asn | Gly | Gln | Leu |
|     |     |     | 500 |     |     |     |     | 505 |     |     |     |     | 510 |     |     |
| Pro | Gln | Arg | Tyr | Arg | Ala | Arg | Ile | Arg | Tyr | Ala | Ser | Thr | Thr | Asn | Leu |
|     |     | 515 |     |     |     |     | 520 |     |     |     |     | 525 |     |     |     |
| Arg | Ile | Tyr | Val | Thr | Val | Ala | Gly | Glu | Arg | Ile | Phe | Ala | Gly | Gln | Phe |
|     |     | 530 |     |     |     |     | 535 |     |     |     |     | 540 |     |     |     |
| Asn | Lys | Thr | Met | Asp | Thr | Gly | Asp | Pro | Leu | Thr | Phe | Gln | Ser | Phe | Ser |
| 545 |     |     |     |     | 550 |     |     |     |     | 555 |     |     |     |     | 560 |
| Tyr | Ala | Thr | Ile | Asn | Thr | Ala | Phe | Thr | Phe | Pro | Met | Ser | Gln | Ser | Ser |
|     |     |     |     | 565 |     |     |     |     | 570 |     |     |     |     | 575 |     |
| Phe | Thr | Val | Gly | Ala | Asp | Thr | Phe | Ser | Ser | Gly | Asn | Glu | Val | Tyr | Ile |
|     |     |     | 580 |     |     |     |     | 585 |     |     |     |     | 590 |     |     |
| Asp | Arg | Phe | Glu | Leu | Ile | Pro | Val | Thr | Ala | Thr | Phe | Glu | Ala | Glu | Tyr |
|     |     | 595 |     |     |     |     | 600 |     |     |     |     | 605 |     |     |     |
| Asp | Leu | Glu | Arg | Ala | Gln | Lys | Ala | Val | Asn | Ala | Leu | Phe | Thr | Ser | Ile |
|     |     | 610 |     |     |     |     | 615 |     |     |     |     | 620 |     |     |     |
| Asn | Gln | Ile | Gly | Ile | Lys | Thr | Asp | Val | Thr | Asp | Tyr | His | Ile | Asp | Arg |
| 625 |     |     |     |     | 630 |     |     |     |     | 635 |     |     |     |     | 640 |

| | | | | | | | | | | | | | | |
|---|---|---|---|---|---|---|---|---|---|---|---|---|---|---|
| Val | Ser | Asn | Leu | Val 645 | Thr | Tyr | Leu | Ser 650 | Asp | Glu | Phe | Cys | Leu 655 | Asp | Glu |
| Lys | Arg | Glu | Leu 660 | Ser | Glu | Lys | Val | Lys 665 | His | Ala | Lys | Arg | Leu 670 | Ser | Asp |
| Glu | Arg | Asn 675 | Leu | Leu | Gln | Asp | Ser 680 | Asn | Phe | Lys | Asp | Ile 685 | Asn | Arg | Gln |
| Pro | Glu 690 | Arg | Gly | Trp | Gly 695 | Gly | Ser | Thr | Gly | Ile 700 | Thr | Ile | Gln | Gly | Gly |
| Asp 705 | Asp | Val | Phe | Lys | Glu 710 | Asn | Tyr | Val | Thr | Leu 715 | Ser | Gly | Thr | Phe | Asp 720 |
| Glu | Cys | Tyr | Pro | Thr 725 | Tyr | Leu | Tyr | Gln | Lys 730 | Ile | Asp | Glu | Ser | Lys 735 | Leu |
| Lys | Ala | Phe | Thr 740 | Arg | Tyr | Gln | Leu | Arg 745 | Gly | Tyr | Ile | Glu | Asp 750 | Ser | Gln |
| Asp | Leu | Glu 755 | Ile | Tyr | Leu | Ile | Arg 760 | Tyr | Asn | Ala | Lys | His 765 | Glu | Thr | Val |
| Asn | Val 770 | Pro | Gly | Thr | Gly 775 | Ser | Leu | Trp | Pro | Leu 780 | Ser | Ala | Gln | Ser | Pro |
| Ile 785 | Gly | Lys | Cys | Gly | Glu 790 | Pro | Asn | Arg | Cys | Ala 795 | Pro | His | Leu | Glu | Trp 800 |
| Asn | Pro | Asp | Leu | Asp 805 | Cys | Ser | Cys | Arg | Asp 810 | Gly | Glu | Lys | Cys | Ala 815 | His |
| His | Ser | His | His 820 | Phe | Ser | Leu | Asp | Ile 825 | Asp | Val | Gly | Cys | Thr 830 | Asp | Leu |
| Asn | Glu | Asp 835 | Leu | Gly | Val | Trp | Val 840 | Ile | Phe | Lys | Ile | Lys 845 | Thr | Gln | Asp |
| Gly | His 850 | Ala | Arg | Leu | Gly | Asn 855 | Leu | Glu | Phe | Leu | Glu 860 | Glu | Lys | Pro | Leu |
| Val 865 | Gly | Glu | Ala | Leu | Ala 870 | Arg | Val | Lys | Arg | Ala 875 | Glu | Lys | Lys | Trp | Arg 880 |
| Asp | Lys | Arg | Glu | Lys 885 | Leu | Glu | Trp | Glu | Thr 890 | Asn | Ile | Val | Tyr | Lys 895 | Glu |
| Ala | Lys | Glu | Ser 900 | Val | Asp | Ala | Leu | Phe 905 | Val | Asn | Ser | Gln | Tyr 910 | Asp | Gln |
| Leu | Gln | Ala 915 | Asp | Thr | Asn | Ile | Ala 920 | Met | Ile | His | Ala | Ala 925 | Asp | Lys | Arg |
| Val | His 930 | Ser | Ile | Arg | Glu | Ala 935 | Tyr | Leu | Pro | Glu | Leu 940 | Ser | Val | Ile | Pro |
| Gly 945 | Val | Asn | Ala | Ala | Ile 950 | Phe | Glu | Glu | Leu | Glu 955 | Gly | Arg | Ile | Phe | Thr 960 |
| Ala | Phe | Ser | Leu | Tyr 965 | Asp | Ala | Arg | Asn | Val 970 | Ile | Lys | Asn | Gly | Asp 975 | Phe |
| Asn | Asn | Gly | Leu 980 | Ser | Cys | Trp | Asn | Val 985 | Lys | Gly | His | Val | Asp 990 | Val | Glu |
| Glu | Gln | Asn 995 | Asn | His | Arg | Ser | Val 1000 | Leu | Val | Val | Pro | Glu 1005 | Trp | Glu | Ala |
| Glu | Val 1010 | Ser | Gln | Glu | Val | Arg 1015 | Val | Cys | Pro | Gly | Arg 1020 | Gly | Tyr | Ile | Leu |
| Arg 1025 | Val | Thr | Ala | Tyr | Lys 1030 | Glu | Gly | Tyr | Gly | Glu 1035 | Gly | Cys | Val | Thr | Ile 1040 |
| His | Glu | Ile | Glu | Asn 1045 | Asn | Thr | Asp | Glu | Leu 1050 | Lys | Phe | Ser | Asn | Cys 1055 | Val |
| Glu | Glu | Glu | Val 1060 | Tyr | Pro | Asn | Asn | Thr 1065 | Val | Thr | Cys | Asn | Asp 1070 | Tyr | Thr |

```
    Ala  Thr  Gln  Glu  Glu  Tyr  Glu  Gly  Thr  Tyr  Thr  Ser  Arg  Asn  Arg  Gly
              1075                    1080                    1085

Tyr  Asp  Gly  Ala  Tyr  Glu  Ser  Asn  Ser  Ser  Val  Pro  Ala  Asp  Tyr  Ala
         1090                    1095                    1100

Ser  Ala  Tyr  Glu  Glu  Lys  Ala  Tyr  Thr  Asp  Gly  Arg  Arg  Asp  Asn  Pro
    1105                    1110                    1115                         1120

Cys  Glu  Ser  Asn  Arg  Gly  Tyr  Gly  Asp  Tyr  Thr  Pro  Leu  Pro  Ala  Gly
                        1125                    1130                    1135

Tyr  Val  Thr  Lys  Glu  Leu  Glu  Tyr  Phe  Pro  Glu  Thr  Asp  Lys  Val  Trp
                   1140                    1145                    1150

Ile  Glu  Ile  Gly  Glu  Thr  Glu  Gly  Thr  Phe  Ile  Val  Asp  Ser  Val  Glu
              1155                    1160                    1165

Leu  Leu  Leu  Met  Glu  Glu
         1170
```

( 2 ) INFORMATION FOR SEQ ID NO:30:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:30:

```
    Xaa  Xaa  Ile  Asp  Xaa  Xaa  Glu  Xaa  Xaa  Xaa  Xaa  Xaa
                        5                        10
```

( 2 ) INFORMATION FOR SEQ ID NO:31:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:31:

```
    Tyr  Pro  Asn  Asn  Thr  Val  Thr  Cys
                        5
```

( 2 ) INFORMATION FOR SEQ ID NO:32:

( i ) SEQUENCE CHARACTERISTICS:
        ( A ) LENGTH: 1184 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:32:

```
    Cys  Arg  Tyr  Ile  Phe  Ala  Met  Pro  Glu  Pro  Met  Glu  Asn  Asn  Ile  Gln
    1                   5                   10                          15

Asn  Gln  Cys  Val  Pro  Tyr  Asn  Cys  Leu  Asn  Asn  Pro  Glu  Val  Glu  Ile
                   20                  25                      30

Leu  Asn  Glu  Glu  Arg  Ser  Thr  Gly  Arg  Leu  Pro  Leu  Asp  Ile  Ser  Leu
              35                      40                      45

Ser  Leu  Thr  Arg  Phe  Leu  Leu  Ser  Glu  Phe  Val  Pro  Gly  Val  Gly  Val
         50                      55                      60

Ala  Phe  Gly  Leu  Phe  Asp  Leu  Ile  Trp  Gly  Phe  Ile  Thr  Pro  Ser  Asp
```

|  |  |  |  | 65 |  |  |  | 70 |  |  |  | 75 |  |  |  | 80 |
|---|---|---|---|---|---|---|---|---|---|---|---|---|---|---|---|---|
| Trp | Ser | Leu | Phe | Leu | Leu | Gln | Ile | Glu | Gln | Leu | Ile | Glu | Gln | Arg | Ile |
|  |  |  |  |  | 85 |  |  |  | 90 |  |  |  | 95 |  |  |
| Glu | Thr | Leu | Glu | Arg | Asn | Arg | Ala | Ile | Thr | Thr | Leu | Arg | Gly | Leu | Ala |
|  |  |  | 100 |  |  |  |  | 105 |  |  |  | 110 |  |  |  |
| Asp | Ser | Tyr | Glu | Ile | Tyr | Ile | Glu | Ala | Leu | Arg | Glu | Trp | Glu | Ala | Asn |
|  |  |  | 115 |  |  |  |  | 120 |  |  |  | 125 |  |  |  |
| Pro | Asn | Asn | Ala | Gln | Leu | Arg | Glu | Asp | Val | Arg | Ile | Arg | Phe | Ala | Asn |
|  | 130 |  |  |  |  | 135 |  |  |  |  | 140 |  |  |  |  |
| Thr | Asp | Asp | Ala | Leu | Ile | Thr | Ala | Ile | Asn | Asn | Phe | Thr | Leu | Thr | Ser |
| 145 |  |  |  |  | 150 |  |  |  |  | 155 |  |  |  |  | 160 |
| Phe | Glu | Ile | Pro | Leu | Leu | Ser | Val | Tyr | Val | Gln | Ala | Ala | Asn | Leu | His |
|  |  |  |  |  | 165 |  |  |  | 170 |  |  |  | 175 |  |  |
| Leu | Ser | Leu | Leu | Arg | Asp | Ala | Val | Ser | Phe | Gly | Gln | Gly | Trp | Gly | Leu |
|  |  |  | 180 |  |  |  |  | 185 |  |  |  | 190 |  |  |  |
| Asp | Ile | Ala | Thr | Val | Asn | Asn | His | Tyr | Asn | Arg | Leu | Ile | Asn | Leu | Ile |
|  |  |  | 195 |  |  |  |  | 200 |  |  |  | 205 |  |  |  |
| His | Arg | Tyr | Thr | Lys | His | Cys | Leu | Asp | Thr | Tyr | Asn | Gln | Gly | Leu | Glu |
|  | 210 |  |  |  |  | 215 |  |  |  |  | 220 |  |  |  |  |
| Asn | Leu | Arg | Gly | Thr | Asn | Thr | Arg | Gln | Trp | Ala | Arg | Phe | Asn | Gln | Phe |
| 225 |  |  |  |  | 230 |  |  |  |  | 235 |  |  |  |  | 240 |
| Arg | Arg | Asp | Leu | Thr | Leu | Thr | Val | Leu | Asp | Ile | Val | Ala | Leu | Phe | Pro |
|  |  |  |  | 245 |  |  |  |  | 250 |  |  |  |  | 255 |  |
| Asn | Tyr | Asp | Val | Arg | Thr | Tyr | Pro | Ile | Gln | Thr | Ser | Ser | Gln | Leu | Thr |
|  |  |  | 260 |  |  |  |  | 265 |  |  |  | 270 |  |  |  |
| Arg | Glu | Ile | Tyr | Thr | Ser | Ser | Val | Ile | Glu | Asp | Ser | Pro | Val | Ser | Ala |
|  |  | 275 |  |  |  |  | 280 |  |  |  |  | 285 |  |  |  |
| Asn | Ile | Pro | Asn | Gly | Phe | Asn | Arg | Ala | Glu | Phe | Gly | Val | Arg | Pro | Pro |
|  | 290 |  |  |  |  | 295 |  |  |  |  | 300 |  |  |  |  |
| His | Leu | Met | Asp | Phe | Met | Asn | Ser | Leu | Phe | Val | Thr | Ala | Glu | Thr | Val |
| 305 |  |  |  |  | 310 |  |  |  |  | 315 |  |  |  |  | 320 |
| Arg | Ser | Gln | Thr | Val | Trp | Gly | Gly | His | Leu | Val | Ser | Ser | Arg | Asn | Thr |
|  |  |  |  | 325 |  |  |  |  | 330 |  |  |  |  | 335 |  |
| Ala | Gly | Asn | Arg | Ile | Asn | Phe | Pro | Ser | Tyr | Gly | Val | Phe | Asn | Pro | Gly |
|  |  |  | 340 |  |  |  |  | 345 |  |  |  | 350 |  |  |  |
| Gly | Ala | Ile | Trp | Ile | Ala | Asp | Glu | Asp | Pro | Arg | Pro | Phe | Tyr | Arg | Thr |
|  |  |  | 355 |  |  |  |  | 360 |  |  |  | 365 |  |  |  |
| Leu | Ser | Asp | Pro | Val | Phe | Val | Arg | Gly | Gly | Phe | Gly | Asn | Pro | His | Tyr |
|  | 370 |  |  |  |  | 375 |  |  |  |  | 380 |  |  |  |  |
| Val | Leu | Gly | Leu | Arg | Gly | Val | Ala | Phe | Gln | Gln | Thr | Gly | Thr | Asn | His |
| 385 |  |  |  |  | 390 |  |  |  |  | 395 |  |  |  |  | 400 |
| Thr | Arg | Thr | Phe | Arg | Asn | Ser | Gly | Thr | Ile | Asp | Ser | Leu | Asp | Glu | Ile |
|  |  |  |  | 405 |  |  |  |  | 410 |  |  |  |  | 415 |  |
| Pro | Pro | Gln | Asp | Asn | Ser | Gly | Ala | Pro | Trp | Asn | Asp | Tyr | Ser | His | Val |
|  |  |  | 420 |  |  |  |  | 425 |  |  |  | 430 |  |  |  |
| Leu | Asn | His | Val | Thr | Phe | Val | Arg | Trp | Pro | Gly | Glu | Ile | Ser | Gly | Ser |
|  |  | 435 |  |  |  |  | 440 |  |  |  |  | 445 |  |  |  |
| Asp | Ser | Trp | Arg | Ala | Pro | Met | Phe | Ser | Trp | Thr | His | Arg | Ser | Ala | Thr |
|  | 450 |  |  |  |  | 455 |  |  |  |  | 460 |  |  |  |  |
| Pro | Thr | Asn | Thr | Ile | Asp | Pro | Glu | Arg | Ile | Thr | Gln | Ile | Pro | Leu | Val |
| 465 |  |  |  |  | 470 |  |  |  |  | 475 |  |  |  |  | 480 |
| Lys | Ala | His | Thr | Leu | Gln | Ser | Gly | Thr | Thr | Val | Val | Arg | Gly | Pro | Gly |
|  |  |  |  | 485 |  |  |  |  | 490 |  |  |  |  | 495 |  |

```
Phe Thr Gly Gly Asp Ile Leu Arg Arg Thr Ser Gly Gly Pro Phe Ala
            500             505             510
Tyr Thr Ile Val Asn Ile Asn Gly Gln Leu Pro Gln Arg Tyr Arg Ala
        515             520             525
Arg Ile Arg Tyr Ala Ser Thr Thr Asn Leu Arg Ile Tyr Val Thr Val
    530             535             540
Ala Gly Glu Arg Ile Phe Ala Gly Gln Phe Asn Lys Thr Met Asp Thr
545             550             555                     560
Gly Asp Pro Leu Thr Phe Gln Ser Phe Ser Tyr Ala Thr Ile Asn Thr
                565             570             575
Ala Phe Thr Phe Pro Met Ser Gln Ser Ser Phe Thr Val Gly Ala Asp
            580             585             590
Thr Phe Ser Ser Gly Asn Glu Val Tyr Ile Asp Arg Phe Glu Leu Ile
        595             600             605
Pro Val Thr Ala Thr Phe Glu Ala Glu Tyr Asp Leu Glu Arg Ala Gln
    610             615             620
Lys Ala Val Asn Ala Leu Phe Thr Ser Ile Asn Gln Ile Gly Ile Lys
625             630             635                     640
Thr Asp Val Thr Asp Tyr His Ile Asp Gln Val Ser Asn Leu Val Asp
                645             650             655
Cys Leu Ser Asp Glu Phe Cys Leu Asp Glu Lys Arg Glu Leu Ser Glu
            660             665             670
Lys Val Lys His Ala Lys Arg Leu Ser Asp Glu Arg Asn Leu Leu Gln
        675             680             685
Asp Pro Asn Phe Lys Gly Ile Asn Arg Gln Leu Asp Arg Gly Trp Arg
    690             695             700
Gly Ser Thr Asp Ile Thr Ile Gln Arg Gly Asp Asp Val Phe Lys Glu
705             710             715                     720
Asn Tyr Val Thr Leu Pro Gly Thr Phe Asp Glu Cys Tyr Pro Thr Tyr
                725             730             735
Leu Tyr Gln Lys Ile Asp Glu Ser Lys Leu Lys Pro Tyr Thr Arg Tyr
            740             745             750
Gln Leu Arg Gly Tyr Ile Glu Asp Ser Gln Asp Leu Glu Ile Tyr Leu
        755             760             765
Ile Arg Tyr Asn Ala Lys His Glu Thr Val Asn Val Leu Gly Thr Gly
    770             775             780
Ser Leu Trp Pro Leu Ser Val Gln Ser Pro Ile Arg Lys Cys Gly Glu
785             790             795                     800
Pro Asn Arg Cys Ala Pro His Leu Glu Trp Asn Pro Asp Leu Asp Cys
                805             810             815
Ser Cys Arg Asp Gly Glu Lys Cys Ala His His Ser His His Phe Ser
            820             825             830
Leu Asp Ile Asp Val Gly Cys Thr Asp Leu Asn Glu Asp Leu Asp Val
        835             840             845
Trp Val Ile Phe Lys Ile Lys Thr Gln Asp Gly His Ala Arg Leu Gly
    850             855             860
Asn Leu Glu Phe Leu Glu Glu Lys Pro Leu Val Gly Glu Ala Leu Ala
865             870             875                     880
Arg Val Lys Arg Ala Glu Lys Lys Trp Arg Asp Lys Arg Glu Lys Leu
                885             890             895
Glu Leu Glu Thr Asn Ile Val Tyr Lys Glu Ala Lys Glu Ser Val Asp
            900             905             910
Ala Leu Phe Val Asn Ser Gln Tyr Asp Gln Leu Gln Ala Asp Thr Asn
        915             920             925
```

```
Ile Ala Met Ile His Ala Ala Asp Lys Arg Val His Arg Ile Arg Glu
    930              935             940

Ala Tyr Leu Pro Glu Leu Ser Val Ile Pro Gly Val Asn Val Asp Ile
945              950             955                         960

Phe Glu Glu Leu Lys Gly Arg Ile Phe Thr Ala Phe Phe Leu Tyr Asp
                965             970                     975

Ala Arg Asn Val Ile Lys Asn Gly Asp Phe Asn Asn Gly Leu Ser Cys
            980             985                 990

Trp Asn Val Lys Gly His Val Asp Val Glu Glu Gln Asn Asn His Arg
            995             1000            1005

Ser Val Leu Val Val Pro Glu Trp Glu Ala Glu Val Ser Gln Glu Val
    1010            1015            1020

Arg Val Cys Pro Gly Arg Gly Tyr Ile Leu Arg Val Thr Ala Tyr Lys
1025            1030            1035                    1040

Glu Gly Tyr Gly Glu Gly Cys Val Thr Ile His Glu Ile Glu Asn Asn
            1045            1050            1055

Thr Asp Glu Leu Lys Phe Ser Asn Cys Val Glu Glu Val Tyr Pro
            1060            1065            1070

Asn Asn Thr Val Thr Cys Asn Asp Tyr Thr Ala Asn Gln Glu Glu Tyr
        1075            1080            1085

Gly Gly Ala Tyr Thr Ser Arg Asn Arg Gly Tyr Asp Glu Thr Tyr Gly
    1090            1095            1100

Ser Asn Ser Ser Val Pro Ala Asp Tyr Ala Ser Val Tyr Glu Glu Lys
1105            1110            1115                    1120

Ser Tyr Thr Asp Gly Arg Arg Asp Asn Pro Cys Glu Ser Asn Arg Gly
            1125            1130            1135

Tyr Gly Asp Tyr Thr Pro Leu Pro Ala Gly Tyr Val Thr Lys Glu Leu
            1140            1145            1150

Glu Tyr Phe Pro Glu Thr Asp Lys Val Trp Ile Glu Ile Gly Glu Thr
        1155            1160            1165

Glu Gly Thr Phe Ile Val Asp Ser Val Glu Leu Leu Leu Met Glu Glu
    1170            1175            1180
```

( 2 ) INFORMATION FOR SEQ ID NO:33:

( i ) SEQUENCE CHARACTERISTICS:
        ( A ) LENGTH: 1165 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:33:

```
Cys Arg Tyr Ile Ala Asx Met Pro Glu Pro Met Asp Asn Asn Pro Asn
1               5               10                      15

Ile Asn Glu Cys Ile Pro Tyr Asn Cys Leu Ser Asn Pro Glu Val Glu
            20              25              30

Val Leu Gly Gly Glu Arg Ile Glu Thr Gly Tyr Thr Pro Ile Asp Ile
        35              40              45

Ser Leu Ser Leu Thr Gln Phe Leu Leu Ser Glu Phe Val Pro Gly Ala
    50              55              60

Gly Phe Val Leu Gly Leu Val Asp Ile Ile Trp Gly Ile Phe Gly Pro
65              70              75                      80

Ser Gln Trp Asp Ala Phe Leu Val Gln Ile Glu Gln Leu Ile Asn Gln
            85              90              95
```

```
Arg Ile Glu Glu Phe Ala Arg Asn Gln Ala Ile Ser Arg Leu Glu Gly
            100                 105                 110

Leu Ser Asn Leu Tyr Gln Ile Tyr Ala Glu Ser Phe Arg Glu Trp Glu
        115                 120                 125

Ala Asp Pro Thr Asn Pro Ala Leu Arg Glu Glu Met Arg Ile Gln Phe
130                 135                 140

Asn Asp Met Asn Ser Ala Leu Thr Thr Ala Ile Pro Leu Phe Ala Val
145                 150                 155                 160

Gln Asn Tyr Gln Val Pro Leu Leu Ser Val Tyr Val Gln Ala Ala Asn
                165                 170                 175

Leu His Leu Ser Val Leu Arg Asp Val Ser Val Phe Gly Gln Arg Trp
            180                 185                 190

Gly Phe Asp Ala Ala Thr Ile Asn Ser Arg Tyr Asn Asp Leu Thr Arg
        195                 200                 205

Leu Ile Gly Asn Tyr Thr Asp His Ala Val Arg Trp Tyr Asn Thr Gly
    210                 215                 220

Leu Glu Arg Val Trp Gly Pro Asp Ser Arg Asp Trp Ile Arg Tyr Asn
225                 230                 235                 240

Gln Phe Arg Arg Glu Leu Thr Leu Thr Val Leu Asp Ile Val Ser Leu
                245                 250                 255

Phe Pro Asn Tyr Asp Ser Arg Thr Tyr Pro Ile Arg Thr Val Ser Gln
            260                 265                 270

Leu Thr Arg Glu Ile Tyr Thr Asn Pro Val Leu Glu Asn Phe Asp Gly
        275                 280                 285

Ser Phe Arg Gly Ser Ala Gln Gly Ile Glu Gly Ser Ile Arg Ser Pro
    290                 295                 300

His Leu Met Asp Ile Leu Asn Ser Ile Thr Ile Tyr Thr Asp Ala His
305                 310                 315                 320

Arg Gly Glu Tyr Tyr Trp Ser Gly His Gln Ile Met Ala Ser Pro Val
                325                 330                 335

Gly Phe Ser Gly Pro Glu Phe Thr Phe Pro Leu Tyr Gly Thr Met Gly
            340                 345                 350

Asn Ala Ala Pro Gln Gln Arg Ile Val Ala Gln Leu Gly Gln Gly Val
        355                 360                 365

Tyr Arg Thr Leu Ser Ser Thr Leu Tyr Arg Arg Pro Phe Asn Ile Gly
    370                 375                 380

Ile Asn Asn Gln Gln Leu Ser Val Leu Asp Gly Thr Glu Phe Ala Tyr
385                 390                 395                 400

Gly Thr Ser Ser Asn Leu Pro Ser Ala Val Tyr Arg Lys Ser Gly Thr
                405                 410                 415

Val Asp Ser Leu Asp Glu Ile Pro Pro Gln Asn Asn Asn Val Pro Pro
            420                 425                 430

Arg Gln Gly Phe Ser His Arg Leu Ser His Val Ser Met Phe Arg Ser
        435                 440                 445

Gly Phe Ser Asn Ser Ser Val Ser Ile Ile Arg Ala Pro Met Phe Ser
    450                 455                 460

Trp Ile His Arg Ser Ala Glu Phe Asn Asn Ile Ile Pro Ser Ser Gln
465                 470                 475                 480

Ile Thr Gln Ile Pro Leu Thr Lys Ser Thr Asn Leu Gly Ser Gly Thr
                485                 490                 495

Ser Val Val Lys Gly Pro Gly Phe Thr Gly Gly Asp Ile Leu Arg Arg
            500                 505                 510

Thr Ser Pro Gly Gln Ile Ser Thr Leu Arg Val Asn Ile Thr Ala Pro
        515                 520                 525
```

| | | | | | | | | | | | | | | |
|---|---|---|---|---|---|---|---|---|---|---|---|---|---|---|
| Leu | Ser | Gln | Arg | Tyr | Arg | Val | Arg | Ile | Arg | Tyr | Ala | Ser | Thr | Thr | Asn |
| | 530 | | | | | 535 | | | | | 540 | | | | |
| Leu | Gln | Phe | His | Thr | Ser | Ile | Asp | Gly | Arg | Pro | Ile | Asn | Gln | Gly | Asn |
| 545 | | | | | 550 | | | | | 555 | | | | | 560 |
| Phe | Ser | Ala | Thr | Met | Ser | Ser | Gly | Ser | Asn | Leu | Gln | Ser | Gly | Ser | Phe |
| | | | | 565 | | | | | 570 | | | | | 575 | |
| Arg | Thr | Val | Gly | Phe | Thr | Thr | Pro | Phe | Asn | Phe | Ser | Asn | Gly | Ser | Ser |
| | | | 580 | | | | | 585 | | | | | 590 | | |
| Val | Phe | Thr | Leu | Ser | Ala | His | Val | Phe | Asn | Ser | Gly | Asn | Glu | Val | Tyr |
| | | 595 | | | | | 600 | | | | | 605 | | | |
| Ile | Asp | Arg | Ile | Glu | Phe | Val | Pro | Ala | Glu | Val | Thr | Phe | Glu | Ala | Glu |
| 610 | | | | | 615 | | | | | | 620 | | | | |
| Tyr | Asp | Leu | Glu | Arg | Ala | Gln | Lys | Ala | Val | Asn | Glu | Leu | Phe | Thr | Ser |
| 625 | | | | | 630 | | | | | 635 | | | | | 640 |
| Ser | Asn | Gln | Ile | Gly | Leu | Lys | Thr | Asp | Val | Thr | Asp | Tyr | His | Ile | Asp |
| | | | | 645 | | | | | 650 | | | | | 655 | |
| Gln | Val | Ser | Asn | Leu | Val | Glu | Cys | Leu | Ser | Asp | Glu | Phe | Cys | Leu | Asp |
| | | | 660 | | | | 665 | | | | | 670 | | | |
| Glu | Lys | Lys | Glu | Leu | Ser | Glu | Lys | Val | Lys | His | Ala | Lys | Arg | Leu | Ser |
| | | 675 | | | | | 680 | | | | | 685 | | | |
| Asp | Glu | Arg | Asn | Leu | Leu | Gln | Asp | Pro | Asn | Phe | Arg | Gly | Ile | Asn | Arg |
| | 690 | | | | | 695 | | | | | 700 | | | | |
| Gln | Leu | Asp | Arg | Gly | Trp | Arg | Gly | Ser | Thr | Asp | Ile | Thr | Ile | Gln | Gly |
| 705 | | | | | 710 | | | | | 715 | | | | | 720 |
| Gly | Asp | Asp | Val | Phe | Lys | Glu | Asn | Tyr | Val | Thr | Leu | Leu | Gly | Thr | Phe |
| | | | | 725 | | | | | 730 | | | | | 735 | |
| Asp | Glu | Cys | Tyr | Pro | Thr | Tyr | Leu | Tyr | Gln | Lys | Ile | Asp | Glu | Ser | Lys |
| | | | 740 | | | | | 745 | | | | | 750 | | |
| Leu | Lys | Ala | Tyr | Thr | Arg | Tyr | Gln | Leu | Arg | Gly | Tyr | Ile | Glu | Asp | Ser |
| | | 755 | | | | | 760 | | | | | 765 | | | |
| Gln | Asp | Leu | Glu | Ile | Tyr | Leu | Ile | Arg | Tyr | Asn | Ala | Lys | His | Glu | Thr |
| | 770 | | | | | 775 | | | | | 780 | | | | |
| Val | Asn | Val | Pro | Gly | Thr | Gly | Ser | Leu | Trp | Pro | Leu | Ser | Ala | Pro | Ser |
| 785 | | | | | 790 | | | | | 795 | | | | | 800 |
| Pro | Ile | Gly | Lys | Cys | Ala | His | His | Ser | His | His | Phe | Ser | Leu | Asp | Ile |
| | | | | 805 | | | | | 810 | | | | | 815 | |
| Asp | Val | Gly | Cys | Thr | Asp | Leu | Asn | Glu | Asp | Leu | Gly | Val | Trp | Val | Ile |
| | | | 820 | | | | | 825 | | | | | 830 | | |
| Phe | Lys | Ile | Lys | Thr | Gln | Asp | Gly | His | Ala | Arg | Leu | Gly | Asn | Leu | Glu |
| | | 835 | | | | | 840 | | | | | 845 | | | |
| Phe | Leu | Glu | Glu | Lys | Pro | Leu | Val | Gly | Glu | Ala | Leu | Ala | Arg | Val | Lys |
| | 850 | | | | | 855 | | | | | 860 | | | | |
| Arg | Ala | Glu | Lys | Lys | Trp | Arg | Asp | Lys | Arg | Glu | Lys | Leu | Glu | Trp | Glu |
| 865 | | | | | 870 | | | | | 875 | | | | | 880 |
| Thr | Asn | Ile | Val | Tyr | Lys | Glu | Ala | Lys | Glu | Ser | Val | Asp | Ala | Leu | Phe |
| | | | | 885 | | | | | 890 | | | | | 895 | |
| Val | Asn | Ser | Gln | Tyr | Asp | Arg | Leu | Gln | Ala | Asp | Thr | Asn | Ile | Ala | Met |
| | | | 900 | | | | | 905 | | | | | 910 | | |
| Ile | His | Ala | Ala | Asp | Lys | Arg | Val | His | Ser | Ile | Arg | Glu | Ala | Tyr | Leu |
| | | 915 | | | | | 920 | | | | | 925 | | | |
| Pro | Glu | Leu | Ser | Val | Ile | Pro | Gly | Val | Asn | Ala | Ala | Ile | Phe | Glu | Glu |
| | 930 | | | | | 935 | | | | | 940 | | | | |
| Leu | Glu | Gly | Arg | Ile | Phe | Thr | Ala | Phe | Ser | Leu | Tyr | Asp | Ala | Arg | Asn |

| | | | | | | | | | | | | | | |
|---|---|---|---|---|---|---|---|---|---|---|---|---|---|---|
945 | | | | | 950 | | | | | 955 | | | | | 960

Val  Ile  Lys  Asn  Gly  Asp  Phe  Asn  Asn  Gly  Leu  Ser  Cys  Trp  Asn  Val
               965                     970                     975

Lys  Gly  His  Val  Asp  Val  Glu  Glu  Gln  Asn  Asn  His  Arg  Ser  Val  Leu
               980                     985                     990

Val  Val  Pro  Glu  Trp  Glu  Ala  Glu  Val  Ser  Gln  Glu  Val  Arg  Val  Cys
               995                    1000                    1005

Pro  Gly  Arg  Gly  Tyr  Ile  Leu  Arg  Val  Thr  Ala  Tyr  Lys  Glu  Gly  Tyr
              1010                    1015                    1020

Gly  Glu  Gly  Cys  Val  Thr  Ile  His  Glu  Ile  Glu  Asn  Asn  Thr  Asp  Glu
1025                          1030                    1035                    1040

Leu  Lys  Phe  Ser  Asn  Cys  Val  Glu  Glu  Val  Tyr  Pro  Asn  Asn  Thr
              1045                    1050                    1055

Val  Thr  Cys  Asn  Asp  Tyr  Thr  Ala  Thr  Gln  Glu  Glu  Tyr  Glu  Gly  Thr
              1060                    1065                    1070

Tyr  Thr  Ser  Arg  Asn  Arg  Gly  Tyr  Asp  Gly  Ala  Tyr  Glu  Ser  Asn  Ser
              1075                    1080                    1085

Ser  Val  Pro  Ala  Asp  Tyr  Ala  Ser  Ala  Tyr  Glu  Glu  Lys  Ala  Tyr  Thr
              1090                    1095                    1100

Asp  Gly  Arg  Arg  Asp  Asn  Pro  Cys  Glu  Ser  Asn  Arg  Gly  Tyr  Gly  Asp
1105                          1110                    1115                    1120

Tyr  Thr  Pro  Leu  Pro  Ala  Gly  Tyr  Val  Thr  Lys  Glu  Leu  Glu  Tyr  Phe
              1125                    1130                    1135

Pro  Glu  Thr  Asp  Lys  Val  Trp  Ile  Glu  Ile  Gly  Glu  Thr  Glu  Gly  Thr
              1140                    1145                    1150

Phe  Ile  Val  Asp  Ser  Val  Glu  Leu  Leu  Leu  Met  Glu  Glu
              1155                    1160                    1165

( 2 ) INFORMATION FOR SEQ ID NO:34:

( i ) SEQUENCE CHARACTERISTICS:
       ( A ) LENGTH: 1188 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:34:

Ala  Asx  Cys  Pro  Glu  Pro  Met  Asp  Asn  Asn  Pro  Asn  Ile  Asn  Glu  Cys
1                    5                    10                       15

Ile  Pro  Tyr  Asn  Cys  Leu  Ser  Asn  Pro  Glu  Val  Glu  Val  Leu  Gly  Gly
                20                   25                       30

Glu  Arg  Ile  Glu  Thr  Gly  Tyr  Thr  Pro  Ile  Asp  Ile  Ser  Leu  Ser  Leu
               35                    40                    45

Thr  Gln  Phe  Leu  Leu  Ser  Glu  Phe  Val  Pro  Gly  Ala  Gly  Phe  Val  Leu
     50                    55                        60

Gly  Leu  Val  Asp  Ile  Ile  Trp  Gly  Ile  Phe  Gly  Pro  Ser  Gln  Trp  Asp
65                         70                    75                         80

Ala  Phe  Leu  Val  Gln  Ile  Glu  Gln  Leu  Ile  Asn  Gln  Arg  Ile  Glu  Glu
                85                    90                         95

Phe  Ala  Arg  Asn  Gln  Ala  Ile  Ser  Arg  Leu  Glu  Gly  Leu  Ser  Asn  Leu
               100                   105                    110

Tyr  Gln  Ile  Tyr  Ala  Glu  Ser  Phe  Arg  Glu  Trp  Glu  Ala  Asp  Pro  Thr
          115                        120                   125

Asn  Pro  Ala  Leu  Arg  Glu  Glu  Met  Arg  Ile  Gln  Phe  Asn  Asp  Met  Asn
          130                        135                         140

Ser Ala Leu Thr Thr Ala Ile Pro Leu Phe Ala Val Gln Asn Tyr Gln
145                 150                 155                 160

Val Pro Leu Leu Ser Val Tyr Val Gln Ala Ala Asn Leu His Leu Ser
                165                 170                 175

Val Leu Arg Asp Val Ser Val Phe Gly Gln Arg Trp Gly Phe Asp Ala
            180                 185                 190

Ala Thr Ile Asn Ser Arg Tyr Asn Asp Leu Thr Arg Leu Ile Gly Asn
        195                 200                 205

Tyr Thr Asp Tyr Ala Val Arg Trp Tyr Asn Thr Gly Leu Glu Arg Val
    210                 215                 220

Trp Gly Pro Asp Ser Arg Asp Trp Val Arg Tyr Asn Gln Phe Arg Arg
225                 230                 235                 240

Glu Leu Thr Leu Thr Val Leu Asp Ile Val Ala Leu Phe Pro Asn Tyr
                245                 250                 255

Asp Ser Arg Arg Tyr Pro Ile Arg Thr Val Ser Gln Leu Thr Arg Glu
            260                 265                 270

Ile Tyr Thr Asn Pro Val Leu Glu Asn Phe Asp Gly Ser Phe Arg Gly
        275                 280                 285

Ser Ala Gln Gly Ile Glu Arg Ser Ile Arg Ser Pro His Leu Met Asp
    290                 295                 300

Ile Leu Asn Ser Ile Thr Ile Tyr Thr Asp Ala His Arg Gly Tyr Tyr
305                 310                 315                 320

Tyr Trp Ser Gly His Gln Ile Met Ala Ser Pro Val Gly Phe Ser Gly
                325                 330                 335

Pro Glu Phe Thr Phe Pro Leu Tyr Gly Thr Met Gly Asn Ala Ala Pro
            340                 345                 350

Gln Gln Arg Ile Val Ala Gln Leu Gly Gln Gly Val Tyr Arg Thr Leu
        355                 360                 365

Ser Ser Thr Leu Tyr Arg Arg Pro Phe Asn Ile Gly Ile Asn Asn Gln
    370                 375                 380

Gln Leu Ser Val Leu Asp Gly Thr Glu Phe Ala Tyr Gly Thr Ser Ser
385                 390                 395                 400

Asn Leu Pro Ser Ala Val Tyr Arg Lys Ser Gly Thr Val Asp Ser Leu
                405                 410                 415

Asp Glu Ile Pro Pro Gln Asn Asn Asn Val Pro Pro Arg Gln Gly Phe
            420                 425                 430

Ser His Arg Leu Ser His Val Ser Met Phe Arg Ser Gly Phe Ser Asn
        435                 440                 445

Ser Ser Val Ser Ile Ile Arg Ala Pro Met Phe Ser Trp Ile His Arg
    450                 455                 460

Ser Ala Glu Phe Asn Asn Ile Ile Ala Ser Asp Ser Ile Thr Gln Ile
465                 470                 475                 480

Pro Ala Val Lys Gly Asn Phe Leu Phe Asn Gly Ser Val Ile Ser Gly
                485                 490                 495

Pro Gly Phe Thr Gly Gly Asp Leu Val Arg Leu Asn Ser Ser Gly Asn
            500                 505                 510

Asn Ile Gln Asn Arg Gly Tyr Ile Glu Val Pro Ile His Phe Pro Ser
        515                 520                 525

Thr Ser Thr Arg Tyr Arg Val Arg Val Arg Tyr Ala Ser Val Thr Pro
    530                 535                 540

Ile His Leu Asn Val Asn Trp Gly Asn Ser Ser Ile Phe Ser Asn Thr
545                 550                 555                 560

Val Pro Ala Thr Ala Thr Ser Leu Asp Asn Leu Gln Ser Ser Asp Phe

|     |     |     |     | 565 |     |     |     |     |     | 570 |     |     |     |     |     | 575 |     |
| --- | --- | --- | --- | --- | --- | --- | --- | --- | --- | --- | --- | --- | --- | --- | --- | --- | --- |
| Gly | Tyr | Phe | Glu | Ser | Ala | Asn | Ala | Phe | Thr | Ser | Ser | Leu | Gly | Asn | Ile |  |  |
|  |  |  | 580 |  |  |  |  | 585 |  |  |  |  | 590 |  |  |  |  |
| Val | Gly | Val | Arg | Asn | Phe | Ser | Gly | Thr | Ala | Gly | Val | Ile | Ile | Asp | Arg |  |  |
|  |  | 595 |  |  |  |  | 600 |  |  |  |  | 605 |  |  |  |  |  |
| Phe | Glu | Phe | Ile | Pro | Val | Thr | Ala | Thr | Leu | Glu | Ala | Glu | Tyr | Asn | Leu |  |  |
|  | 610 |  |  |  |  | 615 |  |  |  |  | 620 |  |  |  |  |  |  |
| Glu | Arg | Ala | Gln | Lys | Ala | Val | Asn | Ala | Leu | Phe | Thr | Ser | Thr | Asn | Gln |  |  |
| 625 |  |  |  |  | 630 |  |  |  |  | 635 |  |  |  |  | 640 |  |  |
| Leu | Gly | Leu | Lys | Thr | Asn | Val | Thr | Asp | Tyr | His | Ile | Asp | Gln | Val | Ser |  |  |
|  |  |  |  | 645 |  |  |  |  | 650 |  |  |  |  | 655 |  |  |  |
| Asn | Leu | Val | Thr | Tyr | Leu | Ser | Asp | Glu | Phe | Cys | Leu | Asp | Glu | Lys | Arg |  |  |
|  |  |  | 660 |  |  |  |  | 665 |  |  |  |  | 670 |  |  |  |  |
| Glu | Leu | Ser | Glu | Lys | Val | Lys | His | Ala | Lys | Arg | Leu | Ser | Asp | Glu | Arg |  |  |
|  |  | 675 |  |  |  |  | 680 |  |  |  |  | 685 |  |  |  |  |  |
| Asn | Leu | Leu | Gln | Asp | Ser | Asn | Phe | Lys | Asp | Ile | Asn | Arg | Gln | Pro | Glu |  |  |
|  | 690 |  |  |  |  | 695 |  |  |  |  | 700 |  |  |  |  |  |  |
| Arg | Gly | Trp | Gly | Gly | Ser | Thr | Gly | Ile | Thr | Ile | Gln | Gly | Gly | Asp | Asp |  |  |
| 705 |  |  |  |  | 710 |  |  |  |  | 715 |  |  |  |  | 720 |  |  |
| Val | Phe | Lys | Glu | Asn | Tyr | Val | Thr | Leu | Ser | Gly | Thr | Phe | Asp | Glu | Cys |  |  |
|  |  |  |  | 725 |  |  |  |  | 730 |  |  |  |  | 735 |  |  |  |
| Tyr | Pro | Thr | Tyr | Leu | Tyr | Gln | Lys | Ile | Asp | Glu | Ser | Lys | Leu | Lys | Ala |  |  |
|  |  |  | 740 |  |  |  |  | 745 |  |  |  |  | 750 |  |  |  |  |
| Phe | Thr | Arg | Tyr | Gln | Leu | Arg | Gly | Tyr | Ile | Glu | Asp | Ser | Gln | Asp | Leu |  |  |
|  |  | 755 |  |  |  |  | 760 |  |  |  |  | 765 |  |  |  |  |  |
| Glu | Ile | Tyr | Leu | Ile | Arg | Tyr | Asn | Ala | Lys | His | Glu | Thr | Val | Asn | Val |  |  |
| 770 |  |  |  |  | 775 |  |  |  |  | 780 |  |  |  |  |  |  |  |
| Pro | Gly | Thr | Gly | Ser | Leu | Trp | Pro | Leu | Ser | Ala | Gln | Ser | Pro | Ile | Gly |  |  |
| 785 |  |  |  |  | 790 |  |  |  |  | 795 |  |  |  |  | 800 |  |  |
| Lys | Cys | Gly | Glu | Pro | Asn | Arg | Cys | Ala | Pro | His | Leu | Glu | Trp | Asn | Pro |  |  |
|  |  |  |  | 805 |  |  |  |  | 810 |  |  |  |  | 815 |  |  |  |
| Asp | Leu | Asp | Cys | Ser | Cys | Arg | Asp | Gly | Glu | Lys | Cys | Ala | His | His | Ser |  |  |
|  |  |  | 820 |  |  |  |  | 825 |  |  |  |  | 830 |  |  |  |  |
| His | His | Phe | Ser | Leu | Asp | Ile | Asp | Val | Gly | Cys | Thr | Asp | Leu | Asn | Glu |  |  |
|  |  | 835 |  |  |  |  | 840 |  |  |  |  | 845 |  |  |  |  |  |
| Asp | Leu | Gly | Val | Trp | Val | Ile | Phe | Lys | Ile | Lys | Thr | Gln | Asp | Gly | His |  |  |
|  | 850 |  |  |  |  | 855 |  |  |  |  | 860 |  |  |  |  |  |  |
| Ala | Arg | Leu | Gly | Asn | Leu | Glu | Phe | Leu | Glu | Glu | Lys | Pro | Leu | Val | Gly |  |  |
| 865 |  |  |  |  | 870 |  |  |  |  | 875 |  |  |  |  | 880 |  |  |
| Glu | Ala | Leu | Ala | Arg | Val | Lys | Arg | Ala | Glu | Lys | Lys | Trp | Arg | Asp | Lys |  |  |
|  |  |  |  | 885 |  |  |  |  | 890 |  |  |  |  | 895 |  |  |  |
| Arg | Glu | Lys | Leu | Glu | Trp | Glu | Thr | Asn | Ile | Val | Tyr | Lys | Glu | Ala | Lys |  |  |
|  |  |  | 900 |  |  |  |  | 905 |  |  |  |  | 910 |  |  |  |  |
| Glu | Ser | Val | Asp | Ala | Leu | Phe | Val | Asn | Ser | Gln | Tyr | Asp | Gln | Leu | Gln |  |  |
|  |  | 915 |  |  |  |  | 920 |  |  |  |  | 925 |  |  |  |  |  |
| Ala | Asp | Thr | Asn | Ile | Ala | Met | Ile | His | Ala | Ala | Asp | Lys | Arg | Val | His |  |  |
|  | 930 |  |  |  |  | 935 |  |  |  |  | 940 |  |  |  |  |  |  |
| Ser | Ile | Arg | Glu | Ala | Tyr | Leu | Pro | Glu | Leu | Ser | Val | Ile | Pro | Gly | Val |  |  |
| 945 |  |  |  |  | 950 |  |  |  |  | 955 |  |  |  |  | 960 |  |  |
| Asn | Ala | Ala | Ile | Phe | Glu | Glu | Leu | Glu | Gly | Arg | Ile | Phe | Thr | Ala | Phe |  |  |
|  |  |  |  | 965 |  |  |  |  | 970 |  |  |  |  | 975 |  |  |  |
| Ser | Leu | Tyr | Asp | Ala | Arg | Asn | Val | Ile | Lys | Asn | Gly | Asp | Phe | Asn | Asn |  |  |
|  |  |  | 980 |  |  |  |  | 985 |  |  |  |  | 990 |  |  |  |  |

| | | | | | | | | | | | | | | |
|---|---|---|---|---|---|---|---|---|---|---|---|---|---|---|
| Gly | Leu | Ser 995 | Cys | Trp | Asn | Val | Lys 1000 | Gly | His | Val | Asp | Val 1005 | Glu | Glu | Gln |
| Asn | Asn | His 1010 | Arg | Ser | Val | Leu 1015 | Val | Val | Pro | Glu | Trp 1020 | Glu | Ala | Glu | Val |
| Ser 1025 | Gln | Glu | Val | Arg | Val 1030 | Cys | Pro | Gly | Arg | Gly 1035 | Tyr | Ile | Leu | Arg | Val 1040 |
| Thr | Ala | Tyr | Lys | Glu 1045 | Gly | Tyr | Gly | Glu | Gly 1050 | Cys | Val | Thr | Ile | His 1055 | Glu |
| Ile | Glu | Asn | Asn 1060 | Thr | Asp | Glu | Leu | Lys 1065 | Phe | Ser | Asn | Cys | Val 1070 | Glu | Glu |
| Glu | Val | Tyr 1075 | Pro | Asn | Asn | Thr | Val 1080 | Thr | Cys | Asn | Asp | Tyr | Thr 1085 | Ala | Thr |
| Gln | Glu 1090 | Glu | Tyr | Glu | Gly | Thr 1095 | Tyr | Thr | Ser | Arg | Asn 1100 | Arg | Gly | Tyr | Asp |
| Gly 1105 | Ala | Tyr | Glu | Ser | Asn 1110 | Ser | Ser | Val | Pro | Ala 1115 | Asp | Tyr | Ala | Ser | Ala 1120 |
| Tyr | Glu | Glu | Lys | Ala 1125 | Tyr | Thr | Asp | Gly | Arg 1130 | Arg | Asp | Asn | Pro | Cys 1135 | Glu |
| Ser | Asn | Arg | Gly 1140 | Tyr | Gly | Asp | Tyr | Thr 1145 | Pro | Leu | Pro | Ala | Gly 1150 | Tyr | Val |
| Thr | Lys | Glu 1155 | Leu | Glu | Tyr | Phe | Pro 1160 | Glu | Thr | Asp | Lys | Val 1165 | Trp | Ile | Glu |
| Ile | Gly 1170 | Glu | Thr | Glu | Gly | Thr 1175 | Phe | Ile | Val | Asp | Ser 1180 | Val | Glu | Leu | Leu |
| Leu 1185 | Met | Glu | Glu | | | | | | | | | | | | |